Figure 1A:
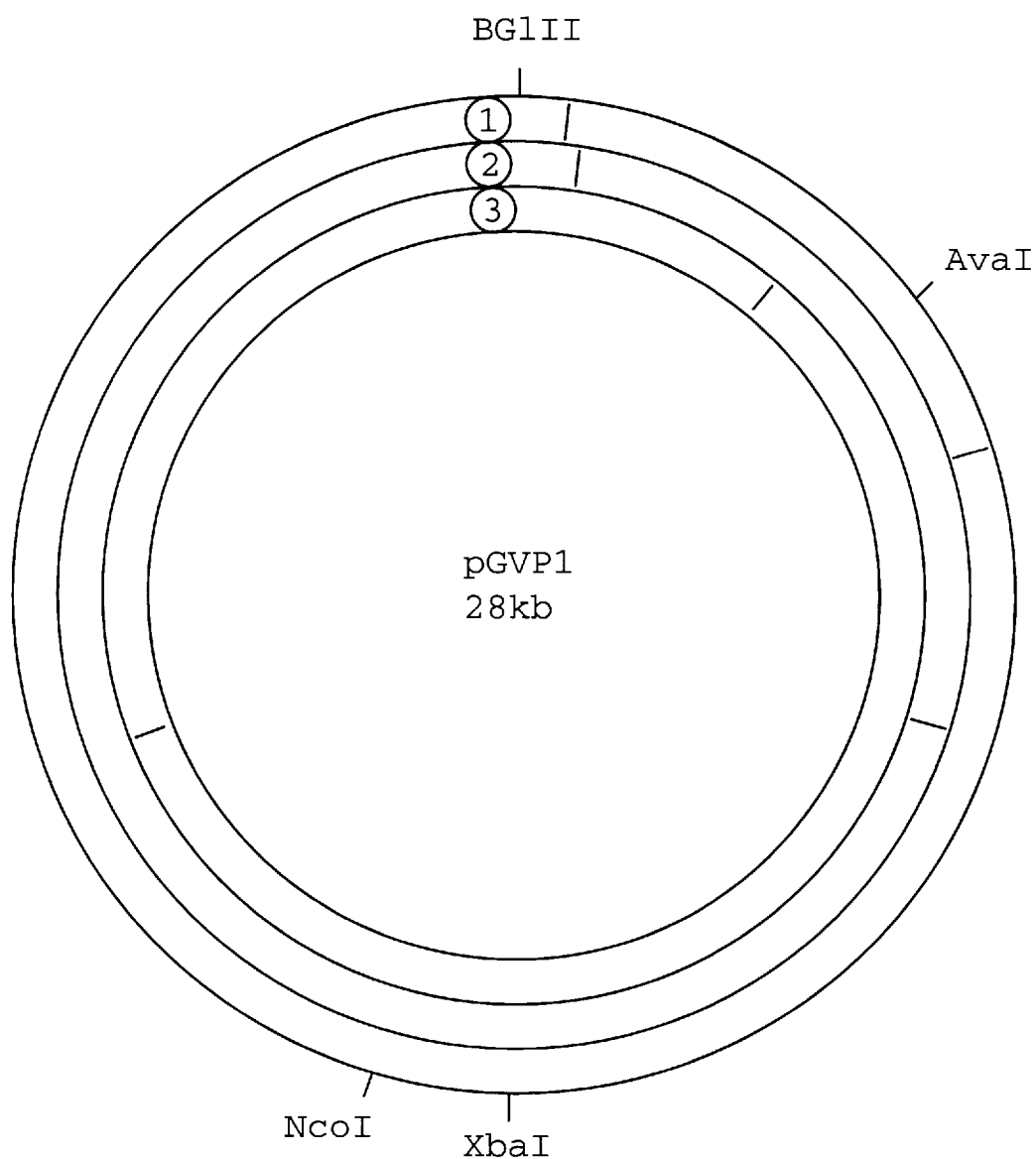

United States Patent [19]
Deblaere et al.

[11] Patent Number: 5,874,267
[45] Date of Patent: Feb. 23, 1999

[54] EXPRESSION OF SURFACE LAYER PROTEINS

[75] Inventors: Rolf Y. Deblaere, Waarschoot; Jan Desomer; Patrick Dhaese, both of Drongen, all of Belgium

[73] Assignee: Solvay (Societe Anonyme), Brussels, Belgium

[21] Appl. No.: 682,517

[22] PCT Filed: Jan. 13, 1995

[86] PCT No.: PCT/EP95/00147

§ 371 Date: Sep. 17, 1996

§ 102(e) Date: Sep. 17, 1996

[87] PCT Pub. No.: WO95/19371

PCT Pub. Date: Jul. 20, 1995

[30] Foreign Application Priority Data

Jan. 14, 1994 [GB] United Kingdom .................. 9400650

[51] Int. Cl.$^6$ ................................. A61K 39/395
[52] U.S. Cl. ................................. 435/173.6; 435/172.3
[58] Field of Search ........................... 435/172.3, 173.6, 435/252.3, 243, 252.32; 536/23.1

[56] References Cited

U.S. PATENT DOCUMENTS 5,043,158  8/1991  Sleytr et al. .

FOREIGN PATENT DOCUMENTS

| 2090549 | 2/1993 | Canada . |
| 0 257 189 | 3/1988 | European Pat. Off. . |
| 2 182 664 | 5/1987 | United Kingdom . |
| WO 86/00929 | 2/1986 | WIPO . |
| WO 91/12819 | 5/1991 | WIPO . |

OTHER PUBLICATIONS

Howard et al, J of Bacteriology (1982) pp. 748–757.
Andrei Lupas et al., "Domain Structure of the Acetogenium kivui Surface Layer Revealed by Electron Crystallography and Sequence Analysis," Journal of Bacteriology, Mar. 1994, pp. 1224–1233, vol. 176, No. 5.
Markus Matuschek et al., "Pullulanase of *Thermoanaerobacterium thermosulfurigenes* EM1 (*Clostridium thermosulfurogenes*): Molecular Analysis of the Gene, Composite Structure of the Enzyme, and a Common Model for its Attachment to the Cell Surface," Journal of Bacteriology, Jun. 1994, pp. 3295–3302, vol. 176, No. 11.
Norihiro Tsukagoshi et al., "Efficient Synthesis and Secretion of a Thermophilic α–Amylase by Protein–Producing *Bacillus brevis* 47 Carrying the *Bacillus stearothermophilus* Amylase Gene," Journal of Bacteriology, Dec. 1985, pp. 1182–1187.
H. König, "Archaeobacterial Cell Envelopes," Can. J. Microbioil., vol. 34, 1988, pp. 395–406.
Hideo Yamagata et al., "Cloning and Characterization of the 5' Region of the Cell Wall Protein Gene Operon in *Bacillus brevis* 47," Journal of Bacteriology, Mar. 1987, pp. 1239–1245.

N. Tsukagoshi, "Characterization and Application of S–Layer Protein Gene for Production of Foreign Proteins in a Protein–Producing *Bacillus brevis* 47," Department of Food Science and Technology, Nagoya University, pp. 145–148.
Takahiro Adachi et al., "Multiple and Tandemly Arranged Promoters of the Cell Wall Protein Gene Operon in *Bacillus brevis* 47," Journal of Bacteriology, Feb. 1989, pp. 1010–1016.
Makoto Takao et al., "Production of Swine Pepsinogen by Protein–Producing *Bacillus brevis* carrying Swine Pepsinogen cDNA," Appl. Microbiol Biotechnol, 1989, vol. 30, pp. 75–80.
Hideo Yamagata et al., "Use of *Bacillus brevis* for Efficient Synthesis and Secretion of Human Epidermal Growth Factor," Proc. Natl. Acad. Sci. USA, vol. 86, May 1989, pp. 3589–3593.
Akio Tsuboi et al., "In Vitro Reconstitution of a Hexagonal Array with a Surface Layer Protein Synthesized by *Bacillus subtilis* Harboring the Surface Layer protein Gene from *Bacillus brevis* 47," Journal of Bacteriology, Dec. 1989, vol. 171, No. 12, pp. 6747–6752.
Maohong Tang et al., "Cloning of the Crystalline Cell Wall Protein Gene of *Bacillus licheniformis* NM 105," Journal of Bacteriology, Dec. 1989, vol. 171, No. 12, pp. 6637–6648.
Ron D. Bowditch et al., "Cloning and Sequencing of the Gene Encoding a 125–Kilodalton Surface–Layer Protein from *Bacillus sphaericus* 2362 and of a Related Cryptic Gene," Journal of Bacteriology, Aug. 1989, vol. 17, No. 8, pp. 4178–4188.
Mingqiang Qiao et al., "New Plasmid Vector and Host System for Genetic Engineering in *Bacillus sphaericus*," Institute for Molecular Biology, Nankai University, Plasmid, May 28, 1991, pp. 237–241.
D. Speck et al., "Isolation of *Bacillus sphaericus* Biotin Synthesis Control Mutants; Evidence for Transcriptional Regulation of bio genes," Gene 108, 1991, pp. 39–45.
Lisa D. Taylor et al., "Transformation of an Entomopathic Strain of *Bacillus Sphaericus* by High Voltage Electroporation," FEMS Microbiology Letters 66 (1990), pp. 125–128.

*Primary Examiner*—Paula K. Hutzell
*Assistant Examiner*—Heather A. Bakalyar
*Attorney, Agent, or Firm*—McDermott, Will & Emery

[57] ABSTRACT

A host cell which is provided with a S-layer comprising a fusion polypeptide consisting essentially of:
(a) at least sufficient of a S-layer protein for a S-layer composed thereof to assemble, and
(b) a heterologous polypeptide which is fused to either the carboxy terminus of (a) or the amino terminus of (a) and which is thereby presented on the outer surface of the said cell; can be used as a vaccine, for screening for proteins and antigens and as a support for immobilizing an enzyme, peptide or antigen. A process of transforming B. Sphaericus cells comprising electroporation is also provided.

1 Claim, 37 Drawing Sheets

GAAAGCTATA ATACATACAT TTAGGTAACT AGGCGGTACT ATAGTTTTCG TTGGATTAAT

ATCAATTTAA GGAATTTTAG GGAGGAATAC ATTA ATG GCA AAG CAA AAC AAA
                                                          Met Ala Lys Gln Asn Lys

GGC CGT AAG TTC TTC GCG GCA TCA GCA ACA GCT GCA TTA GTT GCA TCG
Gly Arg Lys Phe Phe Ala Ala Ser Ala Thr Ala Ala Leu Val Ala Ser

GCA ATC GTA CCT GTA GCA TCT GCT GCA CAA GTA AAC GAC TAT AAC AAA
Ala Ile Val Pro Val Ala Ser Ala Ala Gln Val Asn Asp Tyr Asn Lys

ATC TCT GGA TAC GCT AAA GAA GCA GTT CAA GCT TTA GTT GAC CAA GGC
Ile Ser Gly Tyr Ala Lys Glu Ala Val Gln Ala Leu Val Asp Gln Gly

GTA ATC CAA GGT GAT ACT AAC GGG AAC TTC AAC CCA CTT AAC ACA GTA
Val Ile Gln Gly Asp Thr Asn Gly Asn Phe Asn Pro Leu Asn Thr Val

ACT CGT GCA CAA GCT GCA GAA ATC TTC ACA AAA GCT TTA GAA TTA GAA
Thr Arg Ala Gln Ala Ala Glu Ile Phe Thr Lys Ala Leu Glu Leu Glu

GCT AAC GGA GAT GTA AAC TTC AAA GAC GTG AAA GCT GGC GCT TGG TAC
Ala Asn Gly Asp Val Asn Phe Lys Asp Val Lys Ala Gly Ala Trp Tyr

TAC AAC TCA ATC GCT GCT GTT GTA GCT AAC GGC ATT TTT GAA GGT GTT
Tyr Asn Ser Ile Ala Ala Val Val Ala Asn Gly Ile Phe Glu Gly Val

AGT GCA ACT GAA TTT GCA CCA AAC AAA TCT TTA ACT CGT TCT GAA GCT
Ser Ala Thr Glu Phe Ala Pro Asn Lys Ser Leu Thr Arg Ser Glu Ala

FIG. 6A

```
GCT AAA ATT TTA GTA GAA GCA TTC GGT TTA GAA GGT GAA GCA GAT CTT
Ala Lys Ile Leu Val Glu Ala Phe Gly Leu Glu Gly Glu Ala Asp Leu

AGC GAA TTT GCT GAC GCT TCT CAA GTA AAA CCT TGG GCT AAA AAA TAC
Ser Glu Phe Ala Asp Ala Ser Gln Val Lys Pro Trp Ala Lys Lys Tyr

TTA GAA ATC GCA GTA GCT AAC GGC ATT TTC GAA GGT ACT GAT GCA AAC
Leu Glu Ile Ala Val Ala Asn Gly Ile Phe Glu Gly Thr Asp Ala Asn

AAA CTT AAC CCT AAC AAC TCA ATC ACT CGT CAA GAC TTT GCA CTA GTG
Lys Leu Asn Pro Asn Asn Ser Ile Thr Arg Gln Asp Phe Ala Leu Val

TTC AAA CGT ACA GTT GAC AAA GTT GAA GGT GAA ACT CCA GAA GAA GCA
Phe Lys Arg Thr Val Asp Lys Val Glu Gly Glu Thr Pro Glu Glu Ala

GCA TTT GTT AAA GCT ATC AAC AAC ACA ACT GTT GAA GTA ACA TTC GAA
Ala Phe Val Lys Ala Ile Asn Asn Thr Thr Val Glu Val Thr Phe Glu

GAA GAA GTT ACT AAC GTT CAA GCA CTT AAC TTC AAA ATC GAA GGT TTA
Glu Glu Val Thr Asn Val Gln Ala Leu Asn Phe Lys Ile Glu Gly Leu

GAA ATT AAA AAT GCT TCT GTT AAA CAA ACA AAC AAA AAA GTT GTT GTA
Glu Ile Lys Asn Ala Ser Val Lys gln Thr Asn Lys Lys Val Val Val TTA ACT ACT GAA GCT CAA ACA GCT GAT AAA GAG TAT GTT TTA ACT CTT
Leu Thr Thr Glu Ala Gln Thr Ala Asp Lys Glu Tyr Val Leu Thr Leu GAC GGC GAA ACA ATC GGT GGC TTT AAA GGT GTG GCT GCT GTA GTT CCA
Asp Gly Glu Thr Ile Gly Gly Phe Lys Gly Val Ala Ala Val Val Pro
```

FIG. 6B

ACT AAA GTT GAA CTA GTA TCT TCT GCA GTT CAA GGT AAA CTT GGT CAA
Thr Lys Val Glu Leu Val Ser Ser Ala Val Gln Gly Lys Leu Gly Gln

GAA GTA AAA GTT CAA GCT AAA GTA ACT GTT GCT GAA GGT CAA TCT AAA
Glu Val Lys Val Gln Ala Lys Val Thr Val Ala Glu Gly Gln Ser Lys

GCT GGT ATT CCT GTT ACT TTC ACT GTA CCA GGT AAC AAC AAT GTA GGC
Ala Gly Ile Pro Val Thr Phe Thr Val Pro Gly Asn Asn Asn Val Gly

GTT GTA CCA ACA TTA ACA GGT GAA GCT TTA ACA AAC GAA GAG GGT ATC
Val Val Pro Thr Leu Thr Gly Glu Ala Leu Thr Asn Glu Glu Gly Ile

GCA ACA TAC TCT TAC ACT CGT TAT AAA GAA GGT ACT GAT GAA GTA ACT
Ala Thr Tyr Ser Tyr Thr Arg Tyr Lys Glu Gly Thr Asp Glu Val Thr

GCT TAT GCA ACT GGT GAT CGT TCT AAA TTC TCA CTT GGT TAT GTA TTC
Ala Tyr Ala Thr Gly Asp Arg Ser Lys Phe Ser Leu Gly Tyr Val Phe

TGG GGT GTA GAT ACA ATT CTT TCA GTT GAA GAA GTA ACT ACA GGT GCT
Trp Gly Val Asp Thr Ile Leu Ser Val Glu Glu Val Thr Thr Gly Ala

TCA GTT AAT AAT GGT GCA AAC AAA ACT TAC AAA GTT ACT TAT AAA AAC
Ser Val Asn Asn Gly Ala Asn Lys Thr Tyr Lys Val Thr Tyr Lys Asn

CCT AAA ACT GGT AAA CCA GAA GCA AAC AAA ACA TTT AAT GTT GGT TTT
Pro Lys Thr Gly Lys Pro Glu Ala Asn Lys Thr Phe Asn Val Gly Phe

FIG. 6C

GTA GAA AAC ATG AAT GTT ACT TCT GAT AAA GTA GCA AAT GCT ACA GTT
Val Glu Asn Met Asn Val Thr Ser Asp Lys Val Ala Asn Ala Thr Val

AAT GGC GTA AAA GCA TTA CAA TTA AGC AAT GGT ACA GCT TTA GAC GCT
Asn Gly Val Lys Ala Leu Gln Leu Ser Asn Gly Thr Ala Leu Asp Ala

GCT CAA ATT ACA ACA GAT TCT AAA GGT GAA GCT ACA TTC ACA GTT TCT
Ala Gln Ile Thr Thr Asp Ser Lys Gly Glu Ala Thr Phe Thr Val Ser

GGT ACT AAT GCA GCT GTA ACG CCA GTA GTA TAT GAT CTA CAC AGC ACT
Gly Thr Asn Ala Ala Val Thr Pro Val Val Tyr Asp Lev His Ser Thr

AAC AAT AGT ACT TCA AAT AAA AAA TAT AGT GCA TCT GCT TTA CAA ACT
Asn Asn Ser Thr Ser Asn Lys Lys Tyr Ser Ala Ser Ala Leu Gln Thr

ACT GCT TCT AAA GTA ACT TTC GCT GCT CTT CAA GCA GAG TAT ACA ATT
Thr Ala Ser Lys Val Thr Phe Ala Ala Leu Gln Ala Glu Tyr Thr Ile

GAG TTA ACT CGT GCT GAT AAT GCT GGA GAA GTT GCT GCA ATT GGC GCT
Glu Leu Thr Arg Ala Asp Asn Ala Gly Glu Val Ala Ala Ile Gly Ala

ACT AAC CGGT CGC GAA TAC AAA GTT ATT GTA AAA GAT AAA GCT GGT AAC
Thr Asn Gly Arg Glu Tyr Lys Val Ile Val Lys Asp Lys Ala Gly Asn

TTA GCT AAA AAT GAA ATC GTT AAT GTT GCA TTC AAT GAA GAT AAA GAT
Leu Ala Lys Asn Glu Ile Val Asn Val Ala Phe Asn Glu Asp Lys Asp

FIG. 6D

```
CGT GTA ATT TCA ACA GTT ACA AAT GCA AAA TTC GTT GAT ACT GAT CCA
Arg Val Ile Ser Thr Val Thr Asn Ala Lys Phe Val Asp Thr Asp Pro

GAT ACT GCA GTA TAC TTC ACA GGC GAT AAA GCA AAA CAA ATC TCT GTA
Asp Thr Ala Val Tyr Phe Thr Gly Asp Lys Ala Lys Gln Ile Ser Val

AAA ACA AAT GAT AAA GGT GAA GCT ACA TTT GTT ATC GGT TCT GAT ACA
Lys Thr Asn Asp Lys Gly Glu Ala Thr Phe Val Ile Gly Ser Asp Thr

GTA AAC GAT TAT GCA ACA CCA ATT GCT TGG ATT GAT ATT AAT ACT TCT
Val Asn Asp Tyr Ala Thr Pro Ile Ala Trp Ile Asp Ile Asn Thr Ser

GAT GCA AAA CAA GGC GAC CTT GAT GAA GGT GAA CAA AAA GCA GTT GCA
Asp Ala Lys Gln Gly Asp Leu Asp Glu Gly Glu Pro Lys Ala Val Ala

CCA ATC TCT TAC TTC CAA GCA CCA TAT CTT GAT GGC TCA GCT ATC AAA
Pro Ile Ser Tyr Phe Gln Ala Pro Tyr Leu Asp Gly Ser Ala Ile Lys

GCA TAC AAA AAA TCA GAT CTT AAT AAA GCT GTA ACT AAG TTT GAT GGT
Ala Tyr Lys Lys Ser Asp Leu Asn Lys Ala Val Thr Lys Phe Asp Gly

TCT GAA ACT GCA GTA TTT GCA GCA GAA TTA GTA AAC CAA AGC GGC AAA
Ser Glu Thr Ala Val Phe Ala Ala Glu Leu Val Asn Gln Ser Gly Lys

AAA GTA ACT GGT ACT TCT ATT AAG AAA GCA ACT TAT ACA ATC TAC AAT
Lys Val Thr Gly Thr Ser Ile Lys Lys Ala Thr Tyr Thr Ile Tyr Ans
```

FIG. 6E

ACT GGT GCT AAT GAT ATT AAA GTA GAT AAC CAA GTT ATC TCA CCA AAT
Thr Gly Ala Asn Asp Ile Lys Val Asp Asn Gln Val Ile Ser Pro Asn

CGT AGC TAC ACA GTA ACT TAT GAA GCT ACT TTA TCT TCT ACA GGA ACT
Arg Ser Try Thr Val Thr Tyr Glu Ala Thr Leu Ser Ser Thr Gly Thr

GTT ATT ACA CCT GCT AAG AAT TTA GAA GTT ACT TCA GTG GAT GGT AAA
Val Ile Thr Pro Ala Lys Asn Leu Glu Val Thr Ser Val Asp Gly Lys

ACA ACT GCT GTT AAA GTA ATT GCT ACA GGT ATT GCT GTT AAT ACA GAC
Thr Thr Ala Val Lys Val Ile Ala Thr Gly Ile Ala Val Asn Thr Asp

GGT AAA GAC TAT GCA TTT ACT GCT AAA GAA GCT ACA GCT ACA TTC ACA
Gly Lys Asp Tyr Ala Phe Thr Ala Lys Glu Ala Thr Ala Thr Phe Thr

GCT ACA AAT GAA GTT CCA AAC TCT TAC ACT GGT GTA GCT ACT CAA TCC
Ala Thr Asn Glu Val Pro Asn Ser Tyr Thr Gly Val Ala Thr Gln Phe

AAT ACA GCT GAT TCT GGT TCA AAC AGC AAC TCT ATT TGG TTT GCT GGT
Asn Thr Ala Asp Ser Gly Ser Asn Ser Asn Ser Ile Trp Phe Ala Gly

AAA AAC CCA GTG AAA TAT GCT GGT GTA TCA GGC AAA ACA TAT AAA TAC
Lys Asn Pro Val Lys Tyr Ala Gly Val Ser Gly Lys Thr Tyr Lys Tyr

TTC GGA GCT AAT GGT AAT GAA GTA TTT GGT GAA GCG GCA TGG GAA GCA
Phe Gly Ala Asn Gly Asn Glu Val Phe Gly Glu Ala Ala Trp Glu Ala

FIG. 6F

```
TTA TTA ACT CAA TAT GCA ACT GAA GCC CAA AAA GTA ACA ATC TCA TAT
Leu Leu Thr Gln Tyr Ala Thr Glu Gly Gln Lys Val Thr Ile Ser Tyr

AAT GTA GAT GGT GAT ACA GTT ACA TTT AAA GTA ATT AGT GCT GTT AAT
Asn Val Asp Gly Asp Thr Val Thr Phe Lys Val Ile Ser Ala Val Asn

TCT TCA ACT GAA GCT ATC AAA CCA GTT GCT CCA ACA ACA CCA GCA GCT
Ser Ser Thr Glu Ala Ile Lys Pro Val Ala Pro Thr Thr Pro Ala Ala

CCA ACT ACT GGC GCA TTA ACA TTA ACA CCA GCA GCT GGT GGT TTA GTT
Pro Thr Thr Gly Ala Leu Thr Leu Thr Pro Ala Ala Gly Gly Leu Val

GAT TTA ACA ACT GCA ACT AAC ACT TTA GGA ATT TCA TTA GCT GAT GCA
Asp Leu Thr Thr Ala Thr Asn Thr Leu Gly Ile Ser Leu Ala Asp Ala

GAT CTT AAT GTA AGT GCA ACA ACT GTT GAT ACT GCA ACT GTT TCA TAA
Asp Leu Asn Val Ser Ala Thr Thr Val Asp Thr Ala Thr Val Ser Leu

AAA GAT AGT GCA AAT AAT TCA TTA TCT CTT ACA TTA GTT GAA ACT GGT
Lys Asp Ser Ala Asn Asn Ser Leu Ser Leu Thr Leu Val Glu Thr Gly

GCT AAT ACA GGT GTA TTT GCT ACA ACT GTT CAA GCT GGT ACA TTA TCT
Ala Asn Thr Gly Val Phe Ala Thr Thr Val Gln Ala Gly Thr Leu Ser

TCT TTA ACT GCT GGT ACA TTA ACA GTT ACT TAT GCA GAT GCT AAA AAT
Ser Leu Thr Ala Gly Thr Leu Thr Val Thr Tyr Ala Asp Ala Lys Ans
```

FIG. 6G

```
GCT GCA GGT GTT GCT GAA AAT ATT ACT GCT AGC GTA ACA TTA AAG AAA
Ala Ala Gly Val Ala Glu Asn Ile Thr Ala Ser Val Thr Leu Lys Lys

ACT ACT GGA GCA ATT ACT TCT GAT ACA TTT ACA CAA GGT GTA TTA CCA
Thr Thr Gly Ala Ile Thr Ser Asp Thr Phe Thr Gln Gly Val Leu Pro

TCA GCA GCT ACA GCA GCT GAA TAT ACT TCT AAA TCA ATT GCT GCA GAT
Ser Ala Ala Thr Ala Ala Glu Tyr Thr Ser Lys Ser Ile Ala Ala Asp

TAT ACA TTT GCA ACA GGT GAA GGA TTC ACT TTA AAT ATT GAT AAT GCT
Tyr Thr Phe Ala Thr Gly Glu Gly Phe Thr Leu Asn Ile Asp Asn Ala

GGT GCT CAA GTA ATT AAC TTA GCA GGT AAA AAA GGT GCA CAA GGT GTA
Gly Ala Gln Val Ile Asn Leu Ala Gly Lys Lys Gly Ala Gln Gly Val

GCT GAT GCT ATC AAT GCT ACA TTT GCA GGT ACT GCA ACT GTT TCT GGA
Ala Asp Ala Ile Asn Ala Thr Phe Ala Gly Thr Ala Thr Val Ser Gly

GAC AAA GTA GTT ATT AAA TCA GCT ACA ACA GGT GTT GGT TCT GAA GTT
Asp Lys Val Val Ile Lys Ser Ala Thr Thr Gly Val Gly Ser Glu Val

GAA GTT ACA TTC TCT TCT GTT AAT CAA GTA TTA AAT GCA GTA GTT AAC
Glu Val Thr Phe Ser Ser Val Asn Gln Val Leu Asn Ala Val Val Asn

GGT AAA GAT CAA GTC GTT GCA GGA ACA GCT GCT ACA AAA GCA TTC ACG
Gly Lys Asp Gln Val Val Ala Gly Thr Ala Ala Thr Lys Ala Phe Thr
```

FIG. 6H

```
ATT ACT ACA GCC CTT TCT GTG GGT GAA AAA GTA GTT ATT GAT GGT GTT
Ile Thr Thr Ala Leu Ser Val Gly Glu Lys Val Val Ile Asp Gly Val

GAA TAT ACT GCT GTA GCA TTT GGA ACT GCT CCA ACA GCA AAT ACA TTC
Glu Tyr Thr Ala Val Ala Phe Gly Thr Ala Pro Thr Ala Asn Thr Phe

GTA GTT GAA TCT GCT GCT AAT ACA TTA GCT TCA GTA GCT GAC CAA GCT
Val Val Glu Ser Ala Ala Asn Thr Leu Ala Ser Val Ala Asp Gln Ala

GCA AAT CTT GCT GCT ACA ATT GAT ACT TTA AAC ACT GCA GAT AAG TTT
Ala Asn Leu Ala Ala Thr Ile Asp Thr Leu Asn Thr Ala Asp Lys Phe

ACA GCT TCT GCA ACA GGT GCT ACT ATT ACA TTA ACT TCT ACT GTA ACA
Thr Ala Ser Ala Thr Gly Ala Thr Ile Thr Leu Thr Ser Thr Val Thr

CCA GTA GGT ACT ACA ATT ACT GAA CCA GTA ATT ACA TTA AAA
Pro Val Gly Thr Thr Ile Thr Glu Pro Val Ile Thr Leu Lys

TAAGCAATTA ACTTAAAATA CTTTTAATTA TTTGCCTATT TTATAATTTC TATGACTCTA

TGAGATAACA ATCTCATAGA GTCTTTTTTA TTTTTAGAAC CTCTAGATAG AAAGAAATTT

GAATTTATTA TGAAATTTAT AAAGAAGTCT TGTAACCTTT TATAAGGTAA CTAGTCTAAT

TAAGAGAGTT ATGTAAAAGC AATATATATC GATTCATATT ATTTAAAAGG CTAAAATTAT

TGTTTTAACT CAAACGGGGG TGGTAACAAA AGTTAATCAA GCAGCAATGA GTTTTCTAGA

AAATATTCAT GAAATTCTGG AAATCCTTAT TGCTTTATAT GAAGCTT
```

FIG. 6I

FIG. 8

```
P-1    MAKQNKGRKFFAASATAALVASAIVPVASA   AQVNDYNKISGYAKEAVQAL
2362   .............................   ..LM.F..........S...

P-1    VDQGVIQGDTNGNFNPLNTVTRAQAAEIFTKALELEANGDVNFKDVKAGAW
2362   ..A........A......K.IS.E..T..N......E.........D..

P-1    YYNSIAAVVANGIFEGVSATEFAPNKSLTRSEAAKILVEAFGLEGEADLS
2362   ..DA...T.E...............Q...........D..E....G....

P-1    EFADASQVKPWAKKYLEIAVANGIFEGTDAN-K--LNPNNSITRQDFALV
2362   ........T......S.........VIK.SE..G.TN....AP.......-V
```

```
pSL151      pSL152                                                pSL153
  ↓           ↓                                                     ↓
GAATTCGCTA AGAAACGCCT TCTATATTTC GGTTTCTTTA CAATTATAAC TAAAATATTA
                                                              -35 p3
                                ↓
CGGGAGTCTT TAATTTTTGA CAATTTAGTA ACCATTCCAG AAAATGCTTG GTTATTATTG
                         -10                      -35 p2                      pSL154
              ↓                         ↓
AGAGTAAGGT ATAATAGGTA ACGGAACTAT ATGTTACCAA TCCAAATGAG GATATAATTA
      -10 pSL155
                                          ↓
GTTGTAATTT TAATGGTTTC TACCAAATAC CATATTAGGT ATGGTAAAAA AATCTTCTAT pSL156                                                         p1
    ↓                                                            ↓
AACTAAATTT ATGTCCCAAT GCTTGAATTT CGGAAAAGAT AGTGTTATAT TATTGTAGAA
                          -35                              -10 pSL157
                                                        ↓
AGTGAATAAA CTTACTAGAA TGGTATTCTA CTACGCTTTT TCTAGTAAAT TTACTAACAA pSL158
                                                        ↓
ATTTGCTTTA GTTTTGTATT ATTCAAGAAA GCTATAATAC ATACATTTAG GTAACTAGGC
         -35*                        -10* pSL159
                             ↓
GGTACTATAG TTTTCGTTGG ATTAATATCA ATTTAAGGAA TTTTAGGGAG GAATACATTA
                                                     . . . . . .

ATGGCAAAGC AAAACAAAGG CCGTAAGTTC TTCGCGGCAT CAGCAACAGC TGCATTAGTT

GCATCGGCAA TCGTACCTGT AGCATCTGCT GCACAAGTAA ACGACTATAA CAAAATCTCT
```

FIG. 10

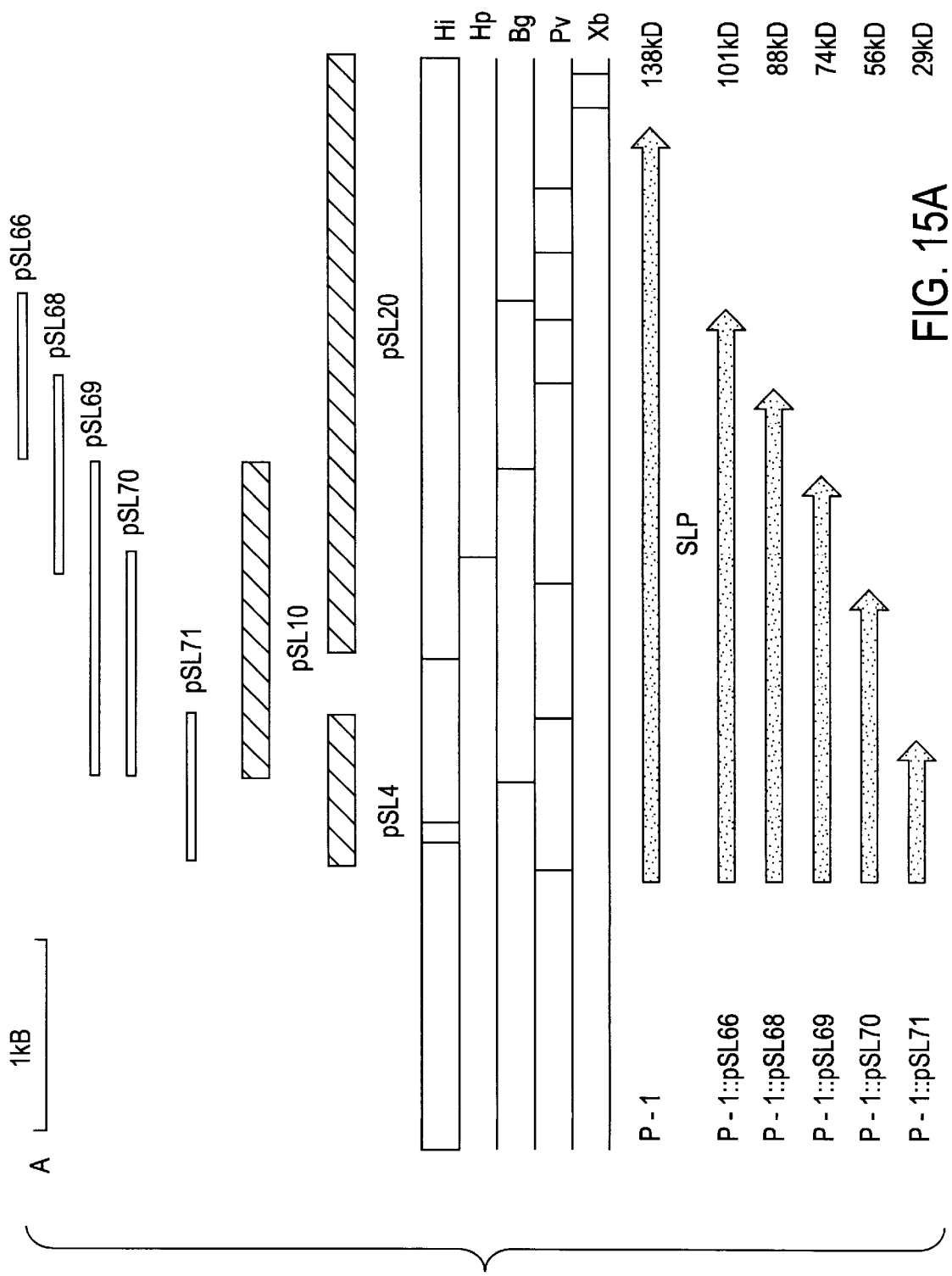

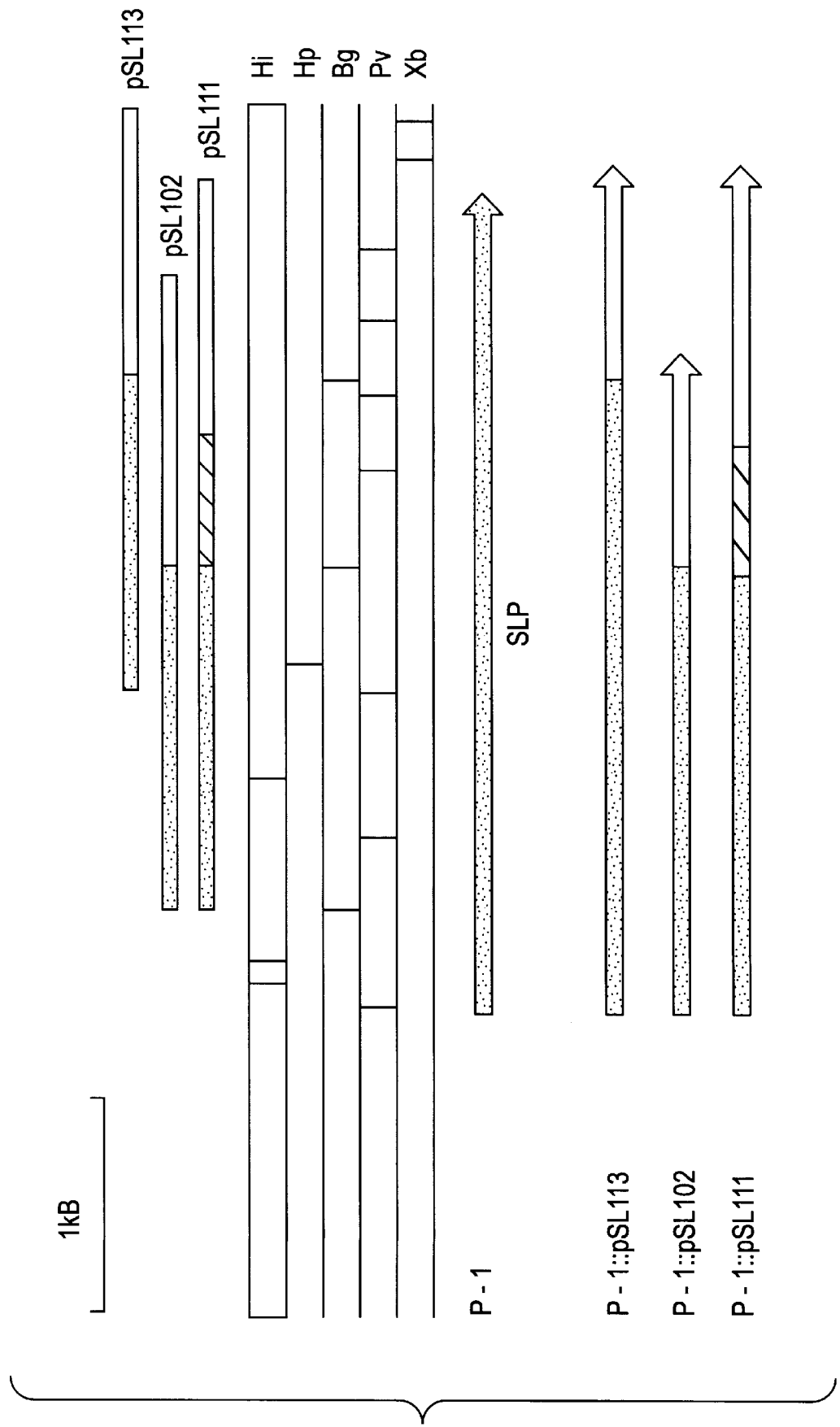

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 1:

TTCGGAAAAG ATAGTGT 17

( 2 ) INFORMATION FOR SEQ ID NO: 2:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

CTAAATTTAT GTCCCAATGC TTGAATTTCG GAAAGATAG TGTTATATTA TTGT 54

( 2 ) INFORMATION FOR SEQ ID NO: 3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

ATTATTGAGA GTAAGG 16

( 2 ) INFORMATION FOR SEQ ID NO: 4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

TCCAGAAAAT GCTTGGTTAT TATTGAGAGT AAGGTATAAT AGGTA 45

( 2 ) INFORMATION FOR SEQ ID NO: 5:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 5:

| GTCTTTAATT TTTGACAA | 18 |
|---|---|

( 2 ) INFORMATION FOR SEQ ID NO: 6:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

| AAAATATTAC GGGAGTCTTT AATTTTGAC AATTTAGTAA CCAT | 44 |
|---|---|

( 2 ) INFORMATION FOR SEQ ID NO: 7:

( i ) SEQUENCE CHARACTERISTICS:
        ( A ) LENGTH: 4197 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 7:

| GAAAGCTATA | ATACATACAT | TTAGGTAACT | AGGCGGTACT | ATAGTTTTCG | TTGGATTAAT | 60 |
|---|---|---|---|---|---|---|
| ATCAATTTAA | GGAATTTTAG | GGAGGAATAC | ATTAATGGCA | AAGCAAAACA | AAGGCCGTAA | 120 |
| GTTCTTCGCG | GCATCAGCAA | CAGCTGCATT | AGTTGCATCG | GCAATCGTAC | CTGTAGCATC | 180 |
| TGCTGCACAA | GTAAACGACT | ATAACAAAAT | CTCTGGATAC | GCTAAAGAAG | CAGTTCAAGC | 240 |
| TTTAGTTGAC | CAAGGCGTAA | TCCAAGGTGA | TACTAACGGG | AACTTCAACC | CACTTAACAC | 300 |
| AGTAACTCGT | GCACAAGCTG | CAGAAATCTT | CACAAAAGCT | TTAGAATTAG | AAGCTAACGG | 360 |
| AGATGTAAAC | TTCAAAGACG | TGAAAGCTGG | CGCTTGGTAC | TACAACTCAA | TCGCTGCTGT | 420 |
| TGTAGCTAAC | GGCATTTTTG | AAGGTGTTAG | TGCAACTGAA | TTTGCACCAA | ACAAATCTTT | 480 |
| AACTCGTTCT | GAAGCTGCTA | AAATTTTAGT | AGAAGCATTC | GGTTTAGAAG | GTGAAGCAGA | 540 |
| TCTTAGCGAA | TTTGCTGACG | CTTCTCAAGT | AAAACCTTGG | GCTAAAAAAT | ACTTAGAAAT | 600 |
| CGCAGTAGCT | AACGGCATTT | TCGAAGGTAC | TGATGCAAAC | AAACTTAACC | CTAACAACTC | 660 |
| AATCACTCGT | CAAGACTTTG | CACTAGTGTT | CAAACGTACA | GTTGACAAAG | TTGAAGGTGA | 720 |
| AACTCCAGAA | GAAGCAGCAT | TTGTTAAAGC | TATCAACAAC | ACAACTGTTG | AAGTAACATT | 780 |
| CGAAGAAGAA | GTTACTAACG | TTCAAGCACT | TAACTTCAAA | ATCGAAGGTT | TAGAAATTAA | 840 |
| AAATGCTTCT | GTTAAACAAA | CAAACAAAAA | AGTTGTTGTA | TTAACTACTG | AAGCTCAAAC | 900 |
| AGCTGATAAA | GAGTATGTTT | TAACTCTTGA | CGGCGAAACA | ATCGGTGGCT | TTAAAGGTGT | 960 |
| GGCTGCTGTA | GTTCCAACTA | AAGTTGAACT | AGTATCTTCT | GCAGTTCAAG | GTAAACTTGG | 1020 |
| TCAAGAAGTA | AAAGTTCAAG | CTAAAGTAAC | TGTTGCTGAA | GGTCAATCTA | AGCTGGTAT | 1080 |
| TCCTGTTACT | TTCACTGTAC | CAGGTAACAA | CAATGATGGC | GTTGTACCAA | CATTAACAGG | 1140 |
| TGAAGCTTTA | ACAAACGAAG | AGGGTATCGC | AACATACTCT | TACACTCGTT | ATAAAGAAGG | 1200 |

```
TACTGATGAA GTAACTGCTT ATGCAACTGG TGATCGTTCT AAATTCTCAC TTGGTTATGT    1260
ATTCTGGGGT GTAGATACAA TTCTTTCAGT TGAAGAAGTA ACTACAGGTG CTTCAGTTAA    1320
TAATGGTGCA AACAAAACTT ACAAAGTTAC TTATAAAAAC CCTAAAACTG GTAAACCAGA    1380
AGCAAACAAA ACATTTAATG TTGGTTTTGT AGAAACATG AATGTTACTT CTGATAAAGT     1440
AGCAAATGCT ACAGTTAATG GCGTAAAAGC ATTACAATTA AGCAATGGTA CAGCTTTAGA    1500
CGCTGCTCAA ATTACAACAG ATTCTAAAGG TGAAGCTACA TTCACAGTTT CTGGTACTAA    1560
TGCAGCTGTA ACGCCAGTAG TATATGATCT ACACAGCACT AACAATAGTA CTTCAAATAA    1620
AAAATATAGT GCATCTGCTT TACAAACTAC TGCTTCTAAA GTAACTTTCG CTGCTCTTCA    1680
AGCAGAGTAT ACAATTGAGT TAACTCGTGC TGATAATGCT GGAGAAGTTG CTGCAATTGG    1740
CGCTACTAAC GGTCGCGAAT ACAAAGTTAT TGTAAAAGAT AAAGCTGGTA ACTTAGCTAA    1800
AAATGAAATC GTTAATGTTG CATTCAATGA AGATAAAGAT CGTGTAATTT CAACAGTTAC    1860
AAATGCTAAA TTCGTTGATA CTGATCCAGA TACTGCAGTA TACTTCACAG GCGATAAAGC    1920
AAAACAAATC TCTGTAAAAA CAAATGATAA AGGTGAAGCT ACATTTGTTA TCGGTTCTGA    1980
TACAGTAAAC GATTATGCAA CACCAATTGC TTGGATTGAT ATTAATACTT CTGATGCAAA    2040
ACAAGGCGAC CTTGATGAAG GTGAACCAAA AGCAGTTGCA CCAATCTCTT ACTTCCAAGC    2100
ACCATATCTT GATGGCTCAG CTATCAAAGC ATACAAAAAA TCAGATCTTA ATAAAGCTGT    2160
AACTAAGTTT GATGGTTCTG AAACTGCAGT ATTTGCAGCA GAATTAGTAA CCAAAGCGG    2220
CAAAAAAGTA ACTGGTACTT CTATTAAGAA AGCAACTTAT ACAATCTACA ATACTGGTGC    2280
TAATGATATT AAAGTAGATA ACCAAGTTAT CTCACCAAAT CGTAGCTACA CAGTAACTTA    2340
TGAAGCTACT TTATCTTCTA CAGGAACTGT TATTACACCT GCTAAGAATT TAGAAGTTAC    2400
TTCAGTGGAT GGTAAAACAA CTGCTGTTAA AGTAATTGCT ACAGGTATTG CTGTTAATAC    2460
AGACGGTAAA GACTATGCAT TTACTGCTAA AGAAGCTACA GCTACATTCA CAGCTACAAA    2520
TGAAGTTCCA AACTCTTACA CTGGTGTAGC TACTCAATTC AATACAGCTG ATTCTGGTTC    2580
AAACAGCAAC TCTATTTGGT TTGCTGGTAA AAACCCAGTG AAATATGCTG GTGTATCAGG    2640
CAAAACATAT AAATACTTCG GAGCTAATGG TAATGAAGTA TTTGGTGAAG CGGCATGGGA    2700
AGCATTATTA ACTCAATATG CAACTGAAGG CCAAAAAGTA ACAATCTCAT ATAATGTAGA    2760
TGGTGATACA GTTACATTTA AAGTAATTAG TGCTGTTAAT TCTTCAACTG AAGCTATCAA    2820
ACCAGTTGCT CCAACAACAC CAGCAGCTCC AACTACTGGC GCATTAACAT TAACACCAGC    2880
AGCTGGTGGT TTAGTTGATT TAACAACTGC AACTAACACT TTAGGAATTT CATTAGCTGA    2940
TGCAGATCTT AATGTAAGTG CAACAACTGT TGATACTGCA ACTGTTTCAT TAAAAGATAG    3000
TGCAAATAAT TCATTATCTC TTACATTAGT TGAAACTGGT GCTAATACAG GTGTATTTGC    3060
TACAACTGTT CAAGCTGGTA CATTATCTTC TTTAACTGCT GGTACATTAA CAGTTACTTA    3120
TGCAGATGCT AAAAATGCTG CAGGTGTTGC TGAAAATATT ACTGCTAGCG TAACATTAAA    3180
GAAAACTACT GGAGCAATTA CTTCTGATAC ATTTACACAA GGTGTATTAC CATCAGCAGC    3240
TACAGCAGCT GAATATACTT CTAAATCAAT TGCTGCAGAT TATACATTTG CAACAGGTGA    3300
AGGATTCACT TTAAATATTG ATAATGCTGG TGCTCAAGTA ATTAACTTAG CAGGTAAAAA    3360
AGGTGCACAA GGTGTAGCTG ATGCTATCAA TGCTACATTT GCAGGTACTG CAACTGTTTC    3420
TGGAGACAAA GTAGTTATTA AATCAGCTAC AACAGGTGTT GGTTCTGAAG TTGAAGTTAC    3480
ATTCTCTTCT GTTAATCAAG TATTAAATGC AGTAGTTAAC GGTAAAGATC AAGTCGTTGC    3540
AGGAACAGCT GCTACAAAAG CATTCACGAT TACTACAGCC CTTTCTGTGG GTGAAAAAGT    3600
```

| | | | | | |
|---|---|---|---|---|---|
|AGTTATTGAT|GGTGTTGAAT|ATACTGCTGT|AGCATTTGGA|ACTGCTCCAA|CAGCAAATAC| 3660
|ATTCGTAGTT|GAATCTGCTG|CTAATACATT|AGCTTCAGTA|GCTGACCAAG|CTGCAAATCT| 3720
|TGCTGCTACA|ATTGATACTT|TAAACACTGC|AGATAAGTTT|ACAGCTTCTG|CAACAGGTGC| 3780
|TACTATTACA|TTAACTTCTA|CTGTAACACC|AGTAGGTACT|ACAATTACTG|AACCAGTAAT| 3840
|TACATTAAAA|TAAGCAATTA|ACTTAAAATA|CTTTTAATTA|TTTGCCTATT|TTATAATTTC| 3900
|TATGACTCTA|TGAGATAACA|ATCTCATAGA|GTCTTTTTA|TTTTTAGAAC|CTCTAGATAG| 3960
|AAAGAAATTT|GAATTTATTA|TGAAATTTAT|AAAGAAGTCT|TGTAACCTTT|TATAAGGTAA| 4020
|CTAGTCTAAT|TAAGAGAGTT|ATGTAAAAGC|AATATATATC|GATTCATATT|ATTTAAAAGG| 4080
|CTAAAATTAT|TGTTTTAACT|CAAACGGGGG|TGGTAACAAA|AGTTAATCAA|GCAGCAATGA| 4140
|GTTTTCTAGA|AAATATTCAT|GAAATTCTGG|AAATCCTTAT|TGCTTTATAT|GAAGCTT|4197

( 2 ) INFORMATION FOR SEQ ID NO: 8:

( i ) SEQUENCE CHARACTERISTICS:
        ( A ) LENGTH: 4197 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus sphaericus
        ( C ) INDIVIDUAL ISOLATE: P-1

( i x ) FEATURE:
        ( A ) NAME/KEY: CDS
        ( B ) LOCATION:95..3850

( i x ) FEATURE:
        ( A ) NAME/KEY: mat_peptide
        ( B ) LOCATION:185..3850

( i x ) FEATURE:
        ( A ) NAME/KEY: sig_peptide
        ( B ) LOCATION:95..184

( x i ) SEQUENCE DESCRIPTION: SEQ ID NO: 8:

```
GAAAGCTATA ATACATACAT TTAGGTAACT AGGCGGTACT ATAGTTTTCG TTGGATTAAT           60

ATCAATTTAA GGAATTTTAG GGAGGAATAC ATTA ATG GCA AAG CAA AAC AAA             112
                                     Met Ala Lys Gln Asn Lys
                                     - 30                - 2 5

GGC CGT AAG TTC TTC GCG GCA TCA GCA ACA GCT GCA TTA GTT GCA TCG           160
Gly Arg Lys Phe Phe Ala Ala Ser Ala Thr Ala Ala Leu Val Ala Ser
            - 2 0             - 1 5                     - 1 0

GCA ATC GTA CCT GTA GCA TCT GCT GCA CAA GTA AAC GAC TAT AAC AAA           208
Ala Ile Val Pro Val Ala Ser Ala Ala Gln Val Asn Asp Tyr Asn Lys
            - 5                 1                 5

ATC TCT GGA TAC GCT AAA GAA GCA GTT CAA GCT TTA GTT GAC CAA GGC           256
Ile Ser Gly Tyr Ala Lys Glu Ala Val Gln Ala Leu Val Asp Gln Gly
         10              15                  20

GTA ATC CAA GGT GAT ACT AAC GGG AAC TTC AAC CCA CTT AAC ACA GTA           304
Val Ile Gln Gly Asp Thr Asn Gly Asn Phe Asn Pro Leu Asn Thr Val
 2 5              30                  35                      40

ACT CGT GCA CAA GCT GCA GAA ATC TTC ACA AAA GCT TTA GAA TTA GAA           352
Thr Arg Ala Gln Ala Ala Glu Ile Phe Thr Lys Ala Leu Glu Leu Glu
                 4 5                 50                  5 5

GCT AAC GGA GAT GTA AAC TTC AAA GAC GTG AAA GCT GGC GCT TGG TAC           400
Ala Asn Gly Asp Val Asn Phe Lys Asp Val Lys Ala Gly Ala Trp Tyr
              60                  6 5                 7 0
```

| | | | | | | | | | | | | | | | | |
|---|---|---|---|---|---|---|---|---|---|---|---|---|---|---|---|---|
| TAC | AAC | TCA | ATC | GCT | GCT | GTT | GTA | GCT | AAC | GGC | ATT | TTT | GAA | GGT | GTT | 448 |
| Tyr | Asn | Ser | Ile | Ala | Ala | Val | Val | Ala | Asn | Gly | Ile | Phe | Glu | Gly | Val | |
| | | 75 | | | | | 80 | | | | | 85 | | | | |
| AGT | GCA | ACT | GAA | TTT | GCA | CCA | AAC | AAA | TCT | TTA | ACT | CGT | TCT | GAA | GCT | 496 |
| Ser | Ala | Thr | Glu | Phe | Ala | Pro | Asn | Lys | Ser | Leu | Thr | Arg | Ser | Glu | Ala | |
| | 90 | | | | | 95 | | | | | 100 | | | | | |
| GCT | AAA | ATT | TTA | GTA | GAA | GCA | TTC | GGT | TTA | GAA | GGT | GAA | GCA | GAT | CTT | 544 |
| Ala | Lys | Ile | Leu | Val | Glu | Ala | Phe | Gly | Leu | Glu | Gly | Glu | Ala | Asp | Leu | |
| 105 | | | | | 110 | | | | | 115 | | | | | 120 | |
| AGC | GAA | TTT | GCT | GAC | GCT | TCT | CAA | GTA | AAA | CCT | TGG | GCT | AAA | AAA | TAC | 592 |
| Ser | Glu | Phe | Ala | Asp | Ala | Ser | Gln | Val | Lys | Pro | Trp | Ala | Lys | Lys | Tyr | |
| | | | | 125 | | | | | 130 | | | | | 135 | | |
| TTA | GAA | ATC | GCA | GTA | GCT | AAC | GGC | ATT | TTC | GAA | GGT | ACT | GAT | GCA | AAC | 640 |
| Leu | Glu | Ile | Ala | Val | Ala | Asn | Gly | Ile | Phe | Glu | Gly | Thr | Asp | Ala | Asn | |
| | | | 140 | | | | | 145 | | | | | 150 | | | |
| AAA | CTT | AAC | CCT | AAC | AAC | TCA | ATC | ACT | CGT | CAA | GAC | TTT | GCA | CTA | GTG | 688 |
| Lys | Leu | Asn | Pro | Asn | Asn | Ser | Ile | Thr | Arg | Gln | Asp | Phe | Ala | Leu | Val | |
| | | 155 | | | | | 160 | | | | | 165 | | | | |
| TTC | AAA | CGT | ACA | GTT | GAC | AAA | GTT | GAA | GGT | GAA | ACT | CCA | GAA | GAA | GCA | 736 |
| Phe | Lys | Arg | Thr | Val | Asp | Lys | Val | Glu | Gly | Glu | Thr | Pro | Glu | Glu | Ala | |
| | 170 | | | | | 175 | | | | | 180 | | | | | |
| GCA | TTT | GTT | AAA | GCT | ATC | AAC | AAC | ACA | ACT | GTT | GAA | GTA | ACA | TTC | GAA | 784 |
| Ala | Phe | Val | Lys | Ala | Ile | Asn | Asn | Thr | Thr | Val | Glu | Val | Thr | Phe | Glu | |
| 185 | | | | | 190 | | | | | 195 | | | | | 200 | |
| GAA | GAA | GTT | ACT | AAC | GTT | CAA | GCA | CTT | AAC | TTC | AAA | ATC | GAA | GGT | TTA | 832 |
| Glu | Glu | Val | Thr | Asn | Val | Gln | Ala | Leu | Asn | Phe | Lys | Ile | Glu | Gly | Leu | |
| | | | | 205 | | | | | 210 | | | | | 215 | | |
| GAA | ATT | AAA | AAT | GCT | TCT | GTT | AAA | CAA | ACA | AAC | AAA | AAA | GTT | GTT | GTA | 880 |
| Glu | Ile | Lys | Asn | Ala | Ser | Val | Lys | Gln | Thr | Asn | Lys | Lys | Val | Val | Val | |
| | | | 220 | | | | | 225 | | | | | 230 | | | |
| TTA | ACT | ACT | GAA | GCT | CAA | ACA | GCT | GAT | AAA | GAG | TAT | GTT | TTA | ACT | CTT | 928 |
| Leu | Thr | Thr | Glu | Ala | Gln | Thr | Ala | Asp | Lys | Glu | Tyr | Val | Leu | Thr | Leu | |
| | | 235 | | | | | 240 | | | | | 245 | | | | |
| GAC | GGC | GAA | ACA | ATC | GGT | GGC | TTT | AAA | GGT | GTG | GCT | GCT | GTA | GTT | CCA | 976 |
| Asp | Gly | Glu | Thr | Ile | Gly | Gly | Phe | Lys | Gly | Val | Ala | Ala | Val | Val | Pro | |
| | 250 | | | | | 255 | | | | | 260 | | | | | |
| ACT | AAA | GTT | GAA | CTA | GTA | TCT | TCT | GCA | GTT | CAA | GGT | AAA | CTT | GGT | CAA | 1024 |
| Thr | Lys | Val | Glu | Leu | Val | Ser | Ser | Ala | Val | Gln | Gly | Lys | Leu | Gly | Gln | |
| 265 | | | | | 270 | | | | | 275 | | | | | 280 | |
| GAA | GTA | AAA | GTT | CAA | GCT | AAA | GTA | ACT | GTT | GCT | GAA | GGT | CAA | TCT | AAA | 1072 |
| Glu | Val | Lys | Val | Gln | Ala | Lys | Val | Thr | Val | Ala | Glu | Gly | Gln | Ser | Lys | |
| | | | | 285 | | | | | 290 | | | | | 295 | | |
| GCT | GGT | ATT | CCT | GTT | ACT | TTC | ACT | GTA | CCA | GGT | AAC | AAC | AAT | GAT | GGC | 1120 |
| Ala | Gly | Ile | Pro | Val | Thr | Phe | Thr | Val | Pro | Gly | Asn | Asn | Asn | Asp | Gly | |
| | | | 300 | | | | | 305 | | | | | 310 | | | |
| GTT | GTA | CCA | ACA | TTA | ACA | GGT | GAA | GCT | TTA | ACA | AAC | GAA | GAG | GGT | ATC | 1168 |
| Val | Val | Pro | Thr | Leu | Thr | Gly | Glu | Ala | Leu | Thr | Asn | Glu | Glu | Gly | Ile | |
| | | 315 | | | | | 320 | | | | | 325 | | | | |
| GCA | ACA | TAC | TCT | TAC | ACT | CGT | TAT | AAA | GAA | GGT | ACT | GAT | GAA | GTA | ACT | 1216 |
| Ala | Thr | Tyr | Ser | Tyr | Thr | Arg | Tyr | Lys | Glu | Gly | Thr | Asp | Glu | Val | Thr | |
| | 330 | | | | | 335 | | | | | 340 | | | | | |
| GCT | TAT | GCA | ACT | GGT | GAT | CGT | TCT | AAA | TTC | TCA | CTT | GGT | TAT | GTA | TTC | 1264 |
| Ala | Tyr | Ala | Thr | Gly | Asp | Arg | Ser | Lys | Phe | Ser | Leu | Gly | Tyr | Val | Phe | |
| 345 | | | | | 350 | | | | | 355 | | | | | 360 | |
| TGG | GGT | GTA | GAT | ACA | ATT | CTT | TCA | GTT | GAA | GAA | GTA | ACT | ACA | GGT | GCT | 1312 |
| Trp | Gly | Val | Asp | Thr | Ile | Leu | Ser | Val | Glu | Glu | Val | Thr | Thr | Gly | Ala | |
| | | | | 365 | | | | | 370 | | | | | 375 | | |
| TCA | GTT | AAT | AAT | GGT | GCA | AAC | AAA | ACT | TAC | AAA | GTT | ACT | TAT | AAA | AAC | 1360 |
| Ser | Val | Asn | Asn | Gly | Ala | Asn | Lys | Thr | Tyr | Lys | Val | Thr | Tyr | Lys | Asn | |
| | | | 380 | | | | | 385 | | | | | 390 | | | |

| | | | | | | | | | | | | | | | |
|---|---|---|---|---|---|---|---|---|---|---|---|---|---|---|---|
| CCT | AAA | ACT | GGT | AAA | CCA | GAA | GCA | AAC | AAA | ACA | TTT | AAT | GTT | GGT | TTT | 1408 |
| Pro | Lys | Thr | Gly | Lys | Pro | Glu | Ala | Asn | Lys | Thr | Phe | Asn | Val | Gly | Phe | |
| | | 395 | | | | 400 | | | | | 405 | | | | | |
| GTA | GAA | AAC | ATG | AAT | GTT | ACT | TCT | GAT | AAA | GTA | GCA | AAT | GCT | ACA | GTT | 1456 |
| Val | Glu | Asn | Met | Asn | Val | Thr | Ser | Asp | Lys | Val | Ala | Asn | Ala | Thr | Val | |
| 410 | | | | | 415 | | | | | 420 | | | | | | |
| AAT | GGC | GTA | AAA | GCA | TTA | CAA | TTA | AGC | AAT | GGT | ACA | GCT | TTA | GAC | GCT | 1504 |
| Asn | Gly | Val | Lys | Ala | Leu | Gln | Leu | Ser | Asn | Gly | Thr | Ala | Leu | Asp | Ala | |
| 425 | | | | 430 | | | | | 435 | | | | | | 440 | |
| GCT | CAA | ATT | ACA | ACA | GAT | TCT | AAA | GGT | GAA | GCT | ACA | TTC | ACA | GTT | TCT | 1552 |
| Ala | Gln | Ile | Thr | Thr | Asp | Ser | Lys | Gly | Glu | Ala | Thr | Phe | Thr | Val | Ser | |
| | | | | 445 | | | | | 450 | | | | | 455 | | |
| GGT | ACT | AAT | GCA | GCT | GTA | ACG | CCA | GTA | GTA | TAT | GAT | CTA | CAC | AGC | ACT | 1600 |
| Gly | Thr | Asn | Ala | Ala | Val | Thr | Pro | Val | Val | Tyr | Asp | Leu | His | Ser | Thr | |
| | | | 460 | | | | 465 | | | | | 470 | | | | |
| AAC | AAT | AGT | ACT | TCA | AAT | AAA | AAA | TAT | AGT | GCA | TCT | GCT | TTA | CAA | ACT | 1648 |
| Asn | Asn | Ser | Thr | Ser | Asn | Lys | Lys | Tyr | Ser | Ala | Ser | Ala | Leu | Gln | Thr | |
| | | 475 | | | | | 480 | | | | | 485 | | | | |
| ACT | GCT | TCT | AAA | GTA | ACT | TTC | GCT | GCT | CTT | CAA | GCA | GAG | TAT | ACA | ATT | 1696 |
| Thr | Ala | Ser | Lys | Val | Thr | Phe | Ala | Ala | Leu | Gln | Ala | Glu | Tyr | Thr | Ile | |
| | 490 | | | | | 495 | | | | | 500 | | | | | |
| GAG | TTA | ACT | CGT | GCT | GAT | AAT | GCT | GGA | GAA | GTT | GCT | GCA | ATT | GGC | GCT | 1744 |
| Glu | Leu | Thr | Arg | Ala | Asp | Asn | Ala | Gly | Glu | Val | Ala | Ala | Ile | Gly | Ala | |
| 505 | | | | | 510 | | | | | 515 | | | | | 520 | |
| ACT | AAC | GGT | CGC | GAA | TAC | AAA | GTT | ATT | GTA | AAA | GAT | AAA | GCT | GGT | AAC | 1792 |
| Thr | Asn | Gly | Arg | Glu | Tyr | Lys | Val | Ile | Val | Lys | Asp | Lys | Ala | Gly | Asn | |
| | | | | 525 | | | | | 530 | | | | | 535 | | |
| TTA | GCT | AAA | AAT | GAA | ATC | GTT | AAT | GTT | GCA | TTC | AAT | GAA | GAT | AAA | GAT | 1840 |
| Leu | Ala | Lys | Asn | Glu | Ile | Val | Asn | Val | Ala | Phe | Asn | Glu | Asp | Lys | Asp | |
| | | | 540 | | | | | 545 | | | | | 550 | | | |
| CGT | GTA | ATT | TCA | ACA | GTT | ACA | AAT | GCT | AAA | TTC | GTT | GAT | ACT | GAT | CCA | 1888 |
| Arg | Val | Ile | Ser | Thr | Val | Thr | Asn | Ala | Lys | Phe | Val | Asp | Thr | Asp | Pro | |
| | | | 555 | | | | | 560 | | | | | 565 | | | |
| GAT | ACT | GCA | GTA | TAC | TTC | ACA | GGC | GAT | AAA | GCA | AAA | CAA | ATC | TCT | GTA | 1936 |
| Asp | Thr | Ala | Val | Tyr | Phe | Thr | Gly | Asp | Lys | Ala | Lys | Gln | Ile | Ser | Val | |
| | | 570 | | | | | 575 | | | | | 580 | | | | |
| AAA | ACA | AAT | GAT | AAA | GGT | GAA | GCT | ACA | TTT | GTT | ATC | GGT | TCT | GAT | ACA | 1984 |
| Lys | Thr | Asn | Asp | Lys | Gly | Glu | Ala | Thr | Phe | Val | Ile | Gly | Ser | Asp | Thr | |
| 585 | | | | | 590 | | | | | 595 | | | | | 600 | |
| GTA | AAC | GAT | TAT | GCA | ACA | CCA | ATT | GCT | TGG | ATT | GAT | ATT | AAT | ACT | TCT | 2032 |
| Val | Asn | Asp | Tyr | Ala | Thr | Pro | Ile | Ala | Trp | Ile | Asp | Ile | Asn | Thr | Ser | |
| | | | | 605 | | | | | 610 | | | | | 615 | | |
| GAT | GCA | AAA | CAA | GGC | GAC | CTT | GAT | GAA | GGT | GAA | CCA | AAA | GCA | GTT | GCA | 2080 |
| Asp | Ala | Lys | Gln | Gly | Asp | Leu | Asp | Glu | Gly | Glu | Pro | Lys | Ala | Val | Ala | |
| | | | 620 | | | | | 625 | | | | | 630 | | | |
| CCA | ATC | TCT | TAC | TTC | CAA | GCA | CCA | TAT | CTT | GAT | GGC | TCA | GCT | ATC | AAA | 2128 |
| Pro | Ile | Ser | Tyr | Phe | Gln | Ala | Pro | Tyr | Leu | Asp | Gly | Ser | Ala | Ile | Lys | |
| | | 635 | | | | | 640 | | | | | 645 | | | | |
| GCA | TAC | AAA | AAA | TCA | GAT | CTT | AAT | AAA | GCT | GTA | ACT | AAG | TTT | GAT | GGT | 2176 |
| Ala | Tyr | Lys | Lys | Ser | Asp | Leu | Asn | Lys | Ala | Val | Thr | Lys | Phe | Asp | Gly | |
| | 650 | | | | | 655 | | | | | 660 | | | | | |
| TCT | GAA | ACT | GCA | GTA | TTT | GCA | GCA | GAA | TTA | GTA | AAC | CAA | AGC | GGC | AAA | 2224 |
| Ser | Glu | Thr | Ala | Val | Phe | Ala | Ala | Glu | Leu | Val | Asn | Gln | Ser | Gly | Lys | |
| 665 | | | | | 670 | | | | | 675 | | | | | 680 | |
| AAA | GTA | ACT | GGT | ACT | TCT | ATT | AAG | AAA | GCA | ACT | TAT | ACA | ATC | TAC | AAT | 2272 |
| Lys | Val | Thr | Gly | Thr | Ser | Ile | Lys | Lys | Ala | Thr | Tyr | Thr | Ile | Tyr | Asn | |
| | | | | 685 | | | | | 690 | | | | | 695 | | |
| ACT | GGT | GCT | AAT | GAT | ATT | AAA | GTA | GAT | AAC | CAA | GTT | ATC | TCA | CCA | AAT | 2320 |
| Thr | Gly | Ala | Asn | Asp | Ile | Lys | Val | Asp | Asn | Gln | Val | Ile | Ser | Pro | Asn | |
| | | | 700 | | | | | 705 | | | | | 710 | | | |

| | | | | | | | | | | | | | | | | |
|---|---|---|---|---|---|---|---|---|---|---|---|---|---|---|---|---|
| CGT | AGC | TAC | ACA | GTA | ACT | TAT | GAA | GCT | ACT | TTA | TCT | TCT | ACA | GGA | ACT | 2368 |
| Arg | Ser | Tyr | Thr | Val | Thr | Tyr | Glu | Ala | Thr | Leu | Ser | Ser | Thr | Gly | Thr | |
| | 715 | | | | | 720 | | | | | | 725 | | | | |
| GTT | ATT | ACA | CCT | GCT | AAG | AAT | TTA | GAA | GTT | ACT | TCA | GTG | GAT | GGT | AAA | 2416 |
| Val | Ile | Thr | Pro | Ala | Lys | Asn | Leu | Glu | Val | Thr | Ser | Val | Asp | Gly | Lys | |
| 730 | | | | | 735 | | | | | | | 740 | | | | |
| ACA | ACT | GCT | GTT | AAA | GTA | ATT | GCT | ACA | GGT | ATT | GCT | GTT | AAT | ACA | GAC | 2464 |
| Thr | Thr | Ala | Val | Lys | Val | Ile | Ala | Thr | Gly | Ile | Ala | Val | Asn | Thr | Asp | |
| 745 | | | | | 750 | | | | | 755 | | | | | 760 | |
| GGT | AAA | GAC | TAT | GCA | TTT | ACT | GCT | AAA | GAA | GCT | ACA | GCT | ACA | TTC | ACA | 2512 |
| Gly | Lys | Asp | Tyr | Ala | Phe | Thr | Ala | Lys | Glu | Ala | Thr | Ala | Thr | Phe | Thr | |
| | | | | 765 | | | | 770 | | | | | 775 | | | |
| GCT | ACA | AAT | GAA | GTT | CCA | AAC | TCT | TAC | ACT | GGT | GTA | GCT | ACT | CAA | TTC | 2560 |
| Ala | Thr | Asn | Glu | Val | Pro | Asn | Ser | Tyr | Thr | Gly | Val | Ala | Thr | Gln | Phe | |
| | | | 780 | | | | | 785 | | | | | 790 | | | |
| AAT | ACA | GCT | GAT | TCT | GGT | TCA | AAC | AGC | AAC | TCT | ATT | TGG | TTT | GCT | GGT | 2608 |
| Asn | Thr | Ala | Asp | Ser | Gly | Ser | Asn | Ser | Asn | Ser | Ile | Trp | Phe | Ala | Gly | |
| | 795 | | | | | 800 | | | | | 805 | | | | | |
| AAA | AAC | CCA | GTG | AAA | TAT | GCT | GGT | GTA | TCA | GGC | AAA | ACA | TAT | AAA | TAC | 2656 |
| Lys | Asn | Pro | Val | Lys | Tyr | Ala | Gly | Val | Ser | Gly | Lys | Thr | Tyr | Lys | Tyr | |
| | 810 | | | | 815 | | | | | 820 | | | | | | |
| TTC | GGA | GCT | AAT | GGT | AAT | GAA | GTA | TTT | GGT | GAA | GCG | GCA | TGG | GAA | GCA | 2704 |
| Phe | Gly | Ala | Asn | Gly | Asn | Glu | Val | Phe | Gly | Glu | Ala | Ala | Trp | Glu | Ala | |
| 825 | | | | 830 | | | | | 835 | | | | | 840 | | |
| TTA | TTA | ACT | CAA | TAT | GCA | ACT | GAA | GGC | AAA | GTA | ACA | ATC | TCA | TAT | | 2752 |
| Leu | Leu | Thr | Gln | Tyr | Ala | Thr | Glu | Gly | Gln | Lys | Val | Thr | Ile | Ser | Tyr | |
| | | | | 845 | | | | | 850 | | | | | 855 | | |
| AAT | GTA | GAT | GGT | GAT | ACA | GTT | ACA | TTT | AAA | GTA | ATT | AGT | GCT | GTT | AAT | 2800 |
| Asn | Val | Asp | Gly | Asp | Thr | Val | Thr | Phe | Lys | Val | Ile | Ser | Ala | Val | Asn | |
| | | | 860 | | | | 865 | | | | | 870 | | | | |
| TCT | TCA | ACT | GAA | GCT | ATC | AAA | CCA | GTT | GCT | CCA | ACA | ACA | CCA | GCA | GCT | 2848 |
| Ser | Ser | Thr | Glu | Ala | Ile | Lys | Pro | Val | Ala | Pro | Thr | Thr | Pro | Ala | Ala | |
| | | 875 | | | | 880 | | | | | 885 | | | | | |
| CCA | ACT | ACT | GGC | GCA | TTA | ACA | TTA | ACA | CCA | GCA | GCT | GGT | GGT | TTA | GTT | 2896 |
| Pro | Thr | Thr | Gly | Ala | Leu | Thr | Leu | Thr | Pro | Ala | Ala | Gly | Gly | Leu | Val | |
| | | 890 | | | | 895 | | | | | 900 | | | | | |
| GAT | TTA | ACA | ACT | GCA | ACT | AAC | ACT | TTA | GGA | ATT | TCA | TTA | GCT | GAT | GCA | 2944 |
| Asp | Leu | Thr | Thr | Ala | Thr | Asn | Thr | Leu | Gly | Ile | Ser | Leu | Ala | Asp | Ala | |
| 905 | | | | | 910 | | | | | 915 | | | | | 920 | |
| GAT | CTT | AAT | GTA | AGT | GCA | ACA | ACT | GTT | GAT | ACT | GCA | ACT | GTT | TCA | TTA | 2992 |
| Asp | Leu | Asn | Val | Ser | Ala | Thr | Thr | Val | Asp | Thr | Ala | Thr | Val | Ser | Leu | |
| | | | | 925 | | | | | 930 | | | | | 935 | | |
| AAA | GAT | AGT | GCA | AAT | AAT | TCA | TTA | TCT | CTT | ACA | TTA | GTT | GAA | ACT | GGT | 3040 |
| Lys | Asp | Ser | Ala | Asn | Asn | Ser | Leu | Ser | Leu | Thr | Leu | Val | Glu | Thr | Gly | |
| | | | 940 | | | | | 945 | | | | | 950 | | | |
| GCT | AAT | ACA | GGT | GTA | TTT | GCA | ACA | ACT | GTT | CAA | GCT | GGT | ACA | TTA | TCT | 3088 |
| Ala | Asn | Thr | Gly | Val | Phe | Ala | Thr | Thr | Val | Gln | Ala | Gly | Thr | Leu | Ser | |
| | | 955 | | | | 960 | | | | | 965 | | | | | |
| TCT | TTA | ACT | GCT | GGT | ACA | TTA | ACA | GTT | ACT | TAT | GCA | GAT | GCT | AAA | AAT | 3136 |
| Ser | Leu | Thr | Ala | Gly | Thr | Leu | Thr | Val | Thr | Tyr | Ala | Asp | Ala | Lys | Asn | |
| | | 970 | | | | 975 | | | | | 980 | | | | | |
| GCT | GCA | GGT | GTT | GCT | GAA | AAT | ATT | ACT | GCT | AGC | GTA | ACA | TTA | AAG | AAA | 3184 |
| Ala | Ala | Gly | Val | Ala | Glu | Asn | Ile | Thr | Ala | Ser | Val | Thr | Leu | Lys | Lys | |
| 985 | | | | | 990 | | | | | 995 | | | | | 1000 | |
| ACT | ACT | GGA | GCA | ATT | ACT | TCT | GAT | ACA | TTT | ACA | CAA | GGT | GTA | TTA | CCA | 3232 |
| Thr | Thr | Gly | Ala | Ile | Thr | Ser | Asp | Thr | Phe | Thr | Gln | Gly | Val | Leu | Pro | |
| | | | | 1005 | | | | 1010 | | | | | 1015 | | | |
| TCA | GCA | GCT | ACA | GCA | GCT | GAA | TAT | ACT | TCT | AAA | TCA | ATT | GCT | GCA | GAT | 3280 |
| Ser | Ala | Ala | Thr | Ala | Ala | Glu | Tyr | Thr | Ser | Lys | Ser | Ile | Ala | Ala | Asp | |
| | | | 1020 | | | | | 1025 | | | | | 1030 | | | |

| | | | | | | | | | | | | | | | | |
|---|---|---|---|---|---|---|---|---|---|---|---|---|---|---|---|---|
| TAT | ACA | TTT | GCA | ACA | GGT | GAA | GGA | TTC | ACT | TTA | AAT | ATT | GAT | AAT | GCT | 3328 |
| Tyr | Thr | Phe | Ala | Thr | Gly | Glu | Gly | Phe | Thr | Leu | Asn | Ile | Asp | Asn | Ala | |
| | | | | 1035 | | | | | 1040 | | | | 1045 | | | |
| GGT | GCT | CAA | GTA | ATT | AAC | TTA | GCA | GGT | AAA | AAA | GGT | GCA | CAA | GGT | GTA | 3376 |
| Gly | Ala | Gln | Val | Ile | Asn | Leu | Ala | Gly | Lys | Lys | Gly | Ala | Gln | Gly | Val | |
| | | | | 1050 | | | | | 1055 | | | | | 1060 | | |
| GCT | GAT | GCT | ATC | AAT | GCT | ACA | TTT | GCA | GGT | ACT | GCA | ACT | GTT | TCT | GGA | 3424 |
| Ala | Asp | Ala | Ile | Asn | Ala | Thr | Phe | Ala | Gly | Thr | Ala | Thr | Val | Ser | Gly | |
| 1065 | | | | | 1070 | | | | | 1075 | | | | | 1080 | |
| GAC | AAA | GTA | GTT | ATT | AAA | TCA | GCT | ACA | ACA | GGT | GTT | GGT | TCT | GAA | GTT | 3472 |
| Asp | Lys | Val | Val | Ile | Lys | Ser | Ala | Thr | Thr | Gly | Val | Gly | Ser | Glu | Val | |
| | | | | 1085 | | | | | 1090 | | | | 1095 | | | |
| GAA | GTT | ACA | TTC | TCT | TCT | GTT | AAT | CAA | GTA | TTA | AAT | GCA | GTA | GTT | AAC | 3520 |
| Glu | Val | Thr | Phe | Ser | Ser | Val | Asn | Gln | Val | Leu | Asn | Ala | Val | Val | Asn | |
| | | | | 1100 | | | | | 1105 | | | | 1110 | | | |
| GGT | AAA | GAT | CAA | GTC | GTT | GCA | GGA | ACA | GCT | GCT | ACA | AAA | GCA | TTC | ACG | 3568 |
| Gly | Lys | Asp | Gln | Val | Val | Ala | Gly | Thr | Ala | Ala | Thr | Lys | Ala | Phe | Thr | |
| | | | 1115 | | | | | 1120 | | | | | 1125 | | | |
| ATT | ACT | ACA | GCC | CTT | TCT | GTG | GGT | GAA | AAA | GTA | GTT | ATT | GAT | GGT | GTT | 3616 |
| Ile | Thr | Thr | Ala | Leu | Ser | Val | Gly | Glu | Lys | Val | Val | Ile | Asp | Gly | Val | |
| | | 1130 | | | | | 1135 | | | | | 1140 | | | | |
| GAA | TAT | ACT | GCT | GTA | GCA | TTT | GGA | ACT | GCT | CCA | ACA | GCA | AAT | ACA | TTC | 3664 |
| Glu | Tyr | Thr | Ala | Val | Ala | Phe | Gly | Thr | Ala | Pro | Thr | Ala | Asn | Thr | Phe | |
| 1145 | | | | | 1150 | | | | | 1155 | | | | | 1160 | |
| GTA | GTT | GAA | TCT | GCT | GCT | AAT | ACA | TTA | GCT | TCA | GTA | GCT | GAC | CAA | GCT | 3712 |
| Val | Val | Glu | Ser | Ala | Ala | Asn | Thr | Leu | Ala | Ser | Val | Ala | Asp | Gln | Ala | |
| | | | | 1165 | | | | | 1170 | | | | | 1175 | | |
| GCA | AAT | CTT | GCT | GCT | ACA | ATT | GAT | ACT | TTA | AAC | ACT | GCA | GAT | AAG | TTT | 3760 |
| Ala | Asn | Leu | Ala | Ala | Thr | Ile | Asp | Thr | Leu | Asn | Thr | Ala | Asp | Lys | Phe | |
| | | | | | 1180 | | | | | 1185 | | | | 1190 | | |
| ACA | GCT | TCT | GCA | ACA | GGT | GCT | ACT | ATT | ACA | TTA | ACT | TCT | ACT | GTA | ACA | 3808 |
| Thr | Ala | Ser | Ala | Thr | Gly | Ala | Thr | Ile | Thr | Leu | Thr | Ser | Thr | Val | Thr | |
| | | | 1195 | | | | | 1200 | | | | | 1205 | | | |
| CCA | GTA | GGT | ACT | ACA | ATT | ACT | GAA | CCA | GTA | ATT | ACA | TTA | AAA | | | 3850 |
| Pro | Val | Gly | Thr | Thr | Ile | Thr | Glu | Pro | Val | Ile | Thr | Leu | Lys | | | |
| | | 1210 | | | | | 1215 | | | | | 1220 | | | | |
| TAAGCAATTA | ACTTAAAATA | CTTTTAATTA | TTTGCCTATT | TTATAATTTC | TATGACTCTA | | | | | | | | | | | 3910 |
| TGAGATAACA | ATCTCATAGA | GTCTTTTTA | TTTTTAGAAC | CTCTAGATAG | AAAGAAATTT | | | | | | | | | | | 3970 |
| GAATTTATTA | TGAAATTTAT | AAAGAAGTCT | TGTAACCTTT | TATAAGGTAA | CTAGTCTAAT | | | | | | | | | | | 4030 |
| TAAGAGAGTT | ATGTAAAAGC | AATATATATC | GATTCATATT | ATTTAAAAGG | CTAAAATTAT | | | | | | | | | | | 4090 |
| TGTTTTAACT | CAAACGGGGG | TGGTAACAAA | AGTTAATCAA | GCAGCAATGA | GTTTTCTAGA | | | | | | | | | | | 4150 |
| AAATATTCAT | GAAATTCTGG | AAATCCTTAT | TGCTTTATAT | GAAGCTT | | | | | | | | | | | | 4197 |

( 2 ) INFORMATION FOR SEQ ID NO: 9:

( i ) SEQUENCE CHARACTERISTICS:
        ( A ) LENGTH: 1252 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

| | | | | | | | | | | | | | | |
|---|---|---|---|---|---|---|---|---|---|---|---|---|---|---|
| Met | Ala | Lys | Gln | Asn | Lys | Gly | Arg | Lys | Phe | Phe | Ala | Ala | Ser | Ala | Thr |
| -30 | | | | | -25 | | | | | -20 | | | | | -15 |
| Ala | Ala | Leu | Val | Ala | Ser | Ala | Ile | Val | Pro | Val | Ala | Ser | Ala | Ala | Gln |
| | | | | -10 | | | | | -5 | | | | | | 1 |
| Val | Asn | Asp | Tyr | Asn | Lys | Ile | Ser | Gly | Tyr | Ala | Lys | Glu | Ala | Val | Gln |
| | | | | 5 | | | | | 10 | | | | | 15 | |

```
Ala Leu Val Asp Gln Gly Val Ile Gln Gly Asp Thr Asn Gly Asn Phe
    20                  25                  30
Asn Pro Leu Asn Thr Val Thr Arg Ala Gln Ala Ala Glu Ile Phe Thr
35                  40                  45                      50
Lys Ala Leu Glu Leu Glu Ala Asn Gly Asp Val Asn Phe Lys Asp Val
                    55                  60                  65
Lys Ala Gly Ala Trp Tyr Tyr Asn Ser Ile Ala Ala Val Val Ala Asn
                70                  75                  80
Gly Ile Phe Glu Gly Val Ser Ala Thr Glu Phe Ala Pro Asn Lys Ser
            85                  90                  95
Leu Thr Arg Ser Glu Ala Ala Lys Ile Leu Val Glu Ala Phe Gly Leu
    100                 105                 110
Glu Gly Glu Ala Asp Leu Ser Glu Phe Ala Asp Ala Ser Gln Val Lys
115                 120                 125                 130
Pro Trp Ala Lys Lys Tyr Leu Glu Ile Ala Val Ala Asn Gly Ile Phe
                135                 140                 145
Glu Gly Thr Asp Ala Asn Lys Leu Asn Pro Asn Asn Ser Ile Thr Arg
            150                 155                 160
Gln Asp Phe Ala Leu Val Phe Lys Arg Thr Val Asp Lys Val Glu Gly
        165                 170                 175
Glu Thr Pro Glu Glu Ala Ala Phe Val Lys Ala Ile Asn Asn Thr Thr
    180                 185                 190
Val Glu Val Thr Phe Glu Glu Val Thr Asn Val Gln Ala Leu Asn
195                 200                 205                 210
Phe Lys Ile Glu Gly Leu Glu Ile Lys Asn Ala Ser Val Lys Gln Thr
                215                 220                 225
Asn Lys Lys Val Val Val Leu Thr Thr Glu Ala Gln Thr Ala Asp Lys
            230                 235                 240
Glu Tyr Val Leu Thr Leu Asp Gly Glu Thr Ile Gly Gly Phe Lys Gly
        245                 250                 255
Val Ala Ala Val Val Pro Thr Lys Val Glu Leu Val Ser Ser Ala Val
    260                 265                 270
Gln Gly Lys Leu Gly Gln Glu Val Lys Val Gln Ala Lys Val Thr Val
275                 280                 285                 290
Ala Glu Gly Gln Ser Lys Ala Gly Ile Pro Val Thr Phe Thr Val Pro
                295                 300                 305
Gly Asn Asn Asn Asp Gly Val Val Pro Thr Leu Thr Gly Glu Ala Leu
            310                 315                 320
Thr Asn Glu Glu Gly Ile Ala Thr Tyr Ser Tyr Thr Arg Tyr Lys Glu
        325                 330                 335
Gly Thr Asp Glu Val Thr Ala Tyr Ala Thr Gly Asp Arg Ser Lys Phe
    340                 345                 350
Ser Leu Gly Tyr Val Phe Trp Gly Val Asp Thr Ile Leu Ser Val Glu
355                 360                 365                 370
Glu Val Thr Thr Gly Ala Ser Val Asn Asn Gly Ala Asn Lys Thr Tyr
                375                 380                 385
Lys Val Thr Tyr Lys Asn Pro Lys Thr Gly Lys Pro Glu Ala Asn Lys
            390                 395                 400
Thr Phe Asn Val Gly Phe Val Glu Asn Met Asn Val Thr Ser Asp Lys
        405                 410                 415
Val Ala Asn Ala Thr Val Asn Gly Val Lys Ala Leu Gln Leu Ser Asn
    420                 425                 430
Gly Thr Ala Leu Asp Ala Ala Gln Ile Thr Thr Asp Ser Lys Gly Glu
```

```
435                     440                     445                     450
Ala  Thr  Phe  Thr  Val  Ser  Gly  Thr  Asn  Ala  Val  Thr  Pro  Val  Val
                         455                     460                     465

Tyr  Asp  Leu  His  Ser  Thr  Asn  Asn  Ser  Thr  Ser  Asn  Lys  Lys  Tyr  Ser
               470                     475                     480

Ala  Ser  Ala  Leu  Gln  Thr  Thr  Ala  Ser  Lys  Val  Thr  Phe  Ala  Ala  Leu
               485                     490                     495

Gln  Ala  Glu  Tyr  Thr  Ile  Glu  Leu  Thr  Arg  Ala  Asp  Asn  Ala  Gly  Glu
     500                     505                     510

Val  Ala  Ala  Ile  Gly  Ala  Thr  Asn  Gly  Arg  Glu  Tyr  Lys  Val  Ile  Val
515                     520                     525                     530

Lys  Asp  Lys  Ala  Gly  Asn  Leu  Ala  Lys  Asn  Glu  Ile  Val  Asn  Val  Ala
                    535                     540                     545

Phe  Asn  Glu  Asp  Lys  Asp  Arg  Val  Ile  Ser  Thr  Val  Thr  Asn  Ala  Lys
               550                     555                     560

Phe  Val  Asp  Thr  Asp  Pro  Asp  Thr  Ala  Val  Tyr  Phe  Thr  Gly  Asp  Lys
               565                     570                     575

Ala  Lys  Gln  Ile  Ser  Val  Lys  Thr  Asn  Asp  Lys  Gly  Glu  Ala  Thr  Phe
     580                     585                     590

Val  Ile  Gly  Ser  Asp  Thr  Val  Asn  Asp  Tyr  Ala  Thr  Pro  Ile  Ala  Trp
595                     600                     605                     610

Ile  Asp  Ile  Asn  Thr  Ser  Asp  Ala  Lys  Gln  Gly  Asp  Leu  Asp  Glu  Gly
                    615                     620                     625

Glu  Pro  Lys  Ala  Val  Ala  Pro  Ile  Ser  Tyr  Phe  Gln  Ala  Pro  Tyr  Leu
               630                     635                     640

Asp  Gly  Ser  Ala  Ile  Lys  Ala  Tyr  Lys  Lys  Ser  Asp  Leu  Asn  Lys  Ala
               645                     650                     655

Val  Thr  Lys  Phe  Asp  Gly  Ser  Glu  Thr  Ala  Val  Phe  Ala  Ala  Glu  Leu
     660                     665                     670

Val  Asn  Gln  Ser  Gly  Lys  Lys  Val  Thr  Gly  Thr  Ser  Ile  Lys  Lys  Ala
675                     680                     685                     690

Thr  Tyr  Thr  Ile  Tyr  Asn  Thr  Gly  Ala  Asn  Asp  Ile  Lys  Val  Asp  Asn
                    695                     700                     705

Gln  Val  Ile  Ser  Pro  Asn  Arg  Ser  Tyr  Thr  Val  Thr  Tyr  Glu  Ala  Thr
               710                     715                     720

Leu  Ser  Ser  Thr  Gly  Thr  Val  Ile  Thr  Pro  Ala  Lys  Asn  Leu  Glu  Val
               725                     730                     735

Thr  Ser  Val  Asp  Gly  Lys  Thr  Ala  Val  Lys  Val  Ile  Ala  Thr  Gly
     740                     745                     750

Ile  Ala  Val  Asn  Thr  Asp  Gly  Lys  Asp  Tyr  Ala  Phe  Thr  Ala  Lys  Glu
755                     760                     765                     770

Ala  Thr  Ala  Thr  Phe  Thr  Ala  Thr  Asn  Glu  Val  Pro  Asn  Ser  Tyr  Thr
                    775                     780                     785

Gly  Val  Ala  Thr  Gln  Phe  Asn  Thr  Ala  Asp  Ser  Gly  Ser  Asn  Ser  Asn
               790                     795                     800

Ser  Ile  Trp  Phe  Ala  Gly  Lys  Asn  Pro  Val  Lys  Tyr  Ala  Gly  Val  Ser
          805                     810                     815

Gly  Lys  Thr  Tyr  Lys  Tyr  Phe  Gly  Ala  Asn  Gly  Asn  Glu  Val  Phe  Gly
     820                     825                     830

Glu  Ala  Ala  Trp  Glu  Ala  Leu  Leu  Thr  Gln  Tyr  Ala  Thr  Glu  Gly  Gln
835                     840                     845                     850

Lys  Val  Thr  Ile  Ser  Tyr  Asn  Val  Asp  Gly  Asp  Thr  Val  Thr  Phe  Lys
                    855                     860                     865
```

| Val | Ile | Ser | Ala | Val | Asn | Ser | Ser | Thr | Glu | Ala | Ile | Lys | Pro | Val | Ala |
|-----|-----|-----|-----|-----|-----|-----|-----|-----|-----|-----|-----|-----|-----|-----|-----|
|     |     |     | 870 |     |     |     | 875 |     |     |     |     |     | 880 |     |     |

Pro Thr Thr Pro Ala Ala Pro Thr Thr Gly Ala Leu Thr Leu Thr Pro
        885             890                 895

Ala Ala Gly Gly Leu Val Asp Leu Thr Thr Ala Thr Asn Thr Leu Gly
900                     905                 910

Ile Ser Leu Ala Asp Ala Asp Leu Asn Val Ser Ala Thr Val Asp
915             920             925                         930

Thr Ala Thr Val Ser Leu Lys Asp Ser Ala Asn Asn Ser Leu Ser Leu
                935                 940                 945

Thr Leu Val Glu Thr Gly Ala Asn Thr Gly Val Phe Ala Thr Thr Val
            950                 955

Gln Ala Gly Thr Leu Ser Ser Leu Thr Ala Gly Thr Leu Thr Val Thr
        965                 970                 975

Tyr Ala Asp Ala Lys Asn Ala Ala Gly Val Ala Glu Asn Ile Thr Ala
    980                 985                 990

Ser Val Thr Leu Lys Lys Thr Thr Gly Ala Ile Thr Ser Asp Thr Phe
995                 1000                1005                1010

Thr Gln Gly Val Leu Pro Ser Ala Ala Thr Ala Ala Glu Tyr Thr Ser
                1015                1020                1025

Lys Ser Ile Ala Ala Asp Tyr Thr Phe Ala Thr Gly Glu Gly Phe Thr
                1030                1035                1040

Leu Asn Ile Asp Asn Ala Gly Ala Gln Val Ile Asn Leu Ala Gly Lys
            1045                1050                1055

Lys Gly Ala Gln Gly Val Ala Asp Ala Ile Asn Ala Thr Phe Ala Gly
    1060                1065                1070

Thr Ala Thr Val Ser Gly Asp Lys Val Val Ile Lys Ser Ala Thr Thr
1075                1080                1085                1090

Gly Val Gly Ser Glu Val Glu Val Thr Phe Ser Ser Val Asn Gln Val
                1095                1100                1105

Leu Asn Ala Val Val Asn Gly Lys Asp Gln Val Val Ala Gly Thr Ala
            1110                1115                1120

Ala Thr Lys Ala Phe Thr Ile Thr Thr Ala Leu Ser Val Gly Glu Lys
        1125                1130                1135

Val Val Ile Asp Gly Val Glu Tyr Thr Ala Val Ala Phe Gly Thr Ala
1140                1145                1150

Pro Thr Ala Asn Thr Phe Val Val Glu Ser Ala Ala Asn Thr Leu Ala
1155                1160                1165                1170

Ser Val Ala Asp Gln Ala Ala Asn Leu Ala Ala Thr Ile Asp Thr Leu
                1175                1180                1185

Asn Thr Ala Asp Lys Phe Thr Ala Ser Ala Thr Gly Ala Thr Ile Thr
            1190                1195                1200

Leu Thr Ser Thr Val Thr Pro Val Gly Thr Thr Ile Thr Glu Pro Val
        1205                1210                1215

Ile Thr Leu Lys
    1220

( 2 ) INFORMATION FOR SEQ ID NO: 10:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 10:

ATGGCAAAGC AAAACAAAGG CCGTAAGTTC TTCGCGGCAT CAGCAACAGC TGCATTAGTT            60

GCATCGGCAA TCGTACCTGT AGCATCTGCT                                             90

( 2 ) INFORMATION FOR SEQ ID NO: 11:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION:1..90

( x i ) SEQUENCE DESCRIPTION: SEQ ID NO: 11:

```
ATG  GCA  AAG  CAA  AAC  AAA  GGC  CGT  AAG  TTC  TTC  GCG  GCA  TCA  GCA  ACA        48
Met  Ala  Lys  Gln  Asn  Lys  Gly  Arg  Lys  Phe  Phe  Ala  Ala  Ser  Ala  Thr
 1             5                        10                       15

GCT  GCA  TTA  GTT  GCA  TCG  GCA  ATC  GTA  CCT  GTA  GCA  TCT  GCT                  90
Ala  Ala  Leu  Val  Ala  Ser  Ala  Ile  Val  Pro  Val  Ala  Ser  Ala
         20                        25                       30
```

( 2 ) INFORMATION FOR SEQ ID NO: 12:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 12:

```
Met  Ala  Lys  Gln  Asn  Lys  Gly  Arg  Lys  Phe  Phe  Ala  Ala  Ser  Ala  Thr
 1             5                        10                       15

Ala  Ala  Leu  Val  Ala  Ser  Ala  Ile  Val  Pro  Val  Ala  Ser  Ala
         20                        25                       30
```

( 2 ) INFORMATION FOR SEQ ID NO: 13:

( i ) SEQUENCE CHARACTERISTICS:
        ( A ) LENGTH: 3666 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 13:

GCACAAGTAA ACGACTATAA CAAAATCTCT GGATACGCTA AGAAGCAGT TCAAGCTTTA             60

GTTGACCAAG GCGTAATCCA AGGTGATACT AACGGGAACT TCAACCCACT TAACACAGTA           120

ACTCGTGCAC AAGCTGCAGA AATCTTCACA AAAGCTTTAG AATTAGAAGC TAACGGAGAT           180

GTAAACTTCA AAGACGTGAA AGCTGGCGCT TGGTACTACA ACTCAATCGC TGCTGTTGTA           240

GCTAACGGCA TTTTTGAAGG TGTTAGTGCA ACTGAATTTG CACCAAACAA ATCTTTAACT           300

CGTTCTGAAG CTGCTAAAAT TTTAGTAGAA GCATTCGGTT TAGAAGGTGA AGCAGATCTT           360

AGCGAATTTG CTGACGCTTC TCAAGTAAAA CCTTGGGCTA AAAATACTT AGAAATCGCA            420

GTAGCTAACG GCATTTTCGA AGGTACTGAT GCAAACAAAC TTAACCCTAA CAACTCAATC           480

ACTCGTCAAG ACTTTGCACT AGTGTTCAAA CGTACAGTTG ACAAAGTTGA AGGTGAAACT           540

```
CCAGAAGAAG CAGCATTTGT TAAAGCTATC AACAACACAA CTGTTGAAGT AACATTCGAA      600
GAAGAAGTTA CTAACGTTCA AGCACTTAAC TTCAAAATCG AAGGTTTAGA AATTAAAAAT      660
GCTTCTGTTA AACAAACAAA CAAAAAGTT GTTGTATTAA CTACTGAAGC TCAAACAGCT       720
GATAAAGAGT ATGTTTTAAC TCTTGACGGC GAAACAATCG GTGGCTTTAA AGGTGTGGCT      780
GCTGTAGTTC CAACTAAAGT TGAACTAGTA TCTTCTGCAG TTCAAGGTAA ACTTGGTCAA      840
GAAGTAAAAG TTCAAGCTAA AGTAACTGTT GCTGAAGGTC AATCTAAAGC TGGTATTCCT      900
GTTACTTTCA CTGTACCAGG TAACAACAAT GATGGCGTTG TACCAACATT AACAGGTGAA      960
GCTTTAACAA ACGAAGAGGG TATCGCAACA TACTCTTACA CTCGTTATAA AGAAGGTACT     1020
GATGAAGTAA CTGCTTATGC AACTGGTGAT CGTTCTAAAT TCTCACTTGG TTATGTATTC     1080
TGGGGTGTAG ATACAATTCT TTCAGTTGAA GAAGTAACTA CAGGTGCTTC AGTTAATAAT     1140
GGTGCAAACA AAACTTACAA AGTTACTTAT AAAAACCCTA AAACTGGTAA ACCAGAAGCA     1200
AACAAAACAT TTAATGTTGG TTTTGTAGAA AACATGAATG TTACTTCTGA TAAAGTAGCA     1260
AATGCTACAG TTAATGGCGT AAAAGCATTA CAATTAAGCA ATGGTACAGC TTTAGACGCT     1320
GCTCAAATTA CAACAGATTC TAAAGGTGAA GCTACATTCA CAGTTTCTGG TACTAATGCA     1380
GCTGTAACGC CAGTAGTATA TGATCTACAC AGCACTAACA ATAGTACTTC AAATAAAAAA     1440
TATAGTGCAT CTGCTTTACA AACTACTGCT TCTAAAGTAA CTTTCGCTGC TCTTCAAGCA     1500
GAGTATACAA TTGAGTTAAC TCGTGCTGAT AATGCTGGAG AAGTTGCTGC AATTGGCGCT     1560
ACTAACGGTC GCGAATACAA AGTTATTGTA AAAGATAAAG CTGGTAACTT AGCTAAAAAT     1620
GAAATCGTTA ATGTTGCATT CAATGAAGAT AAAGATCGTG TAATTTCAAC AGTTACAAAT     1680
GCTAAATTCG TTGATACTGA TCCAGATACT GCAGTATACT TCACAGGCGA TAAAGCAAAA     1740
CAAATCTCTG TAAAAACAAA TGATAAAGGT GAAGCTACAT TTGTTATCGG TTCTGATACA     1800
GTAAACGATT ATGCAACACC AATTGCTTGG ATTGATATTA ATACTTCTGA TGCAAAACAA     1860
GGCGACCTTG ATGAAGGTGA ACCAAAAGCA GTTGCACCAA TCTCTTACTT CCAAGCACCA     1920
TATCTTGATG GCTCAGCTAT CAAAGCATAC AAAAAATCAG ATCTTAATAA AGCTGTAACT     1980
AAGTTTGATG GTTCTGAAAC TGCAGTATTT GCAGCAGAAT TAGTAAACCA AAGCGGCAAA     2040
AAAGTAACTG GTACTTCTAT TAAGAAAGCA ACTTATACAA TCTACAATAC TGGTGCTAAT     2100
GATATTAAAG TAGATAACCA AGTTATCTCA CCAAATCGTA GCTACACAGT AACTTATGAA     2160
GCTACTTTAT CTTCTACAGG AACTGTTATT ACACCTGCTA AGAATTTAGA AGTTACTTCA     2220
GTGGATGGTA AAACAACTGC TGTTAAAGTA ATTGCTACAG GTATTGCTGT TAATACAGAC     2280
GGTAAAGACT ATGCATTTAC TGCTAAAGAA GCTACAGCTA CATTCACAGC TACAAATGAA     2340
GTTCCAAACT CTTACACTGG TGTAGCTACT CAATTCAATA CAGCTGATTC TGGTTCAAAC     2400
AGCAACTCTA TTTGGTTTGC TGGTAAAAAC CCAGTGAAAT ATGCTGGTGT ATCAGGCAAA     2460
ACATATAAAT ACTTCGGAGC TAATGGTAAT GAAGTATTTG GTGAAGCGGC ATGGGAAGCA     2520
TTATTAACTC AATATGCAAC TGAAGGCCAA AAAGTAACAA TCTCATATAA TGTAGATGGT     2580
GATACAGTTA CATTTAAAGT AATTAGTGCT GTTAATTCTT CAACTGAAGC TATCAAACCA     2640
GTTGCTCCAA CAACACCAGC AGCTCCAACT ACTGGCGCAT TAACATTAAC ACCAGCAGCT     2700
GGTGGTTTAG TTGATTTAAC AACTGCAACT AACACTTTAG GAATTTCATT AGCTGATGCA     2760
GATCTTAATG TAAGTGCAAC AACTGTTGAT ACTGCAACTG TTTCATTAAA AGATAGTGCA     2820
AATAATTCAT TATCTCTTAC ATTAGTTGAA ACTGGTGCTA ATACAGGTGT ATTTGCTACA     2880
ACTGTTCAAG CTGGTACATT ATCTTCTTTA ACTGCTGGTA CATTAACAGT TACTTATGCA     2940
```

| | | | | | | | | | | | | | |
|---|---|---|---|---|---|---|---|---|---|---|---|---|---|
| GATGCTAAAA | ATGCTGCAGG | TGTTGCTGAA | AATATTACTG | CTAGCGTAAC | ATTAAAGAAA | 3000 |
| ACTACTGGAG | CAATTACTTC | TGATACATTT | ACACAAGGTG | TATTACCATC | AGCAGCTACA | 3060 |
| GCAGCTGAAT | ATACTTCTAA | ATCAATTGCT | GCAGATTATA | CATTTGCAAC | AGGTGAAGGA | 3120 |
| TTCACTTTAA | ATATTGATAA | TGCTGGTGCT | CAAGTAATTA | ACTTAGCAGG | TAAAAAGGT | 3180 |
| GCACAAGGTG | TAGCTGATGC | TATCAATGCT | ACATTTGCAG | GTACTGCAAC | TGTTTCTGGA | 3240 |
| GACAAAGTAG | TTATTAAATC | AGCTACAACA | GGTGTTGGTT | CTGAAGTTGA | AGTTACATTC | 3300 |
| TCTTCTGTTA | ATCAAGTATT | AAATGCAGTA | GTTAACGGTA | AAGATCAAGT | CGTTGCAGGA | 3360 |
| ACAGCTGCTA | CAAAAGCATT | CACGATTACT | ACAGCCCTTT | CTGTGGGTGA | AAAAGTAGTT | 3420 |
| ATTGATGGTG | TTGAATATAC | TGCTGTAGCA | TTTGGAACTG | CTCCAACAGC | AAATACATTC | 3480 |
| GTAGTTGAAT | CTGCTGCTAA | TACATTAGCT | TCAGTAGCTG | ACCAAGCTGC | AAATCTTGCT | 3540 |
| GCTACAATTG | ATACTTTAAA | CACTGCAGAT | AAGTTTACAG | CTTCTGCAAC | AGGTGCTACT | 3600 |
| ATTACATTAA | CTTCTACTGT | AACACCAGTA | GGTACTACAA | TTACTGAACC | AGTAATTACA | 3660 |
| TTAAAA | | | | | | 3666 |

( 2 ) INFORMATION FOR SEQ ID NO: 14:

( i ) SEQUENCE CHARACTERISTICS:
      ( A ) LENGTH: 3666 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION:1..3666

( x i ) SEQUENCE DESCRIPTION: SEQ ID NO: 14:

| | | | | | | | | | | | | | | | |
|---|---|---|---|---|---|---|---|---|---|---|---|---|---|---|---|
| GCA | CAA | GTA | AAC | GAC | TAT | AAC | AAA | ATC | TCT | GGA | TAC | GCT | AAA | GAA | GCA | 48 |
| Ala | Gln | Val | Asn | Asp | Tyr | Asn | Lys | Ile | Ser | Gly | Tyr | Ala | Lys | Glu | Ala | |
| 1 | | | | 5 | | | | | 10 | | | | | 15 | | |
| GTT | CAA | GCT | TTA | GTT | GAC | CAA | GGC | GTA | ATC | CAA | GGT | GAT | ACT | AAC | GGG | 96 |
| Val | Gln | Ala | Leu | Val | Asp | Gln | Gly | Val | Ile | Gln | Gly | Asp | Thr | Asn | Gly | |
| | | | 20 | | | | | 25 | | | | | 30 | | | |
| AAC | TTC | AAC | CCA | CTT | AAC | ACA | GTA | ACT | CGT | GCA | CAA | GCT | GCA | GAA | ATC | 144 |
| Asn | Phe | Asn | Pro | Leu | Asn | Thr | Val | Thr | Arg | Ala | Gln | Ala | Ala | Glu | Ile | |
| | | | 35 | | | | | 40 | | | | | 45 | | | |
| TTC | ACA | AAA | GCT | TTA | GAA | TTA | GAA | GCT | AAC | GGA | GAT | GTA | AAC | TTC | AAA | 192 |
| Phe | Thr | Lys | Ala | Leu | Glu | Leu | Glu | Ala | Asn | Gly | Asp | Val | Asn | Phe | Lys | |
| | | 50 | | | | | 55 | | | | | 60 | | | | |
| GAC | GTG | AAA | GCT | GGC | GCT | TGG | TAC | TAC | AAC | TCA | ATC | GCT | GCT | GTT | GTA | 240 |
| Asp | Val | Lys | Ala | Gly | Ala | Trp | Tyr | Tyr | Asn | Ser | Ile | Ala | Ala | Val | Val | |
| 65 | | | | | 70 | | | | | 75 | | | | | 80 | |
| GCT | AAC | GGC | ATT | TTT | GAA | GGT | GTT | AGT | GCA | ACT | GAA | TTT | GCA | CCA | AAC | 288 |
| Ala | Asn | Gly | Ile | Phe | Glu | Gly | Val | Ser | Ala | Thr | Glu | Phe | Ala | Pro | Asn | |
| | | | | 85 | | | | | 90 | | | | | 95 | | |
| AAA | TCT | TTA | ACT | CGT | TCT | GAA | GCT | GCT | AAA | ATT | TTA | GTA | GAA | GCA | TTC | 336 |
| Lys | Ser | Leu | Thr | Arg | Ser | Glu | Ala | Ala | Lys | Ile | Leu | Val | Glu | Ala | Phe | |
| | | | 100 | | | | | 105 | | | | | 110 | | | |
| GGT | TTA | GAA | GGT | GAA | GCA | GAT | CTT | AGC | GAA | TTT | GCT | GAC | GCT | TCT | CAA | 384 |
| Gly | Leu | Glu | Gly | Glu | Ala | Asp | Leu | Ser | Glu | Phe | Ala | Asp | Ala | Ser | Gln | |
| | | | 115 | | | | | 120 | | | | | 125 | | | |
| GTA | AAA | CCT | TGG | GCT | AAA | AAA | TAC | TTA | GAA | ATC | GCA | GTA | GCT | AAC | GGC | 432 |
| Val | Lys | Pro | Trp | Ala | Lys | Lys | Tyr | Leu | Glu | Ile | Ala | Val | Ala | Asn | Gly | |
| | | 130 | | | | | 135 | | | | | 140 | | | | |
| ATT | TTC | GAA | GGT | ACT | GAT | GCA | AAC | AAA | CTT | AAC | CCT | AAC | AAC | TCA | ATC | 480 |

```
            Ile  Phe  Glu  Gly  Thr  Asp  Ala  Asn  Lys  Leu  Asn  Pro  Asn  Asn  Ser  Ile
            145                 150                           155                      160

ACT  CGT  CAA  GAC  TTT  GCA  CTA  GTG  TTC  AAA  CGT  ACA  GTT  GAC  AAA  GTT                528
Thr  Arg  Gln  Asp  Phe  Ala  Leu  Val  Phe  Lys  Arg  Thr  Val  Asp  Lys  Val
               165                           170                      175

GAA  GGT  GAA  ACT  CCA  GAA  GAA  GCA  GCA  TTT  GTT  AAA  GCT  ATC  AAC  AAC                576
Glu  Gly  Glu  Thr  Pro  Glu  Glu  Ala  Ala  Phe  Val  Lys  Ala  Ile  Asn  Asn
               180                           185                      190

ACA  ACT  GTT  GAA  GTA  ACA  TTC  GAA  GAA  GAA  GTT  ACT  AAC  GTT  CAA  GCA                624
Thr  Thr  Val  Glu  Val  Thr  Phe  Glu  Glu  Glu  Val  Thr  Asn  Val  Gln  Ala
               195                           200                      205

CTT  AAC  TTC  AAA  ATC  GAA  GGT  TTA  GAA  ATT  AAA  AAT  GCT  TCT  GTT  AAA                672
Leu  Asn  Phe  Lys  Ile  Glu  Gly  Leu  Glu  Ile  Lys  Asn  Ala  Ser  Val  Lys
          210                      215                      220

CAA  ACA  AAC  AAA  AAA  GTT  GTT  GTA  TTA  ACT  ACT  GAA  GCT  CAA  ACA  GCT                720
Gln  Thr  Asn  Lys  Lys  Val  Val  Val  Leu  Thr  Thr  Glu  Ala  Gln  Thr  Ala
225                      230                      235                      240

GAT  AAA  GAG  TAT  GTT  TTA  ACT  CTT  GAC  GGC  GAA  ACA  ATC  GGT  GGC  TTT                768
Asp  Lys  Glu  Tyr  Val  Leu  Thr  Leu  Asp  Gly  Glu  Thr  Ile  Gly  Gly  Phe
               245                           250                      255

AAA  GGT  GTG  GCT  GCT  GTA  GTT  CCA  ACT  AAA  GTT  GAA  CTA  GTA  TCT  TCT                816
Lys  Gly  Val  Ala  Ala  Val  Val  Pro  Thr  Lys  Val  Glu  Leu  Val  Ser  Ser
               260                           265                      270

GCA  GTT  CAA  GGT  AAA  CTT  GGT  CAA  GAA  GTA  AAA  GTT  CAA  GCT  AAA  GTA                864
Ala  Val  Gln  Gly  Lys  Leu  Gly  Gln  Glu  Val  Lys  Val  Gln  Ala  Lys  Val
               275                           280                      285

ACT  GTT  GCT  GAA  GGT  CAA  TCT  AAA  GCT  GGT  ATT  CCT  GTT  ACT  TTC  ACT                912
Thr  Val  Ala  Glu  Gly  Gln  Ser  Lys  Ala  Gly  Ile  Pro  Val  Thr  Phe  Thr
               290                           295                      300

GTA  CCA  GGT  AAC  AAC  AAT  GAT  GGC  GTT  GTA  CCA  ACA  TTA  ACA  GGT  GAA                960
Val  Pro  Gly  Asn  Asn  Asn  Asp  Gly  Val  Val  Pro  Thr  Leu  Thr  Gly  Glu
315                      310                      315                      320

GCT  TTA  ACA  AAC  GAA  GAG  GGT  ATC  GCA  ACA  TAC  TCT  TAC  ACT  CGT  TAT               1008
Ala  Leu  Thr  Asn  Glu  Glu  Gly  Ile  Ala  Thr  Tyr  Ser  Tyr  Thr  Arg  Tyr
                    325                           330                      335

AAA  GAA  GGT  ACT  GAT  GAA  GTA  ACT  GCT  TAT  GCA  ACT  GGT  GAT  CGT  TCT               1056
Lys  Glu  Gly  Thr  Asp  Glu  Val  Thr  Ala  Tyr  Ala  Thr  Gly  Asp  Arg  Ser
               340                           345                      350

AAA  TTC  TCA  CTT  GGT  TAT  GTA  TTC  TGG  GGT  GTA  GAT  ACA  ATT  CTT  TCA               1104
Lys  Phe  Ser  Leu  Gly  Tyr  Val  Phe  Trp  Gly  Val  Asp  Thr  Ile  Leu  Ser
          355                           360                      365

GTT  GAA  GAA  GTA  ACT  ACA  GGT  GCT  TCA  GTT  AAT  AAT  GGT  GCA  AAC  AAA               1152
Val  Glu  Glu  Val  Thr  Thr  Gly  Ala  Ser  Val  Asn  Asn  Gly  Ala  Asn  Lys
     370                           375                      380

ACT  TAC  AAA  GTT  ACT  TAT  AAA  AAC  CCT  AAA  ACT  GGT  AAA  CCA  GAA  GCA               1200
Thr  Tyr  Lys  Val  Thr  Tyr  Lys  Asn  Pro  Lys  Thr  Gly  Lys  Pro  Glu  Ala
385                      390                      395                      400

AAC  AAA  ACA  TTT  AAT  GTT  GGT  TTT  GTA  GAA  AAC  ATG  AAT  GTT  ACT  TCT               1248
Asn  Lys  Thr  Phe  Asn  Val  Gly  Phe  Val  Glu  Asn  Met  Asn  Val  Thr  Ser
               405                           410                      415

GAT  AAA  GTA  GCA  AAT  GCT  ACA  GTT  AAT  GGC  GTA  AAA  GCA  TTA  CAA  TTA               1296
Asp  Lys  Val  Ala  Asn  Ala  Thr  Val  Asn  Gly  Val  Lys  Ala  Leu  Gln  Leu
               420                           425                      430

AGC  AAT  GGT  ACA  GCT  TTA  GAC  GCT  GCT  CAA  ATT  ACA  ACA  GAT  TCT  AAA               1344
Ser  Asn  Gly  Thr  Ala  Leu  Asp  Ala  Ala  Gln  Ile  Thr  Thr  Asp  Ser  Lys
          435                           440                      445

GGT  GAA  GCT  ACA  TTC  ACA  GTT  TCT  GGT  ACT  AAT  GCA  GCT  GTA  ACG  CCA               1392
Gly  Glu  Ala  Thr  Phe  Thr  Val  Ser  Gly  Thr  Asn  Ala  Ala  Val  Thr  Pro
450                           455                      460

GTA  GTA  TAT  GAT  CTA  CAC  AGC  ACT  AAC  AAT  AGT  ACT  TCA  AAT  AAA  AAA               1440
```

| | | | | | | | | | | | | | | | | |
|---|---|---|---|---|---|---|---|---|---|---|---|---|---|---|---|---|
| Val | Val | Tyr | Asp | Leu | His | Ser | Thr | Asn | Asn | Ser | Thr | Ser | Asn | Lys | Lys | |
| 465 | | | | 470 | | | | | 475 | | | | | 480 | | |

| TAT | AGT | GCA | TCT | GCT | TTA | CAA | ACT | ACT | GCT | TCT | AAA | GTA | ACT | TTC | GCT | 1488 |
|---|---|---|---|---|---|---|---|---|---|---|---|---|---|---|---|---|
| Tyr | Ser | Ala | Ser | Ala | Leu | Gln | Thr | Thr | Ala | Ser | Lys | Val | Thr | Phe | Ala | |
| | | | | 485 | | | | 490 | | | | | | 495 | | |

| GCT | CTT | CAA | GCA | GAG | TAT | ACA | ATT | GAG | TTA | ACT | CGT | GCT | GAT | AAT | GCT | 1536 |
|---|---|---|---|---|---|---|---|---|---|---|---|---|---|---|---|---|
| Ala | Leu | Gln | Ala | Glu | Tyr | Thr | Ile | Glu | Leu | Thr | Arg | Ala | Asp | Asn | Ala | |
| | | | 500 | | | | | 505 | | | | | 510 | | | |

| GGA | GAA | GTT | GCT | GCA | ATT | GGC | GCT | ACT | AAC | GGT | CGC | GAA | TAC | AAA | GTT | 1584 |
|---|---|---|---|---|---|---|---|---|---|---|---|---|---|---|---|---|
| Gly | Glu | Val | Ala | Ala | Ile | Gly | Ala | Thr | Asn | Gly | Arg | Glu | Tyr | Lys | Val | |
| | | 515 | | | | | 520 | | | | | 525 | | | | |

| ATT | GTA | AAA | GAT | AAA | GCT | GGT | AAC | TTA | GCT | AAA | AAT | GAA | ATC | GTT | AAT | 1632 |
|---|---|---|---|---|---|---|---|---|---|---|---|---|---|---|---|---|
| Ile | Val | Lys | Asp | Lys | Ala | Gly | Asn | Leu | Ala | Lys | Asn | Glu | Ile | Val | Asn | |
| | 530 | | | | | 535 | | | | | 540 | | | | | |

| GTT | GCA | TTC | AAT | GAA | GAT | AAA | GAT | CGT | GTA | ATT | TCA | ACA | GTT | ACA | AAT | 1680 |
|---|---|---|---|---|---|---|---|---|---|---|---|---|---|---|---|---|
| Val | Ala | Phe | Asn | Glu | Asp | Lys | Asp | Arg | Val | Ile | Ser | Thr | Val | Thr | Asn | |
| 545 | | | | | 550 | | | | | 555 | | | | | 560 | |

| GCT | AAA | TTC | GTT | GAT | ACT | GAT | CCA | GAT | ACT | GCA | GTA | TAC | TTC | ACA | GGC | 1728 |
|---|---|---|---|---|---|---|---|---|---|---|---|---|---|---|---|---|
| Ala | Lys | Phe | Val | Asp | Thr | Asp | Pro | Asp | Thr | Ala | Val | Tyr | Phe | Thr | Gly | |
| | | | | 565 | | | | | 570 | | | | | 575 | | |

| GAT | AAA | GCA | AAA | CAA | ATC | TCT | GTA | AAA | ACA | AAT | GAT | AAA | GGT | GAA | GCT | 1776 |
|---|---|---|---|---|---|---|---|---|---|---|---|---|---|---|---|---|
| Asp | Lys | Ala | Lys | Gln | Ile | Ser | Val | Lys | Thr | Asn | Asp | Lys | Gly | Glu | Ala | |
| | | | 580 | | | | | 585 | | | | | 590 | | | |

| ACA | TTT | GTT | ATC | GGT | TCT | GAT | ACA | GTA | AAC | GAT | TAT | GCA | ACA | CCA | ATT | 1824 |
|---|---|---|---|---|---|---|---|---|---|---|---|---|---|---|---|---|
| Thr | Phe | Val | Ile | Gly | Ser | Asp | Thr | Val | Asn | Asp | Tyr | Ala | Thr | Pro | Ile | |
| | | 595 | | | | | 600 | | | | | 605 | | | | |

| GCT | TGG | ATT | GAT | ATT | AAT | ACT | TCT | GAT | GCA | AAA | CAA | GGC | GAC | CTT | GAT | 1872 |
|---|---|---|---|---|---|---|---|---|---|---|---|---|---|---|---|---|
| Ala | Trp | Ile | Asp | Ile | Asn | Thr | Ser | Asp | Ala | Lys | Gln | Gly | Asp | Leu | Asp | |
| | | 610 | | | | | 615 | | | | | 620 | | | | |

| GAA | GGT | GAA | CCA | AAA | GCA | GTT | GCA | CCA | ATC | TCT | TAC | TTC | CAA | GCA | CCA | 1920 |
|---|---|---|---|---|---|---|---|---|---|---|---|---|---|---|---|---|
| Glu | Gly | Glu | Pro | Lys | Ala | Val | Ala | Pro | Ile | Ser | Tyr | Phe | Gln | Ala | Pro | |
| 625 | | | | | 630 | | | | | 635 | | | | | 640 | |

| TAT | CTT | GAT | GGC | TCA | GCT | ATC | AAA | GCA | TAC | AAA | AAA | TCA | GAT | CTT | AAT | 1968 |
|---|---|---|---|---|---|---|---|---|---|---|---|---|---|---|---|---|
| Tyr | Leu | Asp | Gly | Ser | Ala | Ile | Lys | Ala | Tyr | Lys | Lys | Ser | Asp | Leu | Asn | |
| | | | | 645 | | | | | 650 | | | | | 655 | | |

| AAA | GCT | GTA | ACT | AAG | TTT | GAT | GGT | TCT | GAA | ACT | GCA | GTA | TTT | GCA | GCA | 2016 |
|---|---|---|---|---|---|---|---|---|---|---|---|---|---|---|---|---|
| Lys | Ala | Val | Thr | Lys | Phe | Asp | Gly | Ser | Glu | Thr | Ala | Val | Phe | Ala | Ala | |
| | | | 660 | | | | | 665 | | | | | 670 | | | |

| GAA | TTA | GTA | AAC | CAA | AGC | GGC | AAA | AAA | GTA | ACT | GGT | ACT | TCT | ATT | AAG | 2064 |
|---|---|---|---|---|---|---|---|---|---|---|---|---|---|---|---|---|
| Glu | Leu | Val | Asn | Gln | Ser | Gly | Lys | Lys | Val | Thr | Gly | Thr | Ser | Ile | Lys | |
| | | 675 | | | | | 680 | | | | | 685 | | | | |

| AAA | GCA | ACT | TAT | ACA | ATC | TAC | AAT | ACT | GGT | GCT | AAT | GAT | ATT | AAA | GTA | 2112 |
|---|---|---|---|---|---|---|---|---|---|---|---|---|---|---|---|---|
| Lys | Ala | Thr | Tyr | Thr | Ile | Tyr | Asn | Thr | Gly | Ala | Asn | Asp | Ile | Lys | Val | |
| | 690 | | | | | 695 | | | | | 700 | | | | | |

| GAT | AAC | CAA | GTT | ATC | TCA | CCA | AAT | CGT | AGC | TAC | ACA | GTA | ACT | TAT | GAA | 2160 |
|---|---|---|---|---|---|---|---|---|---|---|---|---|---|---|---|---|
| Asp | Asn | Gln | Val | Ile | Ser | Pro | Asn | Arg | Ser | Tyr | Thr | Val | Thr | Tyr | Glu | |
| 705 | | | | | 710 | | | | | 715 | | | | | 720 | |

| GCT | ACT | TTA | TCT | TCT | ACA | GGA | ACT | GTT | ATT | ACA | CCT | GCT | AAG | AAT | TTA | 2208 |
|---|---|---|---|---|---|---|---|---|---|---|---|---|---|---|---|---|
| Ala | Thr | Leu | Ser | Ser | Thr | Gly | Thr | Val | Ile | Thr | Pro | Ala | Lys | Asn | Leu | |
| | | | | 725 | | | | | 730 | | | | | 735 | | |

| GAA | GTT | ACT | TCA | GTG | GAT | GGT | AAA | ACA | ACT | GCT | GTT | AAA | GTA | ATT | GCT | 2256 |
|---|---|---|---|---|---|---|---|---|---|---|---|---|---|---|---|---|
| Glu | Val | Thr | Ser | Val | Asp | Gly | Lys | Thr | Thr | Ala | Val | Lys | Val | Ile | Ala | |
| | | | 740 | | | | | 745 | | | | | 750 | | | |

| ACA | GGT | ATT | GCT | GTT | AAT | ACA | GAC | GGT | AAA | GAC | TAT | GCA | TTT | ACT | GCT | 2304 |
|---|---|---|---|---|---|---|---|---|---|---|---|---|---|---|---|---|
| Thr | Gly | Ile | Ala | Val | Asn | Thr | Asp | Gly | Lys | Asp | Tyr | Ala | Phe | Thr | Ala | |
| | | 755 | | | | | 760 | | | | | 765 | | | | |

| AAA | GAA | GCT | ACA | GCT | ACA | TTC | ACA | GCT | ACA | AAT | GAA | GTT | CCA | AAC | TCT | 2352 |
|---|---|---|---|---|---|---|---|---|---|---|---|---|---|---|---|---|
| Lys | Glu | Ala | Thr | Ala | Thr | Phe | Thr | Ala | Thr | Asn | Glu | Val | Pro | Asn | Ser | |
| | 770 | | | | | 775 | | | | | 780 | | | | | |

| TAC | ACT | GGT | GTA | GCT | ACT | CAA | TTC | AAT | ACA | GCT | GAT | TCT | GGT | TCA | AAC | 2400 |
|---|---|---|---|---|---|---|---|---|---|---|---|---|---|---|---|---|

```
Tyr  Thr  Gly  Val  Ala  Thr  Gln  Phe  Asn  Thr  Ala  Asp  Ser  Gly  Ser  Asn
785                 790                      795                      800

AGC  AAC  TCT  ATT  TGG  TTT  GCT  GGT  AAA  AAC  CCA  GTG  AAA  TAT  GCT  GGT      2448
Ser  Asn  Ser  Ile  Trp  Phe  Ala  Gly  Lys  Asn  Pro  Val  Lys  Tyr  Ala  Gly
                    805                      810                      815

GTA  TCA  GGC  AAA  ACA  TAT  AAA  TAC  TTC  GGA  GCT  AAT  GGT  AAT  GAA  GTA      2496
Val  Ser  Gly  Lys  Thr  Tyr  Lys  Tyr  Phe  Gly  Ala  Asn  Gly  Asn  Glu  Val
               820                      825                      830

TTT  GGT  GAA  GCG  GCA  TGG  GAA  GCA  TTA  TTA  ACT  CAA  TAT  GCA  ACT  GAA      2544
Phe  Gly  Glu  Ala  Ala  Trp  Glu  Ala  Leu  Leu  Thr  Gln  Tyr  Ala  Thr  Glu
          835                      840                      845

GGC  CAA  AAA  GTA  ACA  ATC  TCA  TAT  AAT  GTA  GAT  GGT  GAT  ACA  GTT  ACA      2592
Gly  Gln  Lys  Val  Thr  Ile  Ser  Tyr  Asn  Val  Asp  Gly  Asp  Thr  Val  Thr
     850                      855                      860

TTT  AAA  GTA  ATT  AGT  GCT  GTT  AAT  TCT  TCA  ACT  GAA  GCT  ATC  AAA  CCA      2640
Phe  Lys  Val  Ile  Ser  Ala  Val  Asn  Ser  Ser  Thr  Glu  Ala  Ile  Lys  Pro
865                      870                      875                      880

GTT  GCT  CCA  ACA  ACA  CCA  GCA  GCT  CCA  ACT  ACT  GGC  GCA  TTA  ACA  TTA      2688
Val  Ala  Pro  Thr  Thr  Pro  Ala  Ala  Pro  Thr  Thr  Gly  Ala  Leu  Thr  Leu
                    885                      890                      895

ACA  CCA  GCA  GCT  GGT  GGT  TTA  GTT  GAT  TTA  ACA  ACT  GCA  ACT  AAC  ACT      2736
Thr  Pro  Ala  Ala  Gly  Gly  Leu  Val  Asp  Leu  Thr  Thr  Ala  Thr  Asn  Thr
               900                      905                      910

TTA  GGA  ATT  TCA  TTA  GCT  GAT  GCA  GAT  CTT  AAT  GTA  AGT  GCA  ACA  ACT      2784
Leu  Gly  Ile  Ser  Leu  Ala  Asp  Ala  Asp  Leu  Asn  Val  Ser  Ala  Thr  Thr
          915                      920                      925

GTT  GAT  ACT  GCA  ACT  GTT  TCA  TTA  AAA  GAT  AGT  GCA  AAT  AAT  TCA  TTA      2832
Val  Asp  Thr  Ala  Thr  Val  Ser  Leu  Lys  Asp  Ser  Ala  Asn  Asn  Ser  Leu
     930                      935                      940

TCT  CTT  ACA  TTA  GTT  GAA  ACT  GGT  GCT  AAT  ACA  GGT  GTA  TTT  GCT  ACA      2880
Ser  Leu  Thr  Leu  Val  Glu  Thr  Gly  Ala  Asn  Thr  Gly  Val  Phe  Ala  Thr
945                      950                      955                      960

ACT  GTT  CAA  GCT  GGT  ACA  TTA  TCT  TCT  TTA  ACT  GCT  GGT  ACA  TTA  ACA      2928
Thr  Val  Gln  Ala  Gly  Thr  Leu  Ser  Ser  Leu  Thr  Ala  Gly  Thr  Leu  Thr
                    965                      970                      975

GTT  ACT  TAT  GCA  GAT  GCT  AAA  AAT  GCT  GCA  GGT  GTT  GCT  GAA  AAT  ATT      2976
Val  Thr  Tyr  Ala  Asp  Ala  Lys  Asn  Ala  Ala  Gly  Val  Ala  Glu  Asn  Ile
               980                      985                      990

ACT  GCT  AGC  GTA  ACA  TTA  AAG  AAA  ACT  ACT  GGA  GCA  ATT  ACT  TCT  GAT      3024
Thr  Ala  Ser  Val  Thr  Leu  Lys  Lys  Thr  Thr  Gly  Ala  Ile  Thr  Ser  Asp
          995                      1000                     1005

ACA  TTT  ACA  CAA  GGT  GTA  TTA  CCA  TCA  GCA  GCT  ACA  GCA  GCT  GAA  TAT      3072
Thr  Phe  Thr  Gln  Gly  Val  Leu  Pro  Ser  Ala  Ala  Thr  Ala  Ala  Glu  Tyr
     1010                     1015                     1020

ACT  TCT  AAA  TCA  ATT  GCT  GCA  GAT  TAT  ACA  TTT  GCA  ACA  GGT  GAA  GGA      3120
Thr  Ser  Lys  Ser  Ile  Ala  Ala  Asp  Tyr  Thr  Phe  Ala  Thr  Gly  Glu  Gly
1025                     1030                     1035                     1040

TTC  ACT  TTA  AAT  ATT  GAT  AAT  GCT  GGT  GCT  CAA  GTA  ATT  AAC  TTA  GCA      3168
Phe  Thr  Leu  Asn  Ile  Asp  Asn  Ala  Gly  Ala  Gln  Val  Ile  Asn  Leu  Ala
                    1045                     1050                     1055

GGT  AAA  AAA  GGT  GCA  CAA  GGT  GTA  GCT  GAT  GCT  ATC  AAT  GCT  ACA  TTT      3216
Gly  Lys  Lys  Gly  Ala  Gln  Gly  Val  Ala  Asp  Ala  Ile  Asn  Ala  Thr  Phe
               1060                     1065                     1070

GCA  GGT  ACT  GCA  ACT  GTT  TCT  GGA  GAC  AAA  GTA  GTT  ATT  AAA  TCA  GCT      3264
Ala  Gly  Thr  Ala  Thr  Val  Ser  Gly  Asp  Lys  Val  Val  Ile  Lys  Ser  Ala
          1075                     1080                     1085

ACA  ACA  GGT  GTT  GGT  TCT  GAA  GTT  GAA  GTT  ACA  TTC  TCT  TCT  GTT  AAT      3312
Thr  Thr  Gly  Val  Gly  Ser  Glu  Val  Glu  Val  Thr  Phe  Ser  Ser  Val  Asn
     1090                     1095                     1100

CAA  GTA  TTA  AAT  GCA  GTA  GTT  AAC  GGT  AAA  GAT  CAA  GTC  GTT  GCA  GGA      3360
```

| | | | | | | | | | | | | | | | |
|---|---|---|---|---|---|---|---|---|---|---|---|---|---|---|---|
| Gln | Val | Leu | Asn | Ala | Val | Val | Asn | Gly | Lys | Asp | Gln | Val | Val | Ala | Gly |
| 1105 | | | | 1110 | | | | 1115 | | | | 1120 | | | |

| | | | | | | | | | | | | | | | | |
|---|---|---|---|---|---|---|---|---|---|---|---|---|---|---|---|---|
| ACA | GCT | GCT | ACA | AAA | GCA | TTC | ACG | ATT | ACT | ACA | GCC | CTT | TCT | GTG | GGT | 3408 |
| Thr | Ala | Ala | Thr | Lys | Ala | Phe | Thr | Ile | Thr | Thr | Ala | Leu | Ser | Val | Gly | |
| | | | | 1125 | | | | 1130 | | | | | | 1135 | | |

| | | | | | | | | | | | | | | | | |
|---|---|---|---|---|---|---|---|---|---|---|---|---|---|---|---|---|
| GAA | AAA | GTA | GTT | ATT | GAT | GGT | GTT | GAA | TAT | ACT | GCT | GTA | GCA | TTT | GGA | 3456 |
| Glu | Lys | Val | Val | Ile | Asp | Gly | Val | Glu | Tyr | Thr | Ala | Val | Ala | Phe | Gly | |
| | | | | 1140 | | | | 1145 | | | | | | 1150 | | |

| | | | | | | | | | | | | | | | | |
|---|---|---|---|---|---|---|---|---|---|---|---|---|---|---|---|---|
| ACT | GCT | CCA | ACA | GCA | AAT | ACA | TTC | GTA | GTT | GAA | TCT | GCT | GCT | AAT | ACA | 3504 |
| Thr | Ala | Pro | Thr | Ala | Asn | Thr | Phe | Val | Val | Glu | Ser | Ala | Ala | Asn | Thr | |
| | | | 1155 | | | | | 1160 | | | | | 1165 | | | |

| | | | | | | | | | | | | | | | | |
|---|---|---|---|---|---|---|---|---|---|---|---|---|---|---|---|---|
| TTA | GCT | TCA | GTA | GCT | GAC | CAA | GCT | GCA | AAT | CTT | GCT | GCT | ACA | ATT | GAT | 3552 |
| Leu | Ala | Ser | Val | Ala | Asp | Gln | Ala | Ala | Asn | Leu | Ala | Ala | Thr | Ile | Asp | |
| | | | 1170 | | | | | 1175 | | | | | 1180 | | | |

| | | | | | | | | | | | | | | | | |
|---|---|---|---|---|---|---|---|---|---|---|---|---|---|---|---|---|
| ACT | TTA | AAC | ACT | GCA | GAT | AAG | TTT | ACA | GCT | TCT | GCA | ACA | GGT | GCT | ACT | 3600 |
| Thr | Leu | Asn | Thr | Ala | Asp | Lys | Phe | Thr | Ala | Ser | Ala | Thr | Gly | Ala | Thr | |
| 1185 | | | | | 1190 | | | | 1195 | | | | | | 1200 | |

| | | | | | | | | | | | | | | | | |
|---|---|---|---|---|---|---|---|---|---|---|---|---|---|---|---|---|
| ATT | ACA | TTA | ACT | TCT | ACT | GTA | ACA | CCA | GTA | GGT | ACT | ACA | ATT | ACT | GAA | 3648 |
| Ile | Thr | Leu | Thr | Ser | Thr | Val | Thr | Pro | Val | Gly | Thr | Thr | Ile | Thr | Glu | |
| | | | | 1205 | | | | | 1210 | | | | | 1215 | | |

| | | | | | | |
|---|---|---|---|---|---|---|
| CCA | GTA | ATT | ACA | TTA | AAA | 3666 |
| Pro | Val | Ile | Thr | Leu | Lys | |
| | | | 1220 | | | |

(2) INFORMATION FOR SEQ ID NO: 15:

(i) SEQUENCE CHARACTERISTICS:
        (A) LENGTH: 1222 amino acids
        (B) TYPE: amino acid
        (D) TOPOLOGY: linear (ii) MOLECULE TYPE: protein (xi) SEQUENCE DESCRIPTION: SEQ ID NO: 15:

| | | | | | | | | | | | | | | |
|---|---|---|---|---|---|---|---|---|---|---|---|---|---|---|
| Ala | Gln | Val | Asn | Asp | Tyr | Asn | Lys | Ile | Ser | Gly | Tyr | Ala | Lys | Glu | Ala |
| 1 | | | | 5 | | | | 10 | | | | | | 15 | |

| | | | | | | | | | | | | | | |
|---|---|---|---|---|---|---|---|---|---|---|---|---|---|---|
| Val | Gln | Ala | Leu | Val | Asp | Gln | Gly | Val | Ile | Gln | Gly | Asp | Thr | Asn | Gly |
| | | | 20 | | | | | 25 | | | | | 30 | | |

| | | | | | | | | | | | | | | |
|---|---|---|---|---|---|---|---|---|---|---|---|---|---|---|
| Asn | Phe | Asn | Pro | Leu | Asn | Thr | Val | Thr | Arg | Ala | Gln | Ala | Ala | Glu | Ile |
| | | | 35 | | | | | 40 | | | | | 45 | | |

| | | | | | | | | | | | | | | |
|---|---|---|---|---|---|---|---|---|---|---|---|---|---|---|
| Phe | Thr | Lys | Ala | Leu | Glu | Leu | Glu | Ala | Asn | Gly | Asp | Val | Asn | Phe | Lys |
| | 50 | | | | | 55 | | | | | 60 | | | | |

| | | | | | | | | | | | | | | |
|---|---|---|---|---|---|---|---|---|---|---|---|---|---|---|
| Asp | Val | Lys | Ala | Gly | Ala | Trp | Tyr | Tyr | Asn | Ser | Ile | Ala | Ala | Val | Val |
| 65 | | | | | 70 | | | | | 75 | | | | | 80 |

| | | | | | | | | | | | | | | |
|---|---|---|---|---|---|---|---|---|---|---|---|---|---|---|
| Ala | Asn | Gly | Ile | Phe | Glu | Gly | Val | Ser | Ala | Thr | Glu | Phe | Ala | Pro | Asn |
| | | | | 85 | | | | | 90 | | | | | 95 | |

| | | | | | | | | | | | | | | |
|---|---|---|---|---|---|---|---|---|---|---|---|---|---|---|
| Lys | Ser | Leu | Thr | Arg | Ser | Glu | Ala | Ala | Lys | Ile | Leu | Val | Glu | Ala | Phe |
| | | | 100 | | | | | 105 | | | | | 110 | | |

| | | | | | | | | | | | | | | |
|---|---|---|---|---|---|---|---|---|---|---|---|---|---|---|
| Gly | Leu | Glu | Gly | Glu | Ala | Asp | Leu | Ser | Glu | Phe | Ala | Asp | Ala | Ser | Gln |
| | | | 115 | | | | | 120 | | | | | 125 | | |

| | | | | | | | | | | | | | | |
|---|---|---|---|---|---|---|---|---|---|---|---|---|---|---|
| Val | Lys | Pro | Trp | Ala | Lys | Lys | Tyr | Leu | Glu | Ile | Ala | Val | Ala | Asn | Gly |
| | | 130 | | | | | 135 | | | | | 140 | | | |

| | | | | | | | | | | | | | | |
|---|---|---|---|---|---|---|---|---|---|---|---|---|---|---|
| Ile | Phe | Glu | Gly | Thr | Asp | Ala | Asn | Lys | Leu | Asn | Pro | Asn | Asn | Ser | Ile |
| 145 | | | | | 150 | | | | | 155 | | | | | 160 |

| | | | | | | | | | | | | | | |
|---|---|---|---|---|---|---|---|---|---|---|---|---|---|---|
| Thr | Arg | Gln | Asp | Phe | Ala | Leu | Val | Phe | Lys | Arg | Thr | Val | Asp | Lys | Val |
| | | | | 165 | | | | | 170 | | | | | 175 | |

| | | | | | | | | | | | | | | |
|---|---|---|---|---|---|---|---|---|---|---|---|---|---|---|
| Glu | Gly | Glu | Thr | Pro | Glu | Glu | Ala | Ala | Phe | Val | Lys | Ala | Ile | Asn | Asn |
| | | | 180 | | | | | 185 | | | | | 190 | | |

| | | | | | | | | | | | | | | |
|---|---|---|---|---|---|---|---|---|---|---|---|---|---|---|
| Thr | Thr | Val | Glu | Val | Thr | Phe | Glu | Glu | Glu | Val | Thr | Asn | Val | Gln | Ala |

|   |   |   | 195 |   |   |   | 200 |   |   |   | 205 |   |   |   |
|---|---|---|---|---|---|---|---|---|---|---|---|---|---|---|

Leu Asn Phe Lys Ile Glu Gly Leu Glu Ile Lys Asn Ala Ser Val Lys
210                     215                 220

Gln Thr Asn Lys Lys Val Val Leu Thr Thr Glu Ala Gln Thr Ala
225             230             235                 240

Asp Lys Glu Tyr Val Leu Thr Leu Asp Gly Glu Thr Ile Gly Gly Phe
                245             250                 255

Lys Gly Val Ala Ala Val Val Pro Thr Lys Val Glu Leu Val Ser Ser
            260             265             270

Ala Val Gln Gly Lys Leu Gly Gln Glu Val Lys Val Gln Ala Lys Val
        275             280             285

Thr Val Ala Glu Gly Gln Ser Lys Ala Gly Ile Pro Val Thr Phe Thr
    290             295             300

Val Pro Gly Asn Asn Asn Asp Gly Val Val Pro Thr Leu Thr Gly Glu
305             310             315                 320

Ala Leu Thr Asn Glu Gly Ile Ala Thr Tyr Ser Tyr Thr Arg Tyr
                325             330                 335

Lys Glu Gly Thr Asp Glu Val Thr Ala Tyr Ala Thr Gly Asp Arg Ser
            340             345             350

Lys Phe Ser Leu Gly Tyr Val Phe Trp Gly Val Asp Thr Ile Leu Ser
        355             360             365

Val Glu Glu Val Thr Thr Gly Ala Ser Val Asn Asn Gly Ala Asn Lys
    370             375             380

Thr Tyr Lys Val Thr Tyr Lys Asn Pro Lys Thr Gly Lys Pro Glu Ala
385             390             395             400

Asn Lys Thr Phe Asn Val Gly Phe Val Glu Asn Met Asn Val Thr Ser
            405             410             415

Asp Lys Val Ala Asn Ala Thr Val Asn Gly Val Lys Ala Leu Gln Leu
            420             425             430

Ser Asn Gly Thr Ala Leu Asp Ala Ala Gln Ile Thr Thr Asp Ser Lys
        435             440             445

Gly Glu Ala Thr Phe Thr Val Ser Gly Thr Asn Ala Ala Val Thr Pro
    450             455             460

Val Val Tyr Asp Leu His Ser Thr Asn Asn Ser Thr Ser Asn Lys Lys
465             470             475             480

Tyr Ser Ala Ser Ala Leu Gln Thr Thr Ala Ser Lys Val Thr Phe Ala
            485             490             495

Ala Leu Gln Ala Glu Tyr Thr Ile Glu Leu Thr Arg Ala Asp Asn Ala
        500             505             510

Gly Glu Val Ala Ala Ile Gly Ala Thr Asn Gly Arg Glu Tyr Lys Val
        515             520             525

Ile Val Lys Asp Lys Ala Gly Asn Leu Ala Lys Asn Glu Ile Val Asn
    530             535             540

Val Ala Phe Asn Glu Asp Lys Asp Arg Val Ile Ser Thr Val Thr Asn
545             550             555             560

Ala Lys Phe Val Asp Thr Asp Pro Asp Thr Ala Val Tyr Phe Thr Gly
            565             570             575

Asp Lys Ala Lys Gln Ile Ser Val Lys Thr Asn Asp Lys Gly Glu Ala
        580             585             590

Thr Phe Val Ile Gly Ser Asp Thr Val Asn Asp Tyr Ala Thr Pro Ile
    595             600             605

Ala Trp Ile Asp Ile Asn Thr Ser Asp Ala Lys Gln Gly Asp Leu Asp
610             615             620

```
Glu  Gly  Glu  Pro  Lys  Ala  Val  Ala  Pro  Ile  Ser  Tyr  Phe  Gln  Ala  Pro
625            630                 635                      640

Tyr  Leu  Asp  Gly  Ser  Ala  Ile  Lys  Ala  Tyr  Lys  Lys  Ser  Asp  Leu  Asn
               645                 650                      655

Lys  Ala  Val  Thr  Lys  Phe  Asp  Gly  Ser  Glu  Thr  Ala  Val  Phe  Ala  Ala
               660                 665                      670

Glu  Leu  Val  Asn  Gln  Ser  Gly  Lys  Lys  Val  Thr  Gly  Thr  Ser  Ile  Lys
               675                 680                      685

Lys  Ala  Thr  Tyr  Thr  Ile  Tyr  Asn  Thr  Gly  Ala  Asn  Asp  Ile  Lys  Val
          690                 695                 700

Asp  Asn  Gln  Val  Ile  Ser  Pro  Asn  Arg  Ser  Tyr  Thr  Val  Thr  Tyr  Glu
705                 710                 715                           720

Ala  Thr  Leu  Ser  Ser  Thr  Gly  Thr  Val  Ile  Thr  Pro  Ala  Lys  Asn  Leu
               725                 730                      735

Glu  Val  Thr  Ser  Val  Asp  Gly  Lys  Thr  Thr  Ala  Val  Lys  Val  Ile  Ala
               740                 745                      750

Thr  Gly  Ile  Ala  Val  Asn  Thr  Asp  Gly  Lys  Asp  Tyr  Ala  Phe  Thr  Ala
          755                 760                 765

Lys  Glu  Ala  Thr  Ala  Thr  Phe  Thr  Ala  Thr  Asn  Glu  Val  Pro  Asn  Ser
          770                 775                 780

Tyr  Thr  Gly  Val  Ala  Thr  Gln  Phe  Asn  Thr  Ala  Asp  Ser  Gly  Ser  Asn
785                 790                 795                           800

Ser  Asn  Ser  Ile  Trp  Phe  Ala  Gly  Lys  Asn  Pro  Val  Lys  Tyr  Ala  Gly
                    805                 810                      815

Val  Ser  Gly  Lys  Thr  Tyr  Lys  Tyr  Phe  Gly  Ala  Asn  Gly  Asn  Glu  Val
               820                 825                      830

Phe  Gly  Glu  Ala  Ala  Trp  Glu  Ala  Leu  Leu  Thr  Gln  Tyr  Ala  Thr  Glu
               835                 840                      845

Gly  Gln  Lys  Val  Thr  Ile  Ser  Tyr  Asn  Val  Asp  Gly  Asp  Thr  Val  Thr
850                 855                 860

Phe  Lys  Val  Ile  Ser  Ala  Val  Asn  Ser  Ser  Thr  Glu  Ala  Ile  Lys  Pro
865                 870                 875                           880

Val  Ala  Pro  Thr  Thr  Pro  Ala  Ala  Pro  Thr  Thr  Gly  Ala  Leu  Thr  Leu
               885                 890                      895

Thr  Pro  Ala  Ala  Gly  Gly  Leu  Val  Asp  Leu  Thr  Thr  Ala  Thr  Asn  Thr
               900                 905                      910

Leu  Gly  Ile  Ser  Leu  Ala  Asp  Ala  Asp  Leu  Asn  Val  Ser  Ala  Thr  Thr
          915                 920                 925

Val  Asp  Thr  Ala  Thr  Val  Ser  Leu  Lys  Asp  Ser  Ala  Asn  Asn  Ser  Leu
930                 935                 940

Ser  Leu  Thr  Leu  Val  Glu  Thr  Gly  Ala  Asn  Thr  Gly  Val  Phe  Ala  Thr
945                 950                 955                           960

Thr  Val  Gln  Ala  Gly  Thr  Leu  Ser  Ser  Leu  Thr  Ala  Gly  Thr  Leu  Thr
               965                 970                      975

Val  Thr  Tyr  Ala  Asp  Ala  Lys  Asn  Ala  Ala  Gly  Val  Ala  Glu  Asn  Ile
               980                 985                      990

Thr  Ala  Ser  Val  Thr  Leu  Lys  Lys  Thr  Thr  Gly  Ala  Ile  Thr  Ser  Asp
               995                 1000                     1005

Thr  Phe  Thr  Gln  Gly  Val  Leu  Pro  Ser  Ala  Ala  Thr  Ala  Ala  Glu  Tyr
     1010                1015                1020

Thr  Ser  Lys  Ser  Ile  Ala  Ala  Asp  Tyr  Thr  Phe  Ala  Thr  Gly  Glu  Gly
1025                1030                1035                          1040

Phe  Thr  Leu  Asn  Ile  Asp  Asn  Ala  Gly  Ala  Gln  Val  Ile  Asn  Leu  Ala
                    1045                1050                     1055
```

Gly Lys Lys Gly Ala Gln Gly Val Ala Asp Ala Ile Asn Ala Thr Phe
            1060                1065                1070

Ala Gly Thr Ala Thr Val Ser Gly Asp Lys Val Val Ile Lys Ser Ala
        1075                1080                1085

Thr Thr Gly Val Gly Ser Glu Val Glu Val Thr Phe Ser Ser Val Asn
    1090                1095                1100

Gln Val Leu Asn Ala Val Val Asn Gly Lys Asp Gln Val Val Ala Gly
1105                1110                1115                1120

Thr Ala Ala Thr Lys Ala Phe Thr Ile Thr Thr Ala Leu Ser Val Gly
            1125                1130                1135

Glu Lys Val Val Ile Asp Gly Val Glu Tyr Thr Ala Val Ala Phe Gly
            1140                1145                1150

Thr Ala Pro Thr Ala Asn Thr Phe Val Val Glu Ser Ala Ala Asn Thr
            1155                1160                1165

Leu Ala Ser Val Ala Asp Gln Ala Ala Asn Leu Ala Ala Thr Ile Asp
            1170                1175                1180

Thr Leu Asn Thr Ala Asp Lys Phe Thr Ala Ser Ala Thr Gly Ala Thr
1185                1190                1195                1200

Ile Thr Leu Thr Ser Thr Val Thr Pro Val Gly Thr Thr Ile Thr Glu
            1205                1210                1215

Pro Val Ile Thr Leu Lys
            1220

( 2 ) INFORMATION FOR SEQ ID NO: 16:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Bacillus sphaericus
        ( C ) INDIVIDUAL ISOLATE: P-1

( x i ) SEQUENCE DESCRIPTION: SEQ ID NO: 16:

```
GCACAAGTAA ACGACTATAA CAAAATCTCT GGATACGCTA AAGAAGCAGT TCAAGCTTTA    60

GTT                                                                  63
```

( 2 ) INFORMATION FOR SEQ ID NO: 17:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: N-terminal ( v i ) ORIGINAL SOURCE:
( A ) ORGANISM: Bacillus sphaericus
( C ) INDIVIDUAL ISOLATE: P-1

( i x ) FEATURE:
( A ) NAME/KEY: CDS
( B ) LOCATION:1..63

( x i ) SEQUENCE DESCRIPTION: SEQ ID NO: 17:

```
GCA CAA GTA AAC GAC TAT AAC AAA ATC TCT GGA TAC GCT AAA GAA GCA        48
Ala Gln Val Asn Asp Tyr Asn Lys Ile Ser Gly Tyr Ala Lys Glu Ala
 1               5                   10                  15

GTT CAA GCT TTA GTT                                                    63
Val Gln Ala Leu Val
             20
```

(2) INFORMATION FOR SEQ ID NO: 18:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 18:

```
Ala Gln Val Asn Asp Tyr Asn Lys Ile Ser Gly Tyr Ala Lys Glu Ala
 1               5                   10                  15
Val Gln Ala Leu Val
             20
```

(2) INFORMATION FOR SEQ ID NO: 19:

(i) SEQUENCE CHARACTERISTICS:
        (A) LENGTH: 198 amino acids
        (B) TYPE: amino acid
        (C) STRANDEDNESS: single
        (D) TOPOLOGY: linear (ii) MOLECULE TYPE:

(xi) SEQUENCE DESCRIPTION: SEQ ID NO: 19:

```
Met Ala Lys Gln Asn Lys Gly Arg Lys Phe Phe Ala Ala Ser Ala Thr
 1               5                   10                  15
Ala Ala Leu Val Ala Ser Ala Ile Val Pro Val Ala Ser Ala Ala Gln
             20                  25                  30
Val Asn Asp Tyr Asn Lys Ile Ser Gly Tyr Ala Lys Glu Ala Val Gln
                 35                  40                  45
Ala Leu Val Asp Gln Gly Val Ile Gln Gly Asp Thr Asn Gly Asn Phe
             50                  55                  60
Asn Pro Leu Asn Thr Val Thr Arg Ala Gln Ala Ala Glu Ile Phe Thr
 65                  70                  75                  80
Lys Ala Leu Glu Leu Glu Ala Asn Gly Asp Val Asn Phe Lys Asp Val
                 85                  90                  95
Lys Ala Gly Ala Trp Tyr Tyr Asn Ser Ile Ala Ala Val Val Ala Asn
                100                 105                 110
Gly Ile Phe Glu Gly Val Ser Ala Thr Glu Phe Ala Pro Asn Lys Ser
                115                 120                 125
Leu Thr Arg Ser Glu Ala Ala Lys Ile Leu Val Glu Ala Phe Gly Leu
                130                 135                 140
Glu Gly Glu Ala Asp Leu Ser Glu Phe Ala Asp Ala Ser Gln Val Lys
145                 150                 155                 160
Pro Trp Ala Lys Lys Tyr Leu Glu Ile Ala Val Ala Asn Gly Ile Phe
                165                 170                 175
Glu Gly Thr Asp Ala Asn Lys Leu Asn Pro Asn Asn Ser Ile Thr Arg
                180                 185                 190
Gln Asp Phe Ala Leu Val
                195
```

(2) INFORMATION FOR SEQ ID NO: 20:

( i ) SEQUENCE CHARACTERISTICS:
  ( A ) LENGTH: 200 amino acids
  ( B ) TYPE: amino acid
  ( C ) STRANDEDNESS: single
  ( D ) TOPOLOGY: linear ( i i ) MOLECULE TYPE:

( x i ) SEQUENCE DESCRIPTION: SEQ ID NO: 20:

| Met | Ala | Lys | Gln | Asn | Lys | Gly | Arg | Lys | Phe | Phe | Ala | Ala | Ser | Ala | Thr |
|---|---|---|---|---|---|---|---|---|---|---|---|---|---|---|---|
| 1 | | | | 5 | | | | | 10 | | | | | 15 | |
| Ala | Ala | Leu | Val | Ala | Ser | Ala | Ile | Val | Pro | Val | Ala | Ser | Ala | Ala | Gln |
| | | | 20 | | | | | 25 | | | | | 30 | | |
| Leu | Met | Asp | Phe | Asn | Lys | Ile | Ser | Gly | Tyr | Ala | Lys | Glu | Ala | Val | Gln |
| | | 35 | | | | | 40 | | | | | 45 | | | |
| Ser | Leu | Val | Asp | Ala | Gly | Val | Ile | Gln | Gly | Asp | Ala | Asn | Gly | Asn | Phe |
| | 50 | | | | | 55 | | | | | 60 | | | | |
| Asn | Pro | Leu | Lys | Thr | Ile | Ser | Arg | Ala | Glu | Ala | Ala | Thr | Ile | Phe | Thr |
| 65 | | | | | 70 | | | | | 75 | | | | | 80 |
| Asn | Ala | Leu | Glu | Leu | Glu | Ala | Glu | Gly | Asp | Val | Asn | Phe | Lys | Asp | Val |
| | | | | 85 | | | | | 90 | | | | | 95 | |
| Lys | Ala | Asp | Ala | Trp | Tyr | Tyr | Asp | Ala | Ile | Ala | Ala | Thr | Val | Glu | Asn |
| | | | 100 | | | | | 105 | | | | | 110 | | |
| Gly | Ile | Phe | Glu | Gly | Val | Ser | Ala | Thr | Glu | Phe | Ala | Pro | Asn | Lys | Gln |
| | | 115 | | | | | 120 | | | | | 125 | | | |
| Leu | Thr | Arg | Ser | Glu | Ala | Ala | Lys | Ile | Leu | Val | Asp | Ala | Phe | Glu | Leu |
| | | 130 | | | | | 135 | | | | | 140 | | | |
| Glu | Gly | Glu | Gly | Asp | Leu | Ser | Glu | Phe | Ala | Asp | Ala | Ser | Thr | Val | Lys |
| 145 | | | | | 150 | | | | | 155 | | | | | 160 |
| Pro | Trp | Ala | Lys | Ser | Tyr | Leu | Glu | Ile | Ala | Val | Ala | Asn | Gly | Val | Ile |
| | | | | 165 | | | | | 170 | | | | | 175 | |
| Lys | Gly | Ser | Glu | Ala | Asn | Gly | Lys | Thr | Asn | Leu | Asn | Pro | Asn | Ala | Pro |
| | | | | 180 | | | | | 185 | | | | | 190 | |
| Ile | Thr | Arg | Gln | Asp | Phe | Ala | Val | | | | | | | | |
| | | | 195 | | | | 200 | | | | | | | | |

( 2 ) INFORMATION FOR SEQ ID NO: 21:

( i ) SEQUENCE CHARACTERISTICS:
  ( A ) LENGTH: 600 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 21:

```
GAATTCGCTA AGAAACGCCT TCTATATTTC GGTTTCTTTA CAATTATAAC TAAAATATTA        60
CGGGAGTCTT TAATTTTTGA CAATTTAGTA ACCATTCCAG AAAATGCTTG GTTATTATTG       120
AGAGTAAGGT ATAATAGGTA ACGGAACTAT ATGTTACCAA TCCAAATGAG GATATAATTA       180
GTTGTAATTT TAATGGTTTC TACCAAATAC CATATTAGGT ATGGTAAAAA AATCTTCTAT       240
AACTAAATTT ATGTCCCAAT GCTTGAATTT CGGAAAAGAT AGTGTTATAT TATTGTAGAA       300
AGTGAATAAA CTTACTAGAA TGGTATTCTA CTACGCTTTT TCTAGTAAAT TTACTAACAA       360
ATTTGCTTTA GTTTTGTATT ATTCAAGAAA GCTATAATAC ATACATTTAG GTAACTAGGC       420
GGTACTATAG TTTTCGTTGG ATTAATATCA ATTTAAGGAA TTTTAGGGAG GAATACATTA       480
ATGGCAAAGC AAAACAAAGG CCGTAAGTTC TTCGCGGCAT CAGCAACAGC TGCATTAGTT       540
```

GCATCGGCAA TCGTACCTGT AGCATCTGCT GCACAAGTAA ACGACTATAA CAAAATCTCT    600

(2) INFORMATION FOR SEQ ID NO: 22:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

ATGGCAAAGC AAAACAAAGG CCGTAAGTTC TTCGCGGCAT CAGCAACAGC TGCATTAGTT    60

GCATCGGCAA TCGTACCTGT AGCATCTGCT GCACAAGTAA ACGACTATAA CAAAATCTCT    120

(2) INFORMATION FOR SEQ ID NO: 23:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

TCTAGAGGTA CCGCATGCGA TATCGAGCTC TCCCGGGAAT TCCCGGGGAT CCGGCCCATG    60

ATCATGTGGA TTGAACAAGA TGGA    84

(2) INFORMATION FOR SEQ ID NO: 24:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

TCTAGAGGTA CCGCATGCGA TATCGAGCTC TCCCGGGAAT TCCCGGGGAT CCCTCGAGGA    60

GCTTCGATGC A    71

(2) INFORMATION FOR SEQ ID NO: 25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="(synthetic
            oligodeoxynucleotide)"

(ix) FEATURE:
        (A) NAME/KEY: modified_base
        (B) LOCATION:6

(ix) FEATURE:
        (A) NAME/KEY: modified_base
        (B) LOCATION:9

(ix) FEATURE:
        (A) NAME/KEY: modified_base
        (B) LOCATION:18

(ix) FEATURE:

-continued ( A ) NAME/KEY: modified_base
( B ) LOCATION:21

( i x ) FEATURE:
( A ) NAME/KEY: modified_____se
( B ) LOCATION:24

( x i ) SEQUENCE DESCRIPTION: SEQ ID NO: 25:

GCYTGNACNG CYTCYTTNGC NTANCC 26

EXPRESSION OF SURFACE LAYER PROTEINS

This application is a national stage application of PCT/EP95/00147.

The present invention relates to vaccines and proteins, rDNA molecules encoding protein expression and presentation systems for the production and presentation of the said proteins, expression vectors therefor, and hosts transformed therewith, as well as methods involved therewith.

The traditional view on the native polymeric organization of the bacterial cell wall has changed dramatically over recent years with the development of new techniques for electron microscopic analysis. The classical idea that the cell membrane(s) is(are) covered by a peptide-glycan-containing matrix does not hold any longer. Besides additional surface structures such as capsules, sheaths, slimes or fimbriae, proteinaceous surface arrays or S-layers are being recognized as a main constituent of the bacterial cell wall (Sleytr and Messner, 1988).

S-layers are a common feature in archaebacterial surfaces (König, 1988). In some species such as *Halobacterium salinarum* or Thermoproteus spp. the proteinaceous S-layer even forms the sole cell wall. At present S-layers are being detected with increasing frequency in a large range of gram-positive and gram-negative eubacteria. Surface arrays are composed of protein or glycoprotein subunits that are arranged into a paracrystalline two-dimensional array, displaying hexagonal, tetragonal or oblique symmetry. Self-assembly of the S-layer is an inherent property of the subunit and is the result of non-covalent protein-protein interactions mediated through salt bridging by divalent metal cations ($Mg^{2+}$ or $Ca^{2+}$). Non-covalent interactions with components of the underlying cell envelope are thought to be responsible for its positioning at the outermost surface.

Despite the cloning and the characterization of several genes encoding S-layer proteins (SLP's), their function still remains speculative. A variety of functions have been attributed to surface arrays. They might serve as a protective barrier against degradative enzymes or predators, such as Bdellovibrio or help in maintaining bacterial cell shape and form. In some bacterial pathogens, S-layers have been identified as important virulence factors. Although S-layers have several physical features in common, general conclusions on their function cannot yet been drawn.

SLP's are thus present in a large number of archaebacteria, as well as gram-positive and, to a lesser extent, gram-negative bacteria. SLP's form a main constituent of the cell wall, being capable of self-assembly into arrays (crystalline arrays) at the outermost surface of the cell wall. SLP's are continuously and spontaneously produced in larger amounts than any other class of protein in the cell.

SLP's are expressed and either presented or secreted by systems therefor within cells. The genes of these SLP system(s) include: strong promoter sequence(s), a signal peptide coding sequence which is located downstream of the promoter sequence(s), a SLP coding sequence and a transcription termination sequence. The SLP coding sequence is located downstream from the signal peptide coding sequence, having its 5'-terminus operatively linked to the 3'-terminus of the signal peptide coding sequence.

As described herein, an SLP presentation system is distinguished from an SLP secretion system. In the former, the SLP's are bound-up in the cell wall of a host where they are thus presented. In the latter, the SLP's are either produced in the cytoplasm (intracellular production) or secreted into the surrounding medium (extracellular secretion).

The SLP expression and secretion systems of several bacteria have been well-characterized. Among these are those SLP expression and secretion systems of bacteria of the genus Bacillus. Bacilli are well-known as abundant producers of SLP's.

More particularly, the SLP expression and secretion system of the species *Bacillus brevis* has been extensively studied for its potential use in expressing and extracellularly secreting large quantities of predetermined proteins. *B. brevis* is able to secrete large amounts of extracellular SLP which are used to aid translocation of the predetermined protein across *B. brevis*'s unique two-layer cell wall for extracellular secretion thereof. Also, *B. brevis* does not secrete extracellular proteases in quantities which may degrade and inactivate the extracellularly-produced proteins.

Tsukagoshi et al (1985) discloses the fusion of the α-amylase gene of *Bacillus stearothermophilius* DY-5 to the SLP coding gene of *B. brevis* 47-5 for the expression of α-amylase in *B. stearothermophilius* DY-5, *B. brevis* 47-5, *Escherichia coli* HB101 and *Bacillus subtilis* 1A289 hosts that are transformed therewith. Comparison studies showed that the *B. brevis* secretion levels were one hundred (100) times higher than that of *B. stearothermophilius* itself. *B. brevis* secretion levels were fifteen (15) times higher than those of *E. coli* and five (5) times higher than those of *B. subtilis*. The efficient secretion of the enzyme in *B. brevis* is suggested therein as being due to the unique properties of the cell wall of the *B. brevis*.

Yamagata et al (1987) discloses the translational fusion of the 5'-region of the gene coding for the middle wall protein (a SLP particular to *B. brevis*) of *B. brevis* 47 with the α-amylase gene of *Bacillus licheniformis* for expression in *B. brevis* 47. The translational fusion of these genes is reported as achieving efficient levels of α-amylase production in *B. brevis* 47.

Tsukagoshi (1987/8) discloses the translational fusion of the gene coding for swine pepsinogen with the 5'-region of the middle wall protein gene of *B. brevis* for expression in *B. brevis* 47 and *B. brevis* HPD31. Translational fusion of the 5'-region to the CGTase gene of *Bacillus macerans* also resulted in the expression of the efficient levels of CGTase in *B. brevis* 47.

EP-A-0257189 in the name of Higeta Shoyu Co., Ltd., et al., discloses a series of *B. brevis* strains which may be utilised as hosts to produce large amounts of proteins without producing deleterious amounts of extracellular proteases.

GB-A-2182664 in the name of Udaka discloses "expressing genes" that are derived from *B. brevis* 47 and which may be fused to genes coding for heterologous proteins. Among the heterologous genes suggested as being appropriate for being fused to the genes derived from *B. brevis* 47 are various eucaryotic genes (such as those genes coding for interferon and insulin) as well as procaryotic genes (such as those genes coding for tryptophanase and aspartate ammonia lyase). The fused genes may then be incorporated into expression vectors for transforming *B. brevis* 47.

Adachi et al (1989) discloses the fusion of the co-transcriptional cell wall protein (cwp) gene operon (coding for both the middle wall protein and the outer wall protein) of *B. brevis* 47 with the gene coding for α-amylase in *B. licheniformis* in order to provide extracellular production of *B licheniformis* α-amylase by *B. brevis* 47 and *B. subtilis* IA289. The presence of several different cwp operon transcripts and the presence of at least three different promoters (referred as therein as the P1, P2 and P3 promoters) were confirmed. It was reported that the P1 and P3 promoters were used in the same extent in *B. brevis* and *B. subtilis,* whereas the P2 promoter was reported to be used much less frequently in *B. subtilis* than in *B. brevis.*

Takao et al (1989) discloses an expression-secretion vector for transforming *B. brevis* hosts for producing heterologous proteins, including eucaryotic proteins, such as swine pepinsogen. The vector utilizes the promoter, the signal-peptide coding sequences and nine (9) aminoterminal amino acids of a middle wall protein of *B. brevis* which are fused to a heterologous protein coding sequence. The hosts transformed thereby are *B. brevis* 47 and HPD31.

Yamagata et al (1989) discloses a host-vector system utilizing strains (47 and HPD31) of *B. brevis* that hyperproduce SLP's as the hosts. Expression-secretion vectors are constructed from multiple promoters, the peptide-signal coding region and a structural gene for one of the major cell wall proteins of *B. brevis* 47. The *B. brevis* 47 genes were fused to a synthetic gene coding for human epidermal growth factor (hEGF).

In addition to the use of SLP expression and secretion systems derived from *B. brevis* in *B. brevis,* it has also been disclosed to utilize SLP expression and secretion systems of *B. brevis* in *B. subtilis* hosts. Tsuboi et al (1989) discloses the transformation of *B. subtilis* with genes from *B. brevis* 47 that code for middle wall proteins. The transformed *B. subtilis* is thus capable of expressing the middle wall protein of *B. brevis.*

It has also been disclosed by Tang et al (1989) that the SLP expression and secretion system of an alkaline phosphatase secretion-deficient mutant strain (strain NM 105) of *B. licheniformis* 749/C can be cloned into mutant strains of both *E. coli* (strain NM 539) and *B. subtilis* (strain MI112). Bowditch et al 1989 discloses cloning the gene coding for the SLP of *B. sphaerius* into *E. coli* TB1, JM101 and JM107. The transformed *E. coli* hosts then expressed the *B. sphaericus* SLP.

Lucas et al (1994), while studying the S-layer protein of Acetogenium kivui, disclose that there exists a repeated peptide sequence at the N-terminus of said S-layer protein which is shared by several different S-layer proteins, such as the middle wall protein from *B. brevis* and the S-layer protein form *B. sphaericus* 2362, and these authors suggest that this conserved domain is essential to anchor these S-layer proteins to the underlying peptidoglucan. Interestingly, Matuschek et al. (1994) disclose that the same conserved domain, which is found at the N-terminus of the Acetogenium kivui S-layer, is also present in the sequence of the extracellular, cell-bound pullulanase from *Thermoanaerobacterium thermosulfurigenes,* but in the latter case it is located near the C-terminus of the polypeptide.

U.S. Pat. No. 5,043,158 discloses pharmaceutical compositions which comprise carriers that are chemically-coupled to epitope-bearing moieties. The carriers are isolated crystalline or paracrystalline glycoproteins, especially those derived from the SLP's of *Clostridium thermohydrosulfuricum* and *B. stearothermophilus.* The conjugates formed thereby were reported as being capable of eliciting the formation of antibodies as well as eliciting B-cell mediated and T-cell mediated responses.

It is a primary objective of the present invention to provide a recombinant DNA (rDNA) molecule that includes a SLP system capable of expressing and presenting, rather than expressing and secreting, a fusion polypeptide (such as a fused SLP/antigenic peptide) in a wide variety of bacteria including bacteria of the genus Bacillus and, more particularly, *B. sphaericus.*

It is yet another primary object of the present invention to provide such a rDNA molecule which includes, derived from *B. sphaericus,* SLP promoter sequence(s), a SLP signal-peptide coding sequence and a SLP coding sequence which codes for at least a functional portion of the surface layer protein of *B. sphaericus* and which may be fused to a heterologous coding sequence coding for a heterologous polypeptide (such as an antigenic peptide), such that the expression of the heterologous polypeptide is placed under the control of the said promoter(s) and further such that the heterologous polypeptide expressed thereby will be fused to the SLP so as to be bound-up in the cell wall of the host for presentation thereof on the outer surface of the host's cell wall for eliciting an immunogenic response thereto.

It is a yet further primary object of the present invention to provide vectors containing such rDNA molecules, which vectors may be used to effectively transform host cells.

It is a still yet further primary object of the present invention to provide hosts, especially hosts of the genus Bacillus, and more particularly of the species *B. sphaericus,* which are transformed with vectors containing such rDNA molecules, which express fusion polypeptides (such as antigenic peptides) produced thereby and which present the expressed fusion polypeptides for, inter alia, eliciting an immunogenic response thereto.

A still further primary object of the present invention is to provide methods for forming the rDNA molecules, for preparing the appropriate vectors therefor, for transforming hosts with such vectors and for producing the fusion peptides (vaccines and proteins) of the present invention.

The present invention provides a host cell which is provided with a S-layer comprising a fusion polypeptide consisting essentially of:

(a) at least sufficient of a SLP for a S-layer composed thereof to assemble, and (b) a heterologous polypeptide which is fused to either the carboxy terminus of (a) or the amino terminus of (a) and which is thereby presented on the outer surface of the said cell.

Preferably, the heterologous polypeptide is fused to the carboxy terminus of (a).

The amount of a SLP which is sufficient in its own right for a S-layer composed thereof to form is termed herein the "functional portion" of the SLP. The fusion polypeptide thus typically incorporates at least the functional portion of a SLP native to the host cell. Sacculi derived from a host cell according to the invention also form part of the invention.

The heterologous polypeptide may be an antigenic peptide. In that event, the invention provides a vaccine comprising a host cell or sacculi according to the invention wherein the heterologous polypeptide is an antigenic peptide and a pharmaceutically or veterinarily acceptable carrier or diluent.

The invention further provides a recombinant DNA molecule which comprises a promoter operably linked to a coding sequence which encodes a signal peptide and a fusion polypeptide, the signal peptide being capable of directing the said fusion polypeptide to be presented on the surface of a host cell in which expression occurs and the fusion polypeptide consisting essentially of a heterologous polypeptide fused to either the carboxy terminus or to the amino terminus of at least sufficient of a SLP for a S-layer composed thereof to assemble.

An efficient and reliable system which employs an SLP expression and presentation system is therefore provided for the expression and presentation of fusion polypeptides (such as antigenic peptides for vaccines) in a wide variety of, preferably, Bacilli. This system includes a recombinant DNA molecule having a promoter that is fused to a functional DNA sequence, so that the functional DNA sequence is placed under the control of the promoter. The functional DNA sequence includes a SLP coding sequence which codes for at least a functional portion of a SLP. The functional DNA sequence further includes a heterologous polypeptide coding sequence that codes for a heterologous polypeptide (such as an antigenic peptide for use as a vaccine or a protein) which peptide coding sequence is fused to the SLP coding sequence.

As used herein, the term "functional DNA sequence" refers to DNA sequences that contain all of the various sequences (with the exception of the promoter sequence), both coding (such as sequences coding for the proteins whose expression and presentation is desired) and non-coding (such as control sequences and regulatory regions, i.e. sequences that are necessary or desirable for the transcription and translation of a coding sequence to which they are operably linked or fused when they are compatible with the host into which they are placed) which, when operably joined (by linking, fusing or otherwise) to a promoter and placed into a compatible host, permit the sequence to be operational and express and present the protein(s) coded for by the coding sequence(s) thereof.

As used herein, the terms "presented", "presentation", "present" and/or "presents" refer to the manner in which the heterologous polypeptide (for example an antigenic peptide or protein) is positioned when provided as part of a hybrid particle (such as the fusion vaccine or fusion protein) in such a way as to elicit an immune response to the heterologous polypeptide.

"Presentation systems" are DNA sequences which include both a coding sequence coding for a polypeptide (such as a heterologous polypeptide) whose presentation is desired, and other appropriate sequences therefore which permit such presentation when the DNA sequences are compatible with the host into which they are placed.

"Expressions systems" are DNA sequences which include both a coding sequence coding for polypeptide(s) whose expression is desired and appropriate control sequences therefor which permits such expression when the DNA sequences are compatible with the host into which they are placed. As is generally understood, "control sequences" refers to DNA segments which are required for, or which regulate, expression of the coding sequence with which they are operably joined.

We have found that it is the amino-terminal portion of a SLP which is sufficient for S-layer formation. We have found that more than the first 19.56% by number of the amino acid residues, as measured from the amino-terminus of a mature SLP, are required for a S-layer to form. By a "mature SLP" we mean a SLP without signal peptide residues. More than the N-terminal 239 amino acid residues of the mature SLP shown in FIG. 6 are thus required. The first 41.41% by number of the amino acid residues of a mature SLP are sufficient, for example the first 506 amino acid residues of the mature SLP shown in FIG. 6.

More than the first 20% amino acid residues of an active SLP may be present. The SLP portion of a fusion polypeptide may therefore consist of the first N-terminal 28% or more or 35% or more, for example the most N- terminal 41% or more or 50% or more or 60% or more or 80% or more, or even all, amino acid residues of a mature SLP such as the mature SLP shown in FIG. 6. From the first N-terminal 28% to all, for example from the first N-terminal 35% or 41% or 50% or 60% or 80% to all, of the amino acid residues of a mature SLP can be present. The first N-terminal 400 or more, 600 or more, 800 or more or 1000 or more amino acid residues of a mature SLP may be present. A convenient restriction site in the DNA coding sequence of a SLP will typically determine the C-terminus of the SLP portion of a fusion polypeptide.

The SLP portion of a fusion polypeptide is typically homologous with respect to the host cell in which the fusion polypeptide is expressed. In other words, the portion of the SLP which is present in the fusion polypeptide should generally be from a SLP of the same species as the host in which the fusion polypeptide is expressed. Typically the portion of the SLP in the fusion polypeptide is from the native SLP of the host in which the fusion polypeptide is expressed. The fusion polypeptide may incorporate an appropriate portion of a SLP of a bacterium of the genus Bacillus, for example of the species *B. brevis* or *B. sphaericus*.

The heterologous polypeptide may be a physiologically active polypeptide or a foreign epitope (an antigenic determinant, peptide immunogen or epitope-bearing moiety, as shall be discussed at greater length below). The carboxy terminus of the functional portion of a SLP may be fused directly to the amino terminus of the physiologically active polypeptide or the foreign epitope. The fusion polypeptide therefore may consist essentially of the functional portion of a SLP and, fused directly to the carboxy terminus thereof, a heterologous amino acid sequence. Alternatively, the amino terminus of the functional portion of a SLP may be fused directly to the carboxy terminus of the physiologically active polypeptide or the foreign epitope. The fusion polypeptide therefore may consist essentially of the functional portion of a SLP and, fused directly to the amino terminus thereof, a heterologous amino acid sequence.

Alternatively, an intervening linker sequence may be present between the functional portion of the SLP and the heterologous polypeptide. The linker sequence may be from 1 to 20, for example, from 1 to 5 or from 1 to 10 amino acid residues long. The linker sequence may be designed to incorporate a cleavage site recognized by cyanogen bromide or a cleavage enzyme.

The heterologous polypeptide is a polypeptide whose expression is not normally controlled by a SLP promoter i.e. is not a naturally occurring SLP. The heterologous polypeptide can be a physiologically active polypeptide such as an enzyme. The polypeptide may be a polypeptide drug or a cytokine. Specific polypeptides which may be mentioned are α-amylase, tissue plasminogen activator, luteinizing hormone releasing hormone, a growth hormone such as human growth hormone, insulin, erythropoietin, an interferon such as α-interferon, and calcitonin.

Alternatively, the heterologous polypeptide may comprise a foreign epitope or polypeptide immunogen. The polypeptide immunogen therefore typically comprises an antigenic determinant of a pathogenic organism. The immunogen can be an antigen of a pathogen. The pathogen may be a virus, bacterium, fungus, yeast or parasite. The foreign epitope may be an epitope capable of inducing neutralizing or non-neutralizing antibody or of inducing a cellular immune response.

The immunogen or epitope may be derived from a virus such as a human immunodeficiency virus (HIV) such as HIV-1 or HIV-2; a hepatitis virus such as hepatitis A, B or C; a poliovirus such as poliovirus type 1, 2 or 3; influenza virus; rabies virus; or measles virus. Examples of bacteria from which an immunogen or epitope may be derived include *B. pertussis, C. tetani, V. cholera, N. meningitides, N. gonorrhoea, C. trachomatis* and *E. coli*. The immunogen may therefore be the P69 antigen of *B. pertussis,* pertussis toxin or a subunit thereof, tetanus toxin fragment C, *E. coli* heat labile toxin B subunit (LT-B) or an *E. coli* K88 antigen, or an antigenic portion thereof. An immunogen derived from a parasite may be an immunogen derived from *P. falciparum,* a causative agent of malaria.

As used herein, the terms "antigenic peptide", "antigenic determinant", "peptide immunogen", "polypeptide immunogen", "epitope" and "epitope-bearing moiety" all refer to substances that contain a specific determinant which induces an immune response (such as the production of antibodies or the elicitation of T-cell mediated response). The substance may itself be a hapten (i.e. a simple moiety which, when rendered immunogenic, behaves as an antigen) or it may be a more complex moiety, only portions of which are responsible for immunospecificity with regard to the antibodies obtained.

As used herein, the terms "immunogenic response" and "immune response" refer to the biological responses, such as the raising of antibodies or the elicitation of T-cell or B-cell mediated responses, that are elicited in an organism (such as a mammal) by the presence of an antigen or immunogen.

The present invention also provides recombinant DNA vectors comprising a recombinant DNA molecule according to the present invention and further provides a host cell transformed with such a recombinant DNA vector. The vector is typically an expression vector. The fusion polypeptide can thereby be expressed in a suitable host cell transformed with such an expression vector. A S-layer composed of the fusion polypeptide that is expressed can thereby be assembled on the surface of the host cell.

An expression vector can include any suitable origin of replication which will enable the vector to replicate in a bacterium. A ribosome binding site is provided. The ribosome binding site is suitably located between the promoter and the DNA sequence encoding the heterologous polypeptide. If desired, a selectable marker gene such as an antibiotic resistance gene can be provided in the vector. The vector is generally a plasmid.

The vector is normally provided with a transcriptional termination sequence. The coding sequences of the recombinant DNA molecules and vectors of the invention are provided with translational start and stop codons. Vectors may be constructed by assembling all appropriate elements using techniques known in the art (Sambrook et al. 1989).

According to the invention, a host cell provided with a S-layer comprising a fusion polypeptide is prepared by a process which comprises:
(i) providing a suitable host cell incorporating a recombinant DNA molecule which comprises a promoter operably linked to a coding sequence which encodes a signal peptide and a fusion polypeptide, the signal peptide being capable of directing the said fusion polypeptide to be presented on the surface of the said host cell and the fusion polypeptide consisting essentially of a heterologous polypeptide fused to either the carboxy terminus or the amino terminus of at least sufficient of portion of a S-layer protein for a S-layer composed thereof to assemble on the surface of the said host cell; and
(ii) culturing the said host cell so that the said fusion polypeptide is expressed and a S-layer comprising the fusion polypeptide is formed on the surface of the said host cell, the heterologous polypeptide thereby being presented on the outer surface of the said host cell.

In a preferred variant of the invention, a host cell provided with a S-layer comprising a fusion polypeptide is prepared by a process which comprises:
(i) providing a suitable host cell incorporating a recombinant DNA molecule which comprises a promoter operably linked to a coding sequence which encodes a signal peptide and a fusion polypeptide, the signal peptide being capable of directing the said fusion polypeptide to be presented on the surface of the said host cell and the fusion polypeptide consisting essentially of a heterologous polypeptide fused to the carboxy terminus of at least sufficient of the amino terminal portion of a S-layer protein for a S-layer composed thereof to assemble on the surface of the said host cell; and
(ii) culturing the said host cell so that the said fusion polypeptide is expressed and a S-layer comprising the fusion polypeptide is formed on the surface of the said host cell, the heterologous polypeptide thereby being presented on the outer surface of the said host cell.

Preferably the host cell is one which does not secrete extracellular proteases. The host cell is generally a bacterium, typically a bacterium which naturally produces a S-layer protein, i.e. a bacterium which in its native state has a S-layer on its surface. Depending upon the intended use, the bacterium may be a gram-positive or gram-negative bacterium. Host bacteria include bacteria of the genera Cocci and Bacilli may be transformed, for example Staphylococcus, Streptococcus, Corynebacterium, Lactobacillus, Bacillus, Clostridium and Listeria. Preferably, host bacteria include bacteria of the genera Bacilli. Useful bacteria in which the present invention may be applied are therefore *Bacillus sphaericus* and *B. brevis*.

*Bacillus sphaericus* is a bacterium of the genus Bacillus in which a substantial quantity of the SLP's produced thereby are bound-up in the S-layer of the cell wall thereof and are not secreted extracellularly. As such, unlike *B. brevis* and *B. subtilis,* we have found that *B. sphaericus* possesses what is potentially an efficient SLP presentation system.

The structure and properties of *B. sphaericus* have been characterized (see, for example Lewis et al (1987); Howard et al (1973) and Lepault et al (1986)). *B. sphaericus* (like the other Bacilli) has a high level of growth throughout its growth cycle, thereby increasing the quantities of the fusion polypeptide that can be expressed and presented thereby.

A preferred strain of *B. sphaericus* is *B. sphaericus* P-1. *B. sphaericus* P-1 has been deposited under the Budapest Treaty of the Belgian Coordinated Collections of Microorganisms (BCCM), LMG Culture Collection, Universiteit Gent, Lab. voor Microbiologie, K.L. Ledeganckstraat 35, B-9000 Gent, Belgium. The deposit was made on 13th May 1993 and was given accession number LMG P-13855. *B. sphaericus* P-1 offers the further advantage of not producing detectable levels of extracellular proteases which can cause damage to fusing polypeptides produced according to the invention.

The signal peptide is typically a signal peptide for a SLP, for example for a SLP of a bacterium of the genus Bacillus. It may be a signal peptide for a SLP of *B. brevis, B. sphaericus* or *B. subtilis* for example *B. sphaericus* P-1. Preferably the signal peptide is the signal peptide for the SLP of which an appropriate portion is incorporated in the fusion polypeptide. A signal peptide which is homologous, i.e. which is derived from the same species of cell, with respect to the host cell in which expression of the fusion polypeptide is to occur can be employed. Preferably the native signal peptide for the native SLP of the host cell in which expression is to occur is provided.

A useful process for preparing a host cell provided with a S-layer comprising a fusion polypeptide comprises:
(a) providing an intermediate vector in which the coding sequence for an internal portion of the native SLP of the said host cell has translationally fused to the 3'-end thereof the coding sequence for the heterologous polypeptide and in which the said coding sequences are provided upstream of a promotorless selectable marker gene such that they form a translational or transcriptional fusion therewith;

(b) transforming the said host cell with the intermediate vector;

(c) selecting a transformed host cell which has a S-layer comprising the said fusion polypeptide.

This process relies upon the occurrence of a single homologous recombination as a result of the introduction of the intermediate vector into the host cell. The intermediate vector is typically a plasmid. An internal portion of the native SLP lacks the amino-terminal and carboxy-terminal amino acid residues of the native SLP. Up to the first 50, up to the first 100, up to the first 200, up to the first 300, up to the first 400 or up to the first 500 of the amino-terminal amino acid residues may be missing. Independently up to the first 50, up to the first 100, up to the first 200, up to the first 300, up to the first 400 or up to the first 500 carboxy-terminal amino acid residues may be missing.

The coding sequence for an internal portion of the native SLP therefore corresponds to the native SLP gene lacking its 5'- and 3'-ends. This coding sequence can be fused directly or via a sequence encoding a linker to the 5'- end of the coding sequence for the heterologous peptide. Suitable linkers are described above. The promoterless selectable marker gene may be the neomycin phosphotransferase II (nptII) gene which confers resistance to the antibiotics neomycin and kanamycin. The intermediate vector typically also comprises an origin of replication and a second selectable marker gene, for example an antibiotic resistance gene such as an erythromycin resistance gene.

In one preferred embodiment, therefore, a host cell having a S-layer comprising a fusion polypeptide can be prepared by the following procedure:

1. An appropriate intermediate vector is constructed that has following characteristics:
    the cloned part of the SLP in the vector has to be internal to the SLP gene, i.e. contain no borders of the gene;
    the cloned part of the SLP gene is translationally fused to the sequence encoding the heterologous peptide of interest;
    both are cloned upstream of a promotorless first selectable marker gene (e.g. the nptII gene) so that they make a translational or transcriptional fusion;
    optionally a replicon (such as that of pIL253 for *B. sphaericus*) and/or a second selectable marker gene (such as the erythromycin (Em) resistance gene).
2. The intermediate vector is introduced into an appropriate host cell such as *B. sphaericus* P-1, for example via electroporation.
3. Transformants are selected by means of the second selectable marker, for example Em resistant transformants selected. This can enable the structure of the intermediate vector to be verified.
4. The selected transformant(s) are grown, for example overnight in LB medium containing 10 $\mu$g/ml Em.
5. The transformants thus grown are plated out. For example a bacterial suspension can be plated out directly on LB+ agar containing 5–10 $\mu$g/ml neomycin (Nm) when the first selectable marker gene is the nptII gene or dilute starter culture in LB liquid medium containing the same amount of Nm, again when the first selectable marker gene is the nptII gene.
6. Colonies are selected by means of the first selectable marker, for example single Nm resistant colonies.
7. Occurrence of a single homologous recombination is verified, for example by Southern analysis.
8. Formation of the recombinant fusion polypeptide is verified, for example by sodium dodecyl sulphate-polyacrylamide gel electrophoresis (SDS-PAGE).

Alternatively, a host cell provided with a S-layer comprising a fusion polypeptide can be produced by a process comprising:

(a) fusing to a promoter a SLP coding sequence coding for the signal peptide and at least sufficient of the amino-terminal portion of a SLP for a S-layer composed thereof to assemble on the surface of the host cell, and fusing a peptide coding sequence coding for the heterologous polypeptide to the 3'-end of the SLP coding sequence, whereby a recombinant DNA molecule for the expression and presentation of the fusion polypeptide is prepared;

(b) inserting the recombinant DNA molecule into a suitable vector, whereby a recombinant DNA vector is prepared;

(c) transforming a suitable host cell with the recombinant DNA vector, whereby a transformed host cell having the recombinant DNA molecule is provided;

(d) culturing the transformed host cell, whereby the fusion polypeptide is expressed and a S-layer comprising the fusion polypeptide is assembled on the host cell wall.

The transformed host cell is thus cultured in an appropriate culture medium. As a result of expression and presentation of the fusion polypeptide on the outer surface of the host cell, the heterologous polypeptide is thus presented so that an immunogenic response can be stimulated thereto when the host cell is administered to a human or animal host. The S-layer will also comprise the host cell's native SLP unless steps are taken to disable production of that SLP.

DNA sequences consisting essentially of the appropriate coding sequences may be produced by ligation. The DNA sequences may be isolated and/or purified for use in the invention. Expression vectors can thus be prepared which incorporate a promoter operably linked to one of these DNA sequences. These vectors are capable of expressing the fusion polypeptide when provided in a suitable host. The vectors are generally plasmids.

The coding sequences are located between translation start and stop signals. A ribosome binding site, an origin of replication and, optionally, a selectable marker gene such as an antibiotic resistance gene are typically present. In addition to the promoter, other appropriate transcriptional control elements are provided, in particular a transcriptional termination site. The promoter may be the natural promoter for a SLP protein such as a promoter for a Bacillus SLP, for example for a SLP from *B. sphaericus* or *B. brevis.* Typically the promoter is the native promoter for the SLP at least the functional portion of which is present in a fusion polypeptide according to the invention. The coding sequences are provided in the correct frame such as to enable expression of the fusion polypeptide to occur in a host compatible with the vector.

Transformation of a host cell may be achieved by conventional methodologies. We have found, however, that such methodologies do not work in the case of *B. sphaericus* P-1. We have devised a new technique for transforming *B. sphaericus* P-1. Accordingly, the present invention provides a process of transforming *B. sphaericus* P-1 cells with DNA, which process comprises harvesting *B. sphaericus* P-1 cells at the late stationary growth phase, mixing the harvested cells with the DNA and effecting electroporation to cause entry of the DNA into the said cells.

Electroporation at the late stationary phase may be effected at from 8 to 16 kV/cm, 150 to 250 Ω and 20 to 40

μF. Preferred conditions are 12kV/cm, 200 Ω and 25 μF. Electroporation is generally carried out in electrocurvettes, for example 0.1 cm- or 0.2 cm-gapped electrocurvettes.

The transformed host cells are cultured under such conditions that expression of the fusion polypeptide occurs. The invention consequently additionally provides a host cell transformed with a recombinant DNA molecule, typically a vector, according to the invention.

The host cell can be transformed so that none of the native SLP is still produced or so that the native SLP is produced in addition to the fusion polypeptide according to the invention. The invention therefore further provides a host cell which is able to express a fusion polypeptide according to the invention in addition to or instead of he SLP native to the said host cell.

A host cell can therefore be engineered which presents a foreign epitope on its surface as a part of a composite S-layer. The S-layer incorporates the fusion polypeptide. The fusion polypeptide (for example, presenting a foreign epitope) and any native SLP produced by the host cell assemble into a S-layer. We have surprisingly found that fusion of a foreign amino acid sequence to at least a functional portion of a S-layer protein does not prevent the proper folding of the foreign sequence. The foreign sequence is thus presented on the surface of host cell and can be recognised by the immune system of a host, human or animal.

The foreign sequence can also be presented on the surface of sacculi. Sacculi, sometimes termed native sacculi or ghosts, are devoid of cytosolic and membrane proteins. They consist mainly of the peptido-glycan outer layer of bacterial cells surrounded by the S-layer. They can be derived from host cells according to the invention by simple procedures (Sáara and Sleytr, 1987). For example, host cells may be sonicated, a detergent such as Triton X-100 added and the mixture incubated. After washing, the treated cells can then be incubated with DNAse and RNAse. The resulting sacculi are washed again.

The host cell or sacculi derived therefrom can therefore be used as a vaccine. The host cell may be a non-pathogenic bacterium. It may be a bacterium which is naturally non-pathogenic or it may be an attenuated bacterium for this purpose, i.e. an attenuated form of a pathogenic bacterium. An attenuated bacterium typically contains one or more rationally directed mutations that prevent extensive spreading of the bacterium within the host to which the bacterium is administered. The bacterium can however still establish a limited infection leading to the stimulation of a natural immune response (Charles and Dougan, 1990).

A pharmaceutical or veterinary composition may therefore be provided which comprises a host cell provided with a S-layer comprising a fusion polypeptide according to the invention and a pharmaceutically or veterinarily acceptable carrier or diluent. The composition may be formulated as a vaccine. The composition may be administered orally, intranasally or parenterally such as subcutaneously or intramuscularly. The dosage employed depends on a number of factors including the purpose of administration and the condition of the patient. When the host cell is a bacterium, typically however a dose of from $10^9$ to $10^{11}$ bacteria is suitable for a human or animal for each route of administration.

The composition may be in lyophilized form. The composition may be formulated in capsular form. The capsules may have an enteric coating for oral administration, comprising for example Eudragate "S", Eudragate "L", cellulose acetate, cellulose phthalate or hydroxypropylmethyl cellulose. These capsules may be used as such or alternatively, the lyophilised material may be reconstituted prior to administration, e.g. as a suspension. Reconstitution is advantageously effected in a buffer at a suitable pH to ensure the viability of the organisms. In order to protect the bacteria from gastric acidity, a sodium bicarbonate preparation is advantageously administered before each administration of the composition.

The presentation system of the invention has applicability beyond use as live bacterial vaccines. The heterologous polypeptides which are presented on the surface of host cells thus remain bound to the cells, so the presentation system may be used for screening proteins and antigens, and the system can also be used as a support for immobilising an enzyme, peptide and/or antigen (Georgiou et al, 1993; Smith et al 1993).

Host cells according to the invention may therefore be used for display of antibodies and peptide libraries. A bacterial selection system complementary to phage display technology can thus be produced. The bacterial library can be separated by affinity chromatography.

A host cell displaying on its surface a heterologous polypeptide of interest can also be used to raise antibody against that polypeptide. Polyclonal antibody can be raised by, for example, administering the host cell to a mammal. The mammal may be an experimental animal such as a rabbit, mouse or rat. Antisera can be obtained from the immunised mammal.

Monoclonal antibodies can be obtained by adaptation of conventional procedures. A mammal is immunised with a host cell according to the invention, cells of lymphoid origin from the immunised mammal are fused with cells of an immortalizing cell line and thus—immortalized cells which produce antibody specific for the heterologous polypeptide of interest are selected. The selected cells are cultured to obtain quantities of the desired monoclonal antibody.

In more detail, hybridoma cells producing monoclonal antibody may be prepared by fusing spleen cells from an immunised animal with a tumour cell. The mammal which is immunised may be a rat or mouse. The hybridomas may be grown in culture or injected intraperitoneally for formation of ascites fluid or into the blood stream of an allogenic host or immunocompromised host. Human antibody may be prepared by in vitro immunisation of human lymphocytes with respect to the peptide or a fragment thereof, followed by transformation of the lymphocytes with Epstein-Barr virus.

The presentation system of the invention can further be employed as a whole-cell adsorbent. The expression of a heterologous polypeptide as part of the S-layer fusion polypeptide on the surface of host cells enables the host cells to be employed as an affinity adsorbent. Host cells may also be used to present an enzyme as the heterologous polypeptide, thus acting as biocatalysts.

As a consequence of cloning and sequencing the gene encoding the SLP of *B. sphaericus* P-1, in another aspect of the invention we have identified three promoters associated with the gene. One of these promoters is capable of directing a three-fold higher expression level than the wild-type promoter. A putative promoter previously indicated by Bowditch et al (1989) was found incapable of directing expression.

The present invention therefore additionally provides a first promoter having a −35 region of the sequence TTGAAT and a −10 region of the sequence TATATT. The critical parts of promoters are believed to be the −35 and −10 regions (Watson et al, 1987). According to the numbering scheme used, the DNA nucleotide encoding the beginning of the mRNA chain is +1.

Typically there are 16 to 18 nucleotides between the −35 and −10 regions. Preferably the intervening nucleotides (SEQ ID NO:1) are TTCGGAAAAGATAGTGT. A useful promoter has the sequence (SEQ ID NO:2) CTAAATTTAT-GTCCCAATGCTTGAATTTCGGAAAAGATAGTGT TATATTATTGT. The −35 and −10 regions are underlined.

A promoter having −35 and −10 regions of the sequences TTGAAT and TATATT, respectively, is the promoter having a transcription initiation site identified herein as P1 (see FIG. 10 of the accompanying drawings). This promoter is capable of directing expression at higher levels than the promoters having transcription initiation sites identified herein as P2 and P3 (FIG. 10) or than the entire wild type promoter sequence shown in FIG. 10 incorporating all of the three promoters. The P1 promoter is in fact three-fold stronger but only when used alone, i.e. when separated from the P2 and/or P3 promoters.

The invention also provides a second promoter having a −35 region of the sequence CTTGGTT and a −10 region of the sequence TATAAT. Typically there are 16 to 18 nucleotides between the two regions. Preferably the intervening nucleotides (SEQ ID NO:3) are ATTATTGAGAGTAAGG. A useful promoter has the sequence (SEQ ID NO:4) TCCAGAAAATGCTTGGTTATTATTGAGAGTAAGGT-ATAATAGGTA, the −35 and −10 regions being underlined.

The invention additionally provides a third promoter having a −35 region of the sequence ATTACGGGA and a −10 region of the sequence TTTAGT. Typically there are 16 to 18 nucleotides between the two regions. Preferably the intervening nucleotides (SEQ ID NO:5) are GTCTAAT-TAATTTTTGACAA. A useful promoter has the sequence (SEQ ID NO:6) AAAATATTACGGGGAGTCTTTAAT-TTTTGACAATTTAGTAACCAT, the −35 and −10 regions being underlined.

The three promoters may be tandemly arranged, for example in the order of the third promoter, the second promoter and the first promoter in the 5' to 3' direction. This is the order in which the three promoters occur in the wild-type promoter of *B. sphaericus* P-1 shown in FIG. 10. Useful DNA fragments incorporating the promoters according to the invention are the following DNA sequences shown in FIG. 10, using the number system employed in that Figure:

nucleotides 52 to 353;
nucleotides 1 to 353;
nucleotides 1 to 406; and
nucleotides 1 to 455.

The promoters can be used to direct expression of a heterologous protein in a host, for example a bacterial host such as a gram-negative or gram-positive bacterium. Suitable host cells are therefore as described above. The invention therefore provides:

(a) an expression vector which comprises a promoter according to the invention and a downstream cloning site into which a DNA sequence encoding a heterologous protein may be cloned such that the promoter is operably linked to the said sequence;
(b) an expression vector which comprises a promoter according to the invention operably linked to a DNA sequence encoding a heterologous protein; and
(c) a DNA fragment comprising a promoter according to the invention operably linked to a DNA sequence encoding a heterologous protein.

An expression vector (a) or (b) can include any suitable origin of replication which will enable the vector to replicate. A ribosome binding site is provided. The ribosome binding site is suitably located between the promoter and the cloning site or the DNA sequence encoding the heterologous protein as the case may be. If desired, a selectable marker gene such as an antibiotic resistance gene can be provided in the vector. The vector is generally a plasmid.

The cloning site of vector (a) may be provided at a translational start codon such as a NcoI site. Alternatively, no translational start codon may be provided in the vector. In that event, the foreign gene to be inserted into the cloning site would need to be provided with such a codon. Typically the gene inserted into the cloning site is provided with a translational stop codon.

Both vectors (a) and (b) are normally provided with a transcriptional termination sequence. The DNA sequences of vector (b) and of the DNA fragment mentioned above are provided with translational start and stop codons. As in the case of vectors (a) and (b), the DNA fragment will typically incorporate a ribosome binding site downstream of the promoter. The DNA fragment may be single- or double-stranded, depending on its purpose.

Vectors (a) and (b) may be constructed by assembling all appropriate elements using techniques known in the art (Maniatis et al, 1982). For example, vector (b) may be obtained by cloning a DNA sequence encoding a heterologous protein into vector (a) at the cloning site of that vector or by cloning a DNA fragment (c) into an expression vector provided with an origin of replication. The cloning site of vector (a) may be introduced by oligonucleotide-directed mutagenesis or polymerase chain reaction (PCR)-mediated site specific mutagenesis. The elements of vectors (a) and (b) are operably linked. The recombinant DNA fragment (c) may be constructed by ligating a foreign gene to a promoter sequence according to the invention.

The DNA sequence encoding a heterologous protein may be provided immediately downstream of a DNA sequence encoding a signal peptide responsible for polypeptide secretion which in turn may be provided immediately downstream of the translational start codon. The signal peptide-encoding DNA sequence may encode any signal peptide capable of directing secretion of polypeptides from gram-positive bacterium. Typically the amino acid sequence of the signal peptide ends ValAlaSerAla.

The heterologous protein may be a heterologous peptide as described above.

The following Examples illustrate the invention. In the accompanying drawings:

FIG. 1 shows the characterization of pGVP1.

A. Restriction map of pGVP1 for HindIII (1), PstI (2), SspI (3), that have double-occurring restriction sites. The single-occurring sites are indicated on the outside of the map.

B. Identification of a circular single-stranded DNA molecule as a replication intermediate of pGVP1.

Panel 1. Ethidium bromide-stained 1% agarose gel. Lane A, non-digested total DNA of B. sphaericus P-1; lane B, HhaI digested P-1 total DNA; lane C, S1 nuclease-treated P-1 total DNA; lane D, P-1 total DNA treated with $T_4$ DNA polymerase.

Panel 2. Hybridization between $^{32}$P-labelled pGVP1 and a non-denatured Southern blot of the gel in panel 1 on a nitrocellulose membrane. A specific hybridization signal, corresponding to single-stranded DNA, was observed only in non-digested (lane A) and $T_4$ DNA polymerase-treated P-1 DNA (lane D), but not in HhaI (lane B) or S1 nuclease-treated total P-1 DNA (lane C).

Panel 3. Hybridization between $^{32}$P-labelled pGVP1 and a Southern blot of a similar gel as in panel 1, but denatured prior to transfer to a nitrocellulose membrane. In all lanes, a hybridization signal, corresponding to double-stranded DNA can be observed. In lanes A and D, additionally the signal corresponding to single-stranded DNA can be observed.

Figure 2:
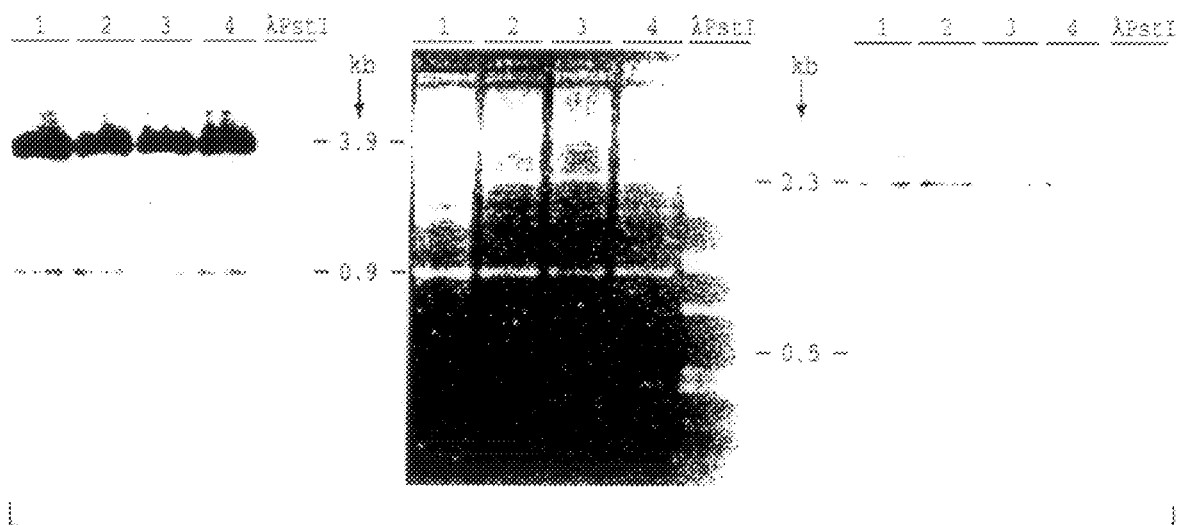

FIG. 2 shows the results of plasmid analysis of Em-resistant B. sphaericus P-1 transformed by pIL253. Central panel. HindIII-digested plasmid preparations of $Em^R$ *B. sphaericus* P-1, transformed by pIL253 (lanes 1–4), separated by agarose gel electrophoresis (ethidium bromide stained). Left panel. Autoradiogram of the hybridization between $^{32}P$-labelled pIL253 and a Southern blot of the gel in the cental panel. In all transformants, fragments specific for the introduced pIL253 plasmid (3.9 kb and 0.9 kb) are revealed. Right panel. Autoradiogram of the hybridization between the same blot as in the left panel, and $^{32}P$-labelled pGVP1. Specific fragments (2.3–0.5 kb) from the endogenous pGVP1 are revealed.

FIG. 3 demonstrates the electrocompetence in *B. sphaericus* P-1 in late-stationary phase. *B. sphaericus* P-1 cells were incubated at 37° C. in 100 ml LB broth on a gyratory shaker for 48 hr. Every 6 hr a sample was withdrawn from the culture and colony-forming units/ml were determined. Cells were pelleted by centrifugation, washed and resuspended in 1 ml of distilled $H_2$). After addition of pIL253 DNA, cells were electroporated in 0.2 cm gapped electrocuvettes ($E_0$ 12 kV/cm, R=200 Ω), diluted in 900 μl LB, incubated for 1 hr at 37° C. and plated on LB plates with erythromycin.

FIG. 4 is a schematic representation of the high-copy number (pSL40) (A) and low-copy number (pSL84) (B) bifunctional vectors for *E. coli* and *B. sphaericus* spp. Restriction sites are indicated with their relative position on the physical map. Abbreviations used: bla: β-lactamase; MLS: resistance to the macrolide-lincosamide-streptogramin B group of antibiotics; Orf E to G: open reading frames involved in replication in Gram-positive hosts. pSL40 was constructed by ligating the 2.6-kb EcoRI/XbaI fragment of pLK68 in pIL253 (EcoRI/XbaI-linearized). After restriction and filling- in at the EcoRI site of the resulting plasmid, the small multicloning site was exchanged for the polylinker of pJB66 by substituting the respective XbaI/BglII fragments. pSL84 was constructed by substituting the 1.8-kb PstI/SalI fragment of pSL40 for the 1.3-kb PstI/SalI fragment of pACYC177 (containing the low copy number origin of replication for *E. coli*). In the resulting plasmid the 2.3-kb NsilI/XbaI fragment was replaced by the corresponding NsiI/XbaI fragment of pIL252 containing the low-copy number origin of replication for Bacillus spp.

FIG. 5 is a restriction map of the genomic region containing the gene encoding the S-layer protein of *B. sphaericus* P-1. The black bar represents the signal peptide-encoding sequence; the hatched bar shows the mature part of SLP. The inserts of the four overlapping subclones used for sequence analysis are depicted below the restriction map by open bars. The arrow indicates the direction of transcription.

FIG. 6 shows the DNA sequence (SEQ ID NO:7) and deduced amino acid sequence (SEQ ID NO:8) of the slp gene of *B.sphaericus* P-1. The complete amino acid sequence (SEQ ID NO:9) is deduced. The putative ribosome-binding site preceding the SLP ORF is double underlined. The shaded residues represent the signal peptide. The nucleotide sequence of the signal peptide is SEQ ID NO: 10, and its translation into amino acids is SEQ ID NO: 11. The amino acid sequence (SEQ ID NO: 12) is deduced. The mature SLP thus commences with amino acid residue 31. The nucleotide sequence of the mature S-layer protein of *Bacillus sphaericus* P-I is SEQ ID NO: 13, and its translation into amino acids is SEQ ID NO: 14. The amino acid sequence of the S-layer protein (SEQ ID NO: 15) is deduced. Potential N-linked glycosylation sites are underlined. The stem of the Rho-independent transcription termination signal after the translation stop codon is indicated by arrows. The $NH_2$-terminal amino acid sequence determined by automated microsequence analysis of the purified mature SLP is indicated by a dotted line. The nucleotide sequence of the $NH_2$-terminal sequence is SEQ ID NO: 16, and its translation into amino acids is SEQ ID NO: 17. The amino acid sequence is SEQ ID NO:18.

FIG. 7 shows the hydropathic profile of the *B. sphaericus* P-1 S-layer protein by the computerized method of Kyte and Doolittle (1982). Horizontal bars represent potential transmembrane helices, as predicted by the method of Rao and Argos (1986).

FIG. 8 shows the sequence of the $NH_2$-terminal portion of the SLP of *B. sphaericus* P-1 and the larvicidal strain 2362. The signal peptide (SEQ ID NO: 12) sequence of both proteins is boxed. Adjustments (horizontal bars) were introduced for optimal alignment. The amino acid sequence, which is shown in FIG. 8, of the SLP portion of *B. sphaericus* P-1 is SEQ ID NO: 19. The amino acid sequence, which is shown in FIG. 8, of the SLP portion of the larvicidal strain 2362 is SEQ ID NO:20.

FIG. 9:

A. Northern blot analysis of the slp-encoded mRNA in *B. sphaericus* P-1.

Total cellular RNA was isolated from different growth phases (see text). The internal 1.81 kb HpaI fragment of the slp gene was used for the generation of a $^{32}P$-labelled probe. Migration pattern of molecular mass markers as indicated.

B. Primer extension analysis of the transcriptional initiation sites of the slp-encoded transcripts. Two different primers were used (see FIG. 10 and text for more details).

FIG. 10 shows the DNA sequence (SEQ ID NO:21) of the promoter region controlling slp expression. The position of the 5' ends of the transcripts, as determined by primer extension analysis, are indicated (black inverted triangles). The putative ribosome-binding site, preceding the slp ORF (shaded sequence) (SEQ ID NO:22) is indicated by dots. Primers used for primer extension assays were complementary to the overlined sequences. The exact end points of the different deletion mutants (pSL151 to pSL159) are shown by an arrow. Potential −10 and −35 boxes preceding the transcription initiation sites are indicated. The putative −10 and −35 regions as reported by Bowditch et al. (1989) are marked by an asterisk.

FIG. 11 shows how β-glucuronidase activity is directed by the different slp promoter deletion mutants in *B. sphaericus* P-1 (hatched bars). In pSL87 the uidA gene is under control of the $138_\emptyset$ promoter.

FIG. 12 shows the effect of $Ca^{2+}$ cations on the slp promoter-directed β-glucuronidase activity in different deletion mutants. Black bars represent *B. sphaericus* P-1 cells grown in LB medium. Hatched bars indicate cells grown upon addition of 7 mM $CaCl_2$. Activity was measured 4 hours after addition of $CaCl_2$ to the culture.

FIG. 13 shows the general outline of the strategy for disruptive single homologous recombination. $AB_1^R$: antibiotic resistance marker 1 ($Em^R$);$AB_2^R$: promoterless antibiotic resistance gene 2 (nptII); ori: origin of replication; wavy line: RNA transcript; P: promoter.

FIG. 14:

A. Restriction map of the bifunctional plasmid pSL64 used as based for the construction of different intermediate vectors. Restriction sites are indicated with their relative position on the physical map. Abbreviations used: bla: β-lactamase; MLS: resistance to the macrolide-lincosamide-streptogramin B group of antibiotics; OrfE to G: open reading frames involved in replication in Gram-positive hosts (Swinfield et al., 1990).

B. Nucleotide sequences upstream from the nptII-coding region (boxed) of pSL64 (SEQ ID NO:23) and pSL101 (SEQ ID NO:24).

FIG. 15:

A. Schematic representation of carboxy-terminal truncated SLPs obtained by single homologous recombination of the different intermediate vectors. Central block represents the restriction map of the chromosomal region containing the slp gene. Hi: HindIII; Hp: HpaI; Bg: BglII; Pv: PvuII; Xb: XbaI. Black arrows represent SLPs in the wild-type and recombinant P-1 strains as indicated on the left. Calculated molecular masses of the SLPs are indicated on the right. Striped bars indicate the used subclones of slp gene. White bars indicate internal slp fragments, cloned in pSL64 in the different intermediate vectors.

B. SDS-PAGE of proteins from wide-type P-1 (lanes A), recombinant strains P-1::pSL66 (lanes B), P-1::pSL68 (lanes C) and P-1::pSL69 (lanes D). lane M: high-molecular mass markers (Bio-Rad). Proteins are either TCA-precipitated from the supernatant of the cultures or are obtained by sonication and centrifugation. The insoluble fraction is indicated by debris, whereas the soluble fraction is indicated as sonicate.

Figure 16:
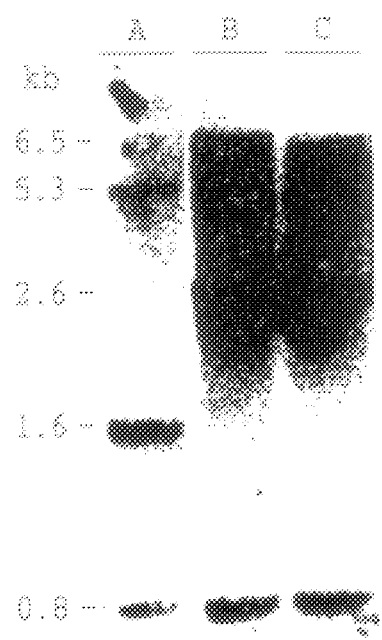

FIG. 16 is an autoradiogram of the hybridization between $^{32}$P-labelled pSL20 and BglII-digested total DNA of P-1 (lane A), P-1::pSL69 (lane B), and P-1:: pSL102 (lane C). In P-1:: pSL69 and P-1::pSL102, the 1600 BP BglII fragment, hybridizing with P-1 total DNA has disappeared, whereas two predicted fragments of 2600 and 6500 bp appeared.

FIG. 17 is a schematic representation of the peptides translationally fused to carboxy-terminally truncated SLPs in the strains P-1::pSL102, P-1::pSL113 and P-1::pSL111. Central block represents the restriction map of the chromosomal region containing the slp gene, Hi: HindIII; Hp: HpaI; Bg: BglII; Pv: PvuII; Xb: XbaI. Arrows under the restriction map represent recombinant SLPs after integration of intermediate vectors indicated above the restriction map. Black fragments represent SLP portion, striped bars indicate the S1 subunit of pertussis toxin, and white bars represent NPTII.

FIG. 18:

A. SDS-PAGE of total protein extract from P-1::pSL113 (lane 1), P-1::pSL102 (lane 2), and P-1::pSL69 (lane 3). Respective SLPs are indicated by a (130 kDa), b (102 kDa) and c (74 kDa).

B. Immunodetection on a Western blot of the gel in panel A, using anti-NPTII antibodies. Two recombinant SLPs (indicated a and b) are revealed.

C. SDS-PAGE of total protein extract from P-1::pSL111 (lanes 1–3), P-1::pSL102 (lane 4) and P-1::pSL69 (lane 5).

D. Immunodetection on a Western blot of the gel in panel C, using anti-PT antibodies. Two recombinant SLPs (of 90 and 120 kDa) are revealed (d* and d, respectively).

Figure 19:
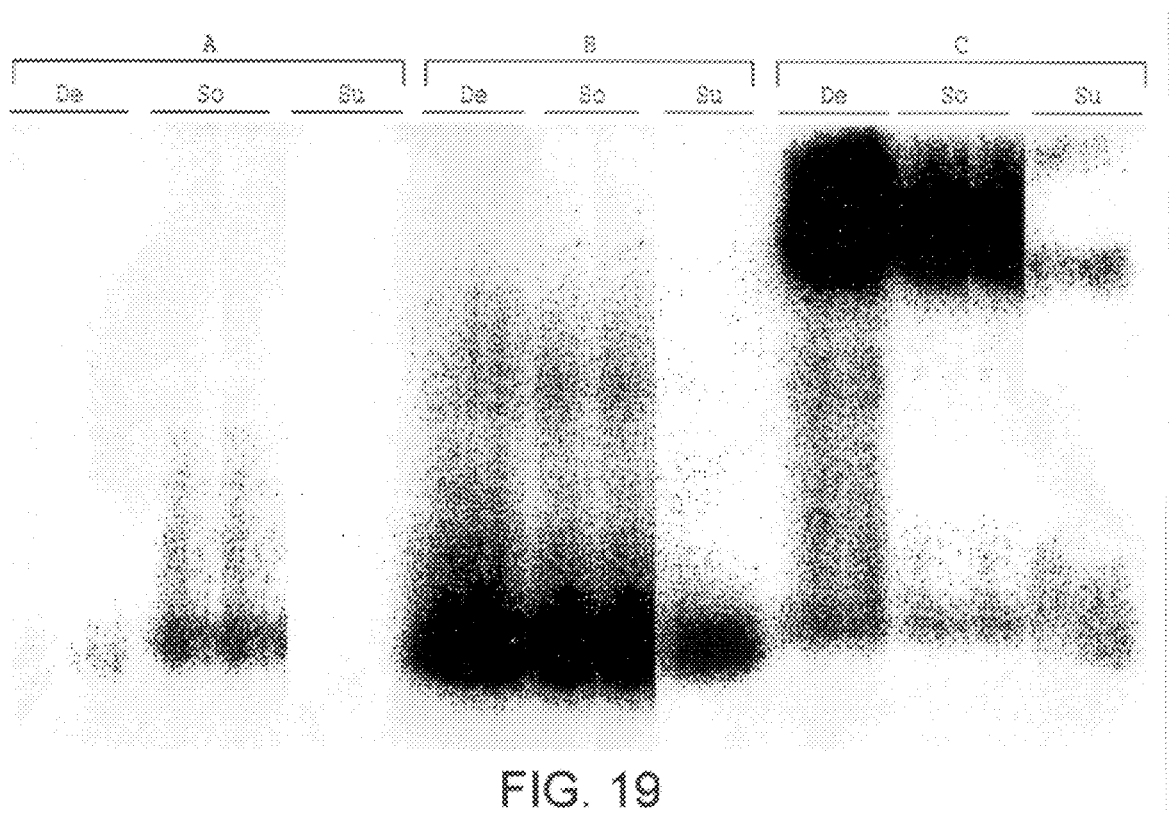

FIG. 19 is an autoradiogram of in gel kanamycin phosphorylation assay on protein extracts separated by non-denaturing polyacrylamide gel electrophoresis extracted from P-1 (panel A) P-1::PSL69 (panel B), and P-1::pSL102 (panel C). Significant phosphorylating activity in the high-molecular mass region can only be observed in P-1::pSL102.

Figure 20A:
Figure 20B:
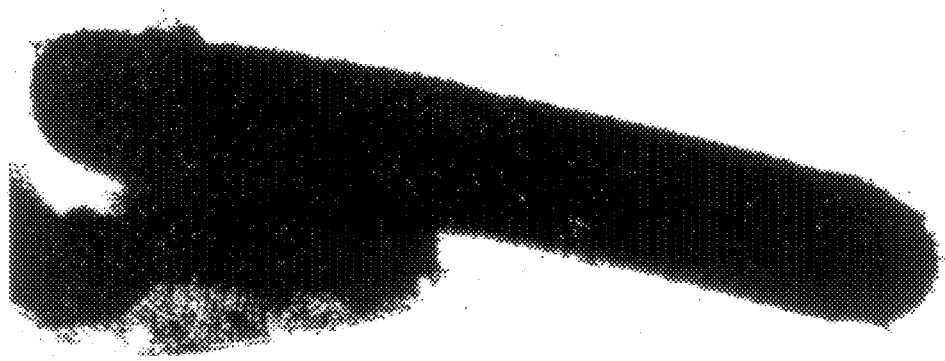
Figure 20C:

FIG. 20 shows immunogold labelling on intact bacteria using anti-NPTI antibodies. Panel A, P-1::pSL69, panel B, P-S::pSL102; panel C, P-2::pSL113. Significant accumulation of gold-label can only be observed in P-a::pSL102 and to a lesser extent in P-1::pSL113.

FIG. 21 shows the detection of PT subunit S1 and NPTII in native sacculi prepared from P-1::PSL102 and P-1::pSL111. CE: cellular extracts; NS: native sacculi.

Example 1

1. Materials and Methods

Bacterial strains and plasmids. In Table I, the bacterial strains and plasmids used in this study are listed. *B. sphaericus* strains were grown in Luria-Bertani (LB) broth (Miller, 1972), supplemented with 0.7% agar for solid media. Selective antibiotic concentrations for *B. sphaericus* were: 10 μg/ml erythromycin (Em); 10 μg/ml nalidixic acid (Na). For *E. coli,* 200 μg/ml of triacillin was used.

TABLE I

Bacterial strains and plasmids used in this study

| | Characteristics | References |
|---|---|---|
| *E. coli* | | |
| DH5α | $F^-$, ø80dlacZΔM15, Δ(lacZYA-argF)$_{U169}$, recA1, endA1, hsdR17($r_k^-$, $m_k^+$), supE44 | Hanahan (1983) |
| MC1061 | hsdR, hsdM, hsdS, araD139, Δ(ara—leu)$_{7697}$, Δlac$_{x74}$, galU, galK, rpsL | Casadaban and Cohen (1980) |
| *B. sphaericus* | | |
| P-1 | Nalidixic acid resistant | Lewis et al. (1987) |
| 1593 | | BGSC |
| 10208 | | ATCC |
| *Lactococcus latis* | | |
| MG1363 | | Gasson and Davies (1980) |
| Plasmids | | |
| pGVP1 | natural isolate in *B. sphaericus* P-1 | This study |
| pGVP2 | cointegrate on BamHI-linearized pUC9 and Bg1II-linearized pGVP1 | This study |
| pUC9 | $Ap^R$ | Vieira and Messing (1982) |
| pPGV5 | bifunctional, $Ap^R$, $Nm^R$ | This study |
| pJB66 | $Ap^R$ | Botterman and Zabeau (1986) |
| pSL40 | cointegrate of pJB66 and pIL253, $Ap^R$, $MLS^R$ | This study |
| pSL84 | cointegrate of pACYC177 and pIL252, $Ap^R$, $MLS^R$ | This study |
| pAMβ1 | $MLS^R$, autotransmissible, natural isolate | Clewell et. al (1974) |
| pIL252 | $MLS^R$, low-copy number vector derived from pAMβ1 | Simon and Chopin (1988) |
| pIL253 | $MLS^R$, high-copy number vector derived from pAMβ1 | Simon and Chopin (1988) |
| pACYC177 | $Ap^R$, $Km^R$, low-copy number vector | Chang and Cohen (1978) |

Transformation and plasmids. Competent *E. coli* strains were prepared and transformed according to Kushner (1978). Transformation of *B. sphaericus* P-1 intact cells was achieved by electroporation using the protocol developed as described in the Results section below. *B. sphaericus* P-1 cells, grown in LB broth for 42 hr at 37° C. on a gyratory shaker, were harvested by centrifugation (9000 g), washed with ice-cold distilled $H_2O$, resuspended in 1/10 volume of a 10% glycerol solution in distilled $H_2$), aliquoted in 100 μl samples, and stored at −70° C.

For transformation, samples were quickly thawed, mixed with DNA, and transferred into 0.1 cm gapped electrocuvettes. An electrical pulse (14 kV/cm, 25 µF) was delivered, using a GenePulser (Trade Mark) apparatus (Bio-Rad laboratories) with Pulse Controller extension set at 200 Ω. After the electrical pulse was delivered, cells were diluted with 900 µl of LB broth and incubated at 37° C. for 1 hr, prior to plating on solid LB medium, and supplemented with appropriate antibiotics.

General recombinant DNA techniques. *E. coli* plasmid DNA was prepared according to Sambrook et al. (1989), whereas for plasmid and total DNA preparations of *B. sphaericus,* cells were pretreated with lysozyme (100 µg/ml) at 37° C. for 10 min. Restriction enzymes were purchased from New England Biolabs, Pharmacia (Uppsala, Sweden) or Bethesda Research Laboratories, and were used according to the manufacturers' recommendations.

Elution of DNA restriction fragments was done using GeneClean II (Trade Mark) kit (Bio101 Inc., La Jolla, Calif., US). Filling-in of protruding single-stranded termini after restriction enzyme digestion (using Klenow or $T_4$ DNA polymerase) and ligations were done according to standard conditions (Sambrook et al., 1989). Southern transfer and hybridization were performed using Hybond $N^+$ membranes (Amersham) and QuickPrime (Trade Mark) labelling kit (Pharmacia) to prepare $^{32}P$-labelled probes, except for blotting of single-stranded DNA, which was achieved using nitrocellulose membranes.

2. Results

Characterization of endogenous plasmids of *B. sphaericus* P-1. Plasmid preparations, according to the alkaline lysis method, followed by equilibrium density gradient centrifugation, revealed the presence of a small plasmid (2.8 kb), designated pGVPI, in *B. sphaericus* P-1. By preliminary restriction analysis of pGVPI, a unique restriction site for BglII was found. For further restriction enzyme analysis, a cointegrate plasmid (pGVP2) was constructed, by joining BglII-linearized pGVP1 and BamHI-linearized pUC9, allowing large-scale preparations from *E. coli.* Single- and double-occurring restriction enzyme sites (BglII, AvaI, NcoI, PstI, HindIII, SspI) were ordered by appropriate double digestions (FIG. 1A). No sites were founds for KpnI, BamHI, EcoRI, ApaI, ClaI, EcoRV and SphI.

Figure 1B:
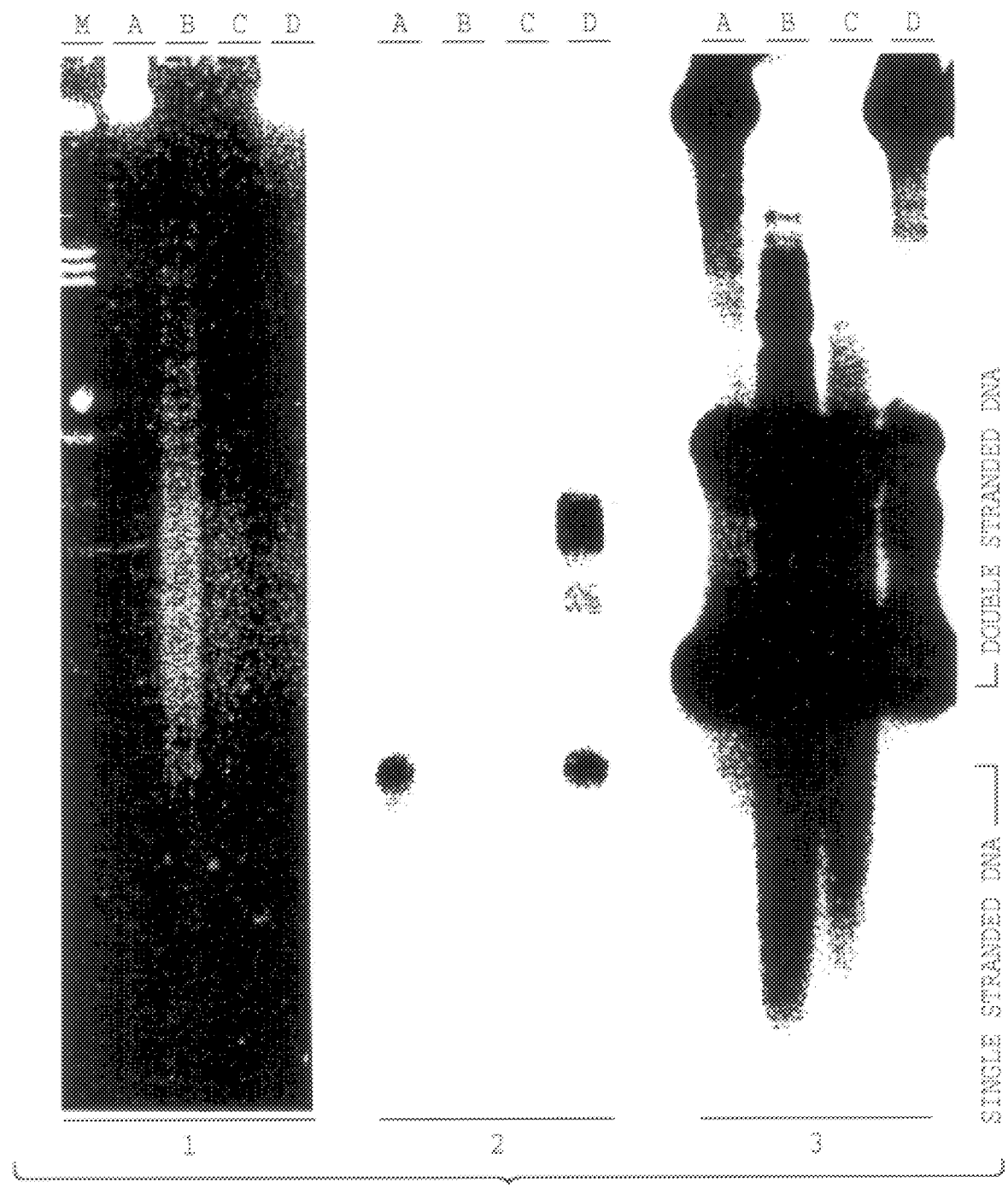

Hybridizations were performed between $^{32}P$-labelled pGVPI and Southern transfers of non-denatured total DNA of *B. sphaericus* P-1 to nitrocellulose membranes (a frequently used method for detection of single-stranded replication intermediates in Gram-positive replicons; Gruss and Ehrlich, 1989). A specific hybridization signal was observed in undigested total DNA (FIG. 1B, panel 2, lane A), corresponding to a single-stranded intermediate. The signal was not detected in DNA samples which were digested either with S1 nuclease or with the single-stranded DNA-cleaving endonuclease HhaI, prior to gel separation.

Treatment with $T_4$ polymerase, which degrades specific linear single-stranded DNA, did not decrease the signal, indicating that the pPGV1 replication intermediate is circular. As it is of considerable interest to use *B. sphaericus* P-1 as a host for transformation experiments several methods for plasmid curing that proved successful in Gram-positive bacteria [including novobiocin (Gonzales et al., 1981), rifampin (Johnston and Richmond, 1970), sodium dodecyl sulfate (Sonstein and Baldwin, 1972)] were tried out but did not result in the production of a plasmid-free strain.

Introduction of pAMβ1 into *B. sphaericus* P-1 by intergeneric conjugation. To test whether the macrolide lincosamide steptogramin B (MLS) resistance determinant and the origin of replication of the auto-transmissible plasmid pAMβ1 (26.5 kb) were functional in *B. sphaericus* P-1, this plasmid was introduced into P-1 by conjugating it with *Lactococcus lactis* MG1363 [pAMβ1] (Gasson and Davies, 1980). This plasmid was chosen because it had previously been introduced successfully into *B. sphaericus* 1593 (Orzech and Burke, 1984). After overnight incubation of a mixture of both strains (ratio 1:1) on nitrocellulose filters placed on M17$^+$ lactose medium at 37° C., bacteria were collected and several dilutions were plated on LB medium supplemented with Em.

Em-resistant *B. sphaericus* P-1 colonies were obtained at a frequency of $3 \times 10^6$ (transconjugants/acceptor strain). After colony purification on LB medium supplemented with erythromycin and nalidixic acid, putative transconjugants were analyzed for the presence of pAMβ1 by Southern hybridization using $^{32}P$-labelled pAMβ1 as a probe (data now shown). The plasmid was stable for several generations, even in the absence of selective pressure. These results prompted us to use pAMβ1-derived cloning vectors (e.g. pIL253) for electrotransformation experiments in P-1.

Electrotransformation. Initial experiments using pIL253 to transform *B. sphaericus* strains, following reported protocols for electrotransformation of several Bacilli (Takagi et al., 1989; Bone and Ellar, 1989; Taylor and Burke, 1990) were unsuccessful. The common denominator in these protocols is the use of cells harvested in early or mid-log growth phase. However, using cells harvested from late-log solid-grown colonies, which were washed once with ice-cold distilled $H_2O$, and standard electrical parameters for *E. coli* (12 kV/cm, 200 Ω, 25 µF in 0.2 cm gapped electrocurvettes), $10^2$ transformants were obtained. Plasmid analysis revealed the presence of two plasmids that could be identified as the endogenous pGVP1 and the introduced pIL253 by Southern hybridization (FIG. 2).

Figure 3:
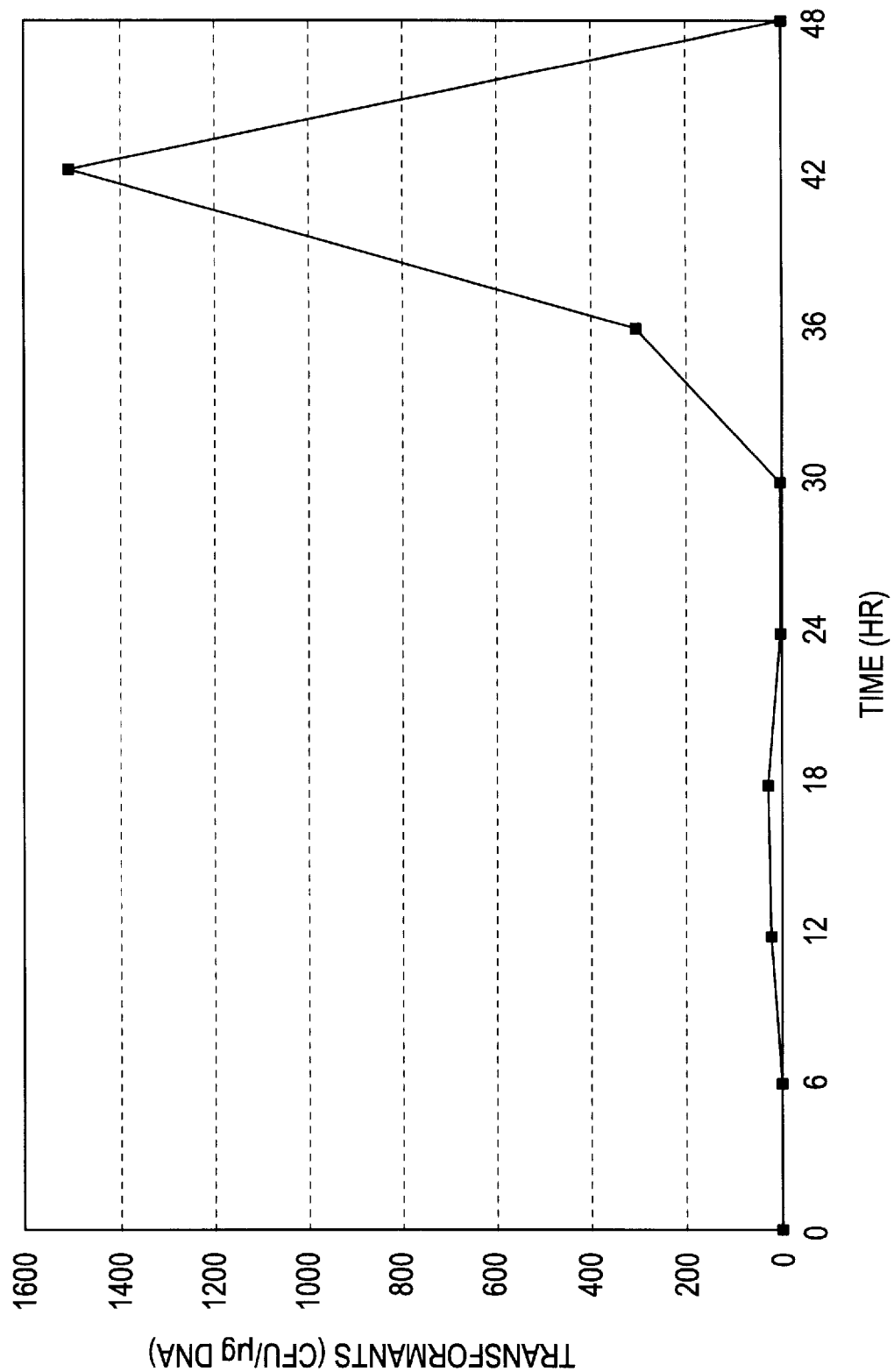

To optimize the physiological conditions for electroporation of P-1, cells harvested at different time-points in a growing culture were washed once and resuspended in ⅒ volume distilled $H_2O$, and electroporated (at 12 kV/cm, 200 Ω, 25 µF in 0.2-cm gapped electrocuvettes). Although growth of the culture stagnated after 8 hr, transformants were not obtained until 36 hr of incubation. The number of transformants reached a maximum at 42 hr incubation, and significantly decreased after 48 hr of incubation, presumably due to cell death (FIG. 3). This phenomenon demonstrates the need for a certain physiological state of the bacterial cells required for electrotransformation, or in other words electrocompetence. Electrocompetence has been inferred to explain saturation of transformation efficiencies at increasing DNA concentration (Chassy et al., 1988; Desomer et al., 1990).

Addition of different chemicals (used to increase transformation efficiency in protocols for different bacterial species) to the electroporation medium, such as polyethylene glycol (PEG) 1000 (15% w/v) and glycerol (10% w/v) improved the transformation efficiency significantly. (Table II). Variation of the electrical parameters included transformation at higher voltages (12, 14 and 16 kV/cm in 0.1-cm gapped electrocuvettes) and use of different external resistances (200, 400 and 600 Ω). Maximum transformation efficiencies were obtained at 14 kV/cm, 25 µF, 200 Ω using 0.1-cm gapped electrocuvettes (Table II below).

Combination of both improved protocols, as described in the Materials and Methods section above, routinely yielded $10^5$ transformants per µg DNA. Cells could be kept frozen at −70° C. without significant loss of electrocompetence.

The high transformation efficiency obtained by this protocol prompted us to test whether plasmids with single-stranded replication intermediates (such as the pUB110-derived vector pPGV5) could be used as transforming DNA, and eventually yield a P-1 strain, cured of pGVP1 by incompatibility. pPGV5 is a cointegrate via the EcoRI site of pUC4 (Vieira and Messing, 1982) and pPL703 (Mongkolsuk et al, 1983). Nm-resistant transformants were obtained with low frequency (Table II below) and contained intact pPGV5 in addition to the endogenous pGVP1 (data not shown).

Application of the same protocol to *B. sphaericus* 1593 and ATCC 10208 yielded no transformants (Table II below). Indeed, a previously published protocol for electrotransformation for *B. sphaericus* 1593 used cells harvested in early-log growth-phase (Taylor and Burke, 1990).

Construction of bifunctional vectors for *E. coli* and *B. sphaericus*. Bifunctional vectors that can replicate in both *B. sphaericus* and *E. coli* have the advantage that cloning procedures and analysis can be done with well established methods in *E. coli* prior to introduction of the final construct into *B. sphaericus*. Bifunctional plasmids were constructed with high- (PSIA40) and low-copy number (pSL84) in both hosts. pSL40 contains the multilinker, ampicillin-resistance gene and the Co1E1 origin of replication of pJB66 (Botterman and Zabeau, 1980) as well as the MLS determinant and origin of replication of pIL253 (FIG. 4A). In pSL84, the high-copy number origin of replication of pJB66 is exchanged for the low-copy number origin of pACYC177, whereas the origin of pIL253 is replaced for that of pIL252, an ancestral plasmid of pIL253 with low-copy number (FIG. 4B). Upon introduction in *B. sphaericus* P-1, both plasmids exhibited the expected copy number control. No significant difference in transformation efficiency was observed using pSL40 or pSL84 prepared from either the *E. coli* MC1061 or the *B. sphaericus* P-1 hosts (Table II below).

TABLE II

Transformation efficiencies using different electrical conditions, *B. sphaericus* strains and plasmids

| Strain | Electroporation medium | $E_o$ kV/cm | R Ω | Plasmid | Transformation efficiency[d] |
|---|---|---|---|---|---|
| P-1 | $H_2O$ | 0 | 200p | IL253 | $<10^1$ |
| P-1 | $H_2O$ | 6 | 200 | pIL253 | $2.0 \times 10^1$ |
| P-1 | $H_2O$ | 10 | 200 | pIL253 | $3.4 \times 10^2$ |
| P-1 | $H_2O$ | 12 | 200 | pIL253 | $8.5 \times 10^2$ |
| P-1 | $H_2O$ | 12[a] | 200 | pIL253 | $9.6 \times 10^3$ |
| P-1 | $H_2O$ | 14[a] | 200 | pIL253 | $6.7 \times 10^3$ |
| P-1 | $H_2O$ | 16[a] | 200 | pIL253 | $8.6 \times 10^2$ |
| P-1 | $H_2O$ | 14[a] | 400 | pIL253 | $5.3 \times 10^3$ |
| P-1 | $H_2O$ | 14[a] | 600 | pIL253 | $4.7 \times 10^2$ |
| P-1 | 30% PEG 1000 | 12 | 200 | pIL253 | $<10^1$ |
| P-1 | 15% PEG 6000 | 12 | 200 | pIL253 | $4.0 \times 10^1$ |
| P-1 | 15% PEG 1000 | 12 | 200 | pIL253 | $2.4 \times 10^2$ |
| P-1 | 10% glycerol | 12 | 200 | pIL253 | $1.4 \times 10^3$ |
| P-1 | 10% glycerol | 14[a] | 200 | pIL253 | $6.5 \times 10^5$ |
| P-1 | $H_2O$ | 12 | 200 | pPGV5[b] | $8.0 \times 10^1$[c] |
| 1593 | $H_2O$ | 12 | 200 | pIL253 | $<10^1$ |
| 10208 | $H_2O$ | 12 | 200 | pIL253 | $<10^1$ |
| P-1 | 10% glycerol | 14[a] | 200 | pSL40 | $2.0 \times 10^3$ |
| P-1 | 10% glycerol | 14[a] | 200 | pSL40[b] | $2.6 \times 10^3$ |

[a]in 0.1-cm gapped electrocuvettes;
[b]plasmid source was *E. coli*;
[c]selected on LB with Nm;
[d]number of transformants selected on LB EM per μg of DNA.

Example 2

1. Materials and Methods

Bacterial strains, plasmids and media. Bacterial strains used are *B. sphaericus* P-1 (Lewis et al, 1987) and *B. subtilis* BR151 Bacillus Genetic 10 Stock Center, Ohio State University, Columbia). *E. coli* hosts were either DH5α (Hanahan, 1983) or MC1061 (Casadaban and Cohen, 1980). Cloning was performed in pUC18 (Yanisch-Perron et al, 1985). pSL40 (Example 1) is a high copy number *E. coli*-Bacillus shuttle vector, essentially composed of pJB66 (Botterman and Zabeau, 1987) and pIL253 (Simon and Chopin, 1988). The β-glucuronidase (uidA) gene cassette was isolated from pGUSl (Peleman et al, 1989) and introduced into pSL40 as a BamHI/SphI fragment, yielding pSL150. Bacteria were grown on LB medium (Miller, 1972) solidified with 1.5% agar, whereas liquid cultures were grown in TB medium (Tartof and Hobbs, 1987). When required antibiotics were added: ampicillin (100 μg/ml) or erythromycin (10 μg/ml). All cultivations were performed at 37° C.

DNA techniques. Recombinant DNA techniques for *E. coli* were performed according to standard conditions (Sambrook et al, 1989). Restriction and modifying enzymes were purchased from Pharmacia, New England Biolabs, Promega or Bethesda Research Laboratories and used according to their recommendations. DNA fragments were purified from agarose gel using the Gene Clean Kit (Bio-101 Inc.). DNA sequences from both strands were determined by the dideoxy-chain termination method (Sanger et al, 1977) using the T7 Sequencing Kit (Pharmacia). Sequence analysis was carried out with the Intelligenetics suite of program (Intelligenetics Inc.). Databases were screened by FASTDB software (Brutlag et al, 1990). Unidirectional deletions were generated by combined ExoIII/S1 nuclease activity, using the Double-stranded Nested Deletion Kit (Pharmacia). Oligonucleotides were synthesized on an ABI 394 DNAIRNA Synthesizer (Applied Biosystems Inc.). High voltage transformation of *E. coli* DH5α with ligation mixtures was done with a Bio-Rad Gene Pulser (Trade Mark). Site-specific mutagenesis using polymerase chain reaction (PCR) was performed as described (Landt et al, 1990).

Construction and screening of libraries. *B. sphaericus* P-1 genomic DNA was prepared as described by Mielenz (1983) and digested to completion with the appropriate restriction enzyme. Libraries were constructed in digested and dephosphorylated pUC18, according to standard conditions (Sambrook et al, 1989). 3840 colonies were transferred to Hybond-N nylon membranes (Amersham International) and screened by colony hybridization under standard stringency conditions. $^{32}$P-labelled probes were generated using the $^{T7}$Quick Prime (Trade Mark) Kit (Pharmacia).

RNA analysis. Total RNA was extracted from *B. sphaericus* P-1 by the hot-phenol method of Aiba et al (1981). Total RNA isolated at different growth phases was run on a formaldehyde containing agarose gel and transferred to Hybond-N nylon membranes (Pharmacia) and hybridized according to the manufacturer's recommendations. Single stranded oligonucleotides (FIG. 10) were used as primers in a primer extension assay. 50 μg of RNA was mixed with 50 ng primer and ethanol-precipitated. The pellet was resuspended in 20 μl 5×hybridization buffer (2 M NaCl, 50 mM PIPES pH 6.4, 5 mM EDTA) and 80 μl deionized formamide and incubated for 15 minutes at 85° C. Primer annealing proceeded over-night at 37° C. Primed RNA was ethanol-precipitated. The extension reaction was carried out for 90 minutes at 42° C. in a 40 μl mixture containing 50 mM Tris.HCl (pH 8.2), 10 mM dithiothreitol, 6 mM $MgCl_2$, 25 μg/ml actinomycin D, 250 μM dCTP, dGTP, dTTP, 150 μM dATP, 60 μCi [α-$^{35}$S] dATP (Amersham International) and 40 units Reverse Transcriptase. Upon completion of the reaction 2 μl pancreatic RNase (1 mg/ml) was added and incubated for another 20 minutes. Extension products were purified by phenol/chloroform extraction and subsequent ethanol precipitation. The size of the extended products was deduced by comparison to a corresponding sequence ladder, generated with the same primer.

Protein micro-sequence analysis. The surface-layer protein from *B. sphaericus* P-1 was isolated from cell walls by urea extraction as described by Lewis et al (1987). Upon sodium dodecyl sulfate polyacrylamide gel electrophoresis (SDS-PAGE) proteins were electro-blotted and immobilized on a treated glass fibre plate (Bauw et al, 1987) for NH2-terminal amino acid sequence determination on an automated ABI 473A Protein Sequencer (Applied Biosystems Inc.).

Enzyme assay. β-glucuronidase activity was measured essentially as described (Jefferson et al, 1986) using p-nitrophenyl-β-D-glucuronide as substrate. Cells were resuspended in 1 ml reaction buffer, supplemented with 0.01% SDS. Permeabilization of bacterial cells was achieved by addition of 25 μl chloroform and vortexing for 10 seconds. After termination of the reaction, cells were pelleted and the cleared supernatant was used for O.D. measurement.

2. Results

Identification and cloning of the sip gene. The surface-layer protein of *B. sphaericus* P-1 was purified and subjected to automated microsequence analysis. 21 $NH_2$-terminal amino acid residues (SEQ ID NO: 18) could be deduced: $NH_2$-Ala-Gln-Val-Asn-Asp-Tyr-Asn-Lys-Ile-Ser-Gly-Tyr-Ala-Lys-Glu-Ala-Val-Gln-Ala-Leu-Val. Based on residues 11 to 19 of this sequence, a specific oligodeoxynucleotide probe mixture was synthesized with the following sequence (SEQ ID NO:25): 5'-GCYTGIACIGCYTCYTTI-GCITAICC-3' wherein Y is C or T, and wherein I is inosine. Several unique bands were revealed on Southern blots of restricted genomic DNA when hybridized to the $^{32}P$-labelled oligonucleotide probe.

A preliminary restriction map was established from which it was deduced that the 5.0-kb EcoRI fragment very probably contained the complete slp gene. An EcoRI-generated library of *B. sphaericus* P-1 genomic DNA in pUC18 was screened by colony hybridization. Despite the use of different hybridization conditions no subclones containing the 5.0-kb fragment could be isolated, suggesting that cloning of the entire gene or a large part of it in *E. coli* is lethal to the host. Therefore cloning of smaller restriction fragments, identified in the Southern blot analysis, was pursued.

Screening of a HindIII-generated library resulted in the isolation of a pUC18 clone (pSL1), containing a 1.8-kb insert. Further analysis showed that the homology could be delineated to a small 100-bp HindIII/PvuII fragment. Sequence analysis confirmed this homology: the deduced amino acid sequence of this region completely matched the sequence as obtained after microsequencing of the SLP subunit. Preceding this region a typical signal peptide sequence for secretion was detected. The pSL1 clone thus contains the slp promoter and a stretch encoding a 30-residue signal peptide and the first 20 amino acid residues of the SLP of *B. sphaericus* P-1.

It also became clear that the originally identified 5.0-kb EcoRi fragment indeed contained the complete slp gene, including its own promoter. However due to inability to clone this fragment in *E. coli,* we were obliged to isolate the gene as a set of overlapping clones. In this way, three other pUC18 clones were isolated from several libraries using the previous fragment as probe: pSL4, containing a 0.8-kb PvuII fragment; pSL10, harbouring a 1.6-kb BglII fragment and pSL20 carrying a 3.0-kb HindIII fragment (FIG. 5). In total a region of 4.6 kb was spanned from which the DNA sequence was determined (FIG. 6).

The slp gene sequence. Analysis of the DNA sequence starting from the EcoRI site to the most downstream HindIII site revealed an open reading frame (ORF) of 3756 nucleotides, starting at the ATG initiation codon (position 95 to 97; FIG. 6) and terminating at the stop codon TGA (position 3851 to 3853; FIG. 6), whereas as many as 256 translation stop codons are dispersed over the 2 other reading frames. This ORF could encode a polypeptide of 1252 residues with a deduced molecular mass of 130,060 Da, which is 20 kDa less than the value deduced from SDS-PAGE. This discrepancy is probably due to the fact that the *B. sphaericus* P-1 SLP is glycosylated (Lewis et al, 1987). Indeed, 20 potential N-linked glycosylation sites are distributed over the sequence. The protein has a calculated pI value of 4.59, which is in accordance with the experimentally determined value of 4.6±0.4 (Lewis et al, 1987).

The 3' end of the ORF is followed by a palindrome with a stem of 13 base pairs (position 3904 to 3933; FIG. 6) and a thymidine-rich stretch, which is typical for a Rho-independent transcription termination signal (Platt, 1986). The start codon ATG is preceded by a potential ribosome-binding site 5'-AGGGAGG-3' (position 78 to 85; FIG. 6). The 11 nucleotide-spacing between the middle A of this motif and the ATG codon is typical of that found in gram-positive bacteria (Hager and Rabinowitz, 1985).

The deduced amino acid sequence was analyzed by the computerized method of Kyte and Doolittle (1982) for hydropathicity (FIG. 7). The $NH_2$-terminal sequence (30 residues) appears to be very hydrophobic, which is in accordance with the presence of a signal peptide responsible for secretion. It moreover ends by the sequence VASA, a motif frequently recognised by signal peptidases (von Heijne, 1986) and is then directly followed by the sequence determined by microsequence analysis of the mature SLP subunit. Several other hydrophobic regions, which might interfere with membrane translocation were observed at the COOH-terminus (FIG. 7).

Table III shows the amino acid composition of the SLP, which shares several features with other S-layer proteins. The only sulphur-containing amino acid is methionine (2 residues). It contains a high proportion of hydrophobic amino acids (38%), but it is not very enriched in acidic residues (10.6%) versus basic residues (8.3%), as is the case for the two S- layer proteins of *B. brevis* 47 (Tsuboi et al, 1988). No significant homology to other S-layer proteins was found, except with the SLP of *B. sphaericus* 2362 (Bowditch et al, 1989), at the level of the $NH_2$-terminal sequence (FIG. 8). The first 200 residues show a degree of 82% identity. However, no homology downstream of this region could be detected. This observation was confirmed by comparing the hydropathicity plots of both proteins (data not shown).

TABLE III

Amino acid composition of the *B. sphaericus* P-1 SLP

| Amino Acid | Number | % (molecular mass) |
|---|---|---|
| Threonine | 166 | 12.8 |
| Valine | 134 | 10.2 |
| Alanine | 181 | 9.9 |
| Lysine | 91 | 9.0 |
| Asparagine | 88 | 7.7 |
| Glutamic acid | 69 | 6.9 |
| Leucine | 64 | 5.6 |

TABLE III-continued

Amino acid composition of the *B. sphaericus* P-1 SLP

| Amino Acid | Number | % (molecular mass) |
|---|---|---|
| Aspartic acid | 62 | 5.5 |
| Phenylalanine | 47 | 5.3 |
| Serine | 78 | 5.2 |
| Isoleucine | 55 | 4.8 |
| Tyrosine | 37 | 4.6 |
| Glycine | 95 | 4.2 |
| Glutamine | 34 | 3.4 |
| Proline | 31 | 2.3 |
| Arginine | 11 | 1.3 |
| Tryptophan | 6 | 0.9 |
| Methionine | 2 | 0.2 |
| Histidine | 1 | 0.1 |
| Cysteine | 0 | 0.0 |

Figure 9A:
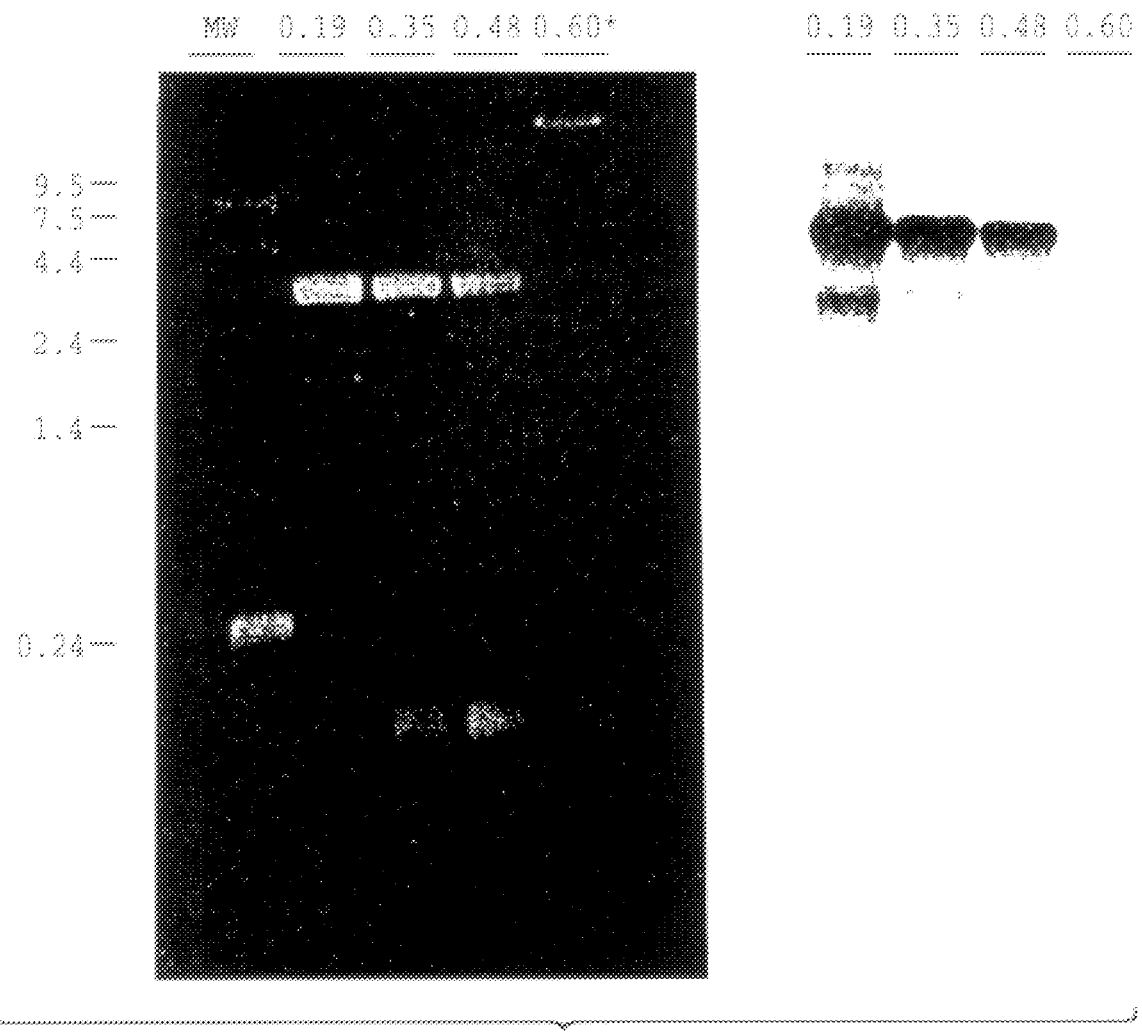
Figure 9B:
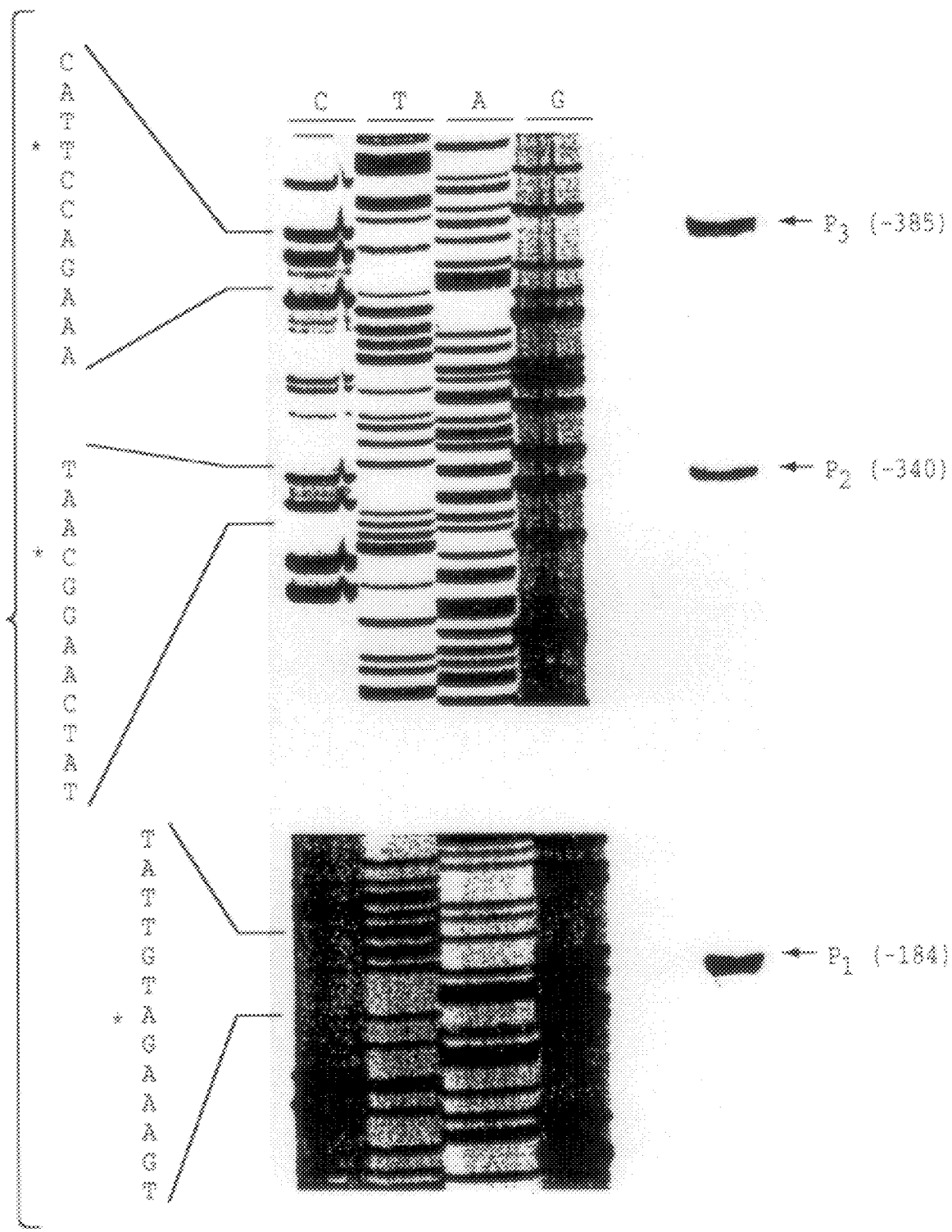

The sip promoter. In order to examine how the slp gene is transcribed in vivo total RNA was isolated at different growth phases: early and middle logarithmic phase, early stationary phase and from an overnight saturated culture. Northern blot analysis demonstrated the presence of one single transcript of approximately 4500 nucleotides. The sip gene is expressed at high level up to early stationary phase. However a sharp decrease is observed in a saturated culture, together with a simultaneous drop in rRNA levels due to stringent response (Cashel and Rudd, 1987) (FIG. 9). These high levels of expression during most of the bacterial growth cycle are to be expected in view of the continuous need of large amounts of SLP subunits for the assembly of an intact surface-layer, even at stationary growth phase when the SLP is released into the medium (Howard and Tipper, 1973).

Primer extension assays were performed to study the existence of complex multiple promoters involved in regulation of slp gene expression, such as in the case of *B. brevis* 47 (Adachi et al, 1989). Using two different primers the 5' end(s) of the transcript were detected. Three different transcription initiation sites were identified in both experiments at positions −184 (P1), −340 (P2) and −385 (P3) with respect to the first nucleotide (+1) of the start codon (FIG. 10). Each transcription start site was preceded by a potential −10 and −35 motif as indicated in FIG. 10. Spacing between both motifs corresponded to the preferred internal length (16 to 18 bp) for *B. subtilis* promoters (Moran et al, 1982).

β-Glucuronidase fusions to study sip gene expression. The slp promoter was fused to the β-glucuronidase (uidA) reporter gene to examine the expression characteristics of this complex 5'-upstream region. Through PCR-mediated site-specific mutagenesis a NcoI site was generated at the ATG start codon of the slp gene. The promoter was then isolated as a XbaI/NcoI fragment and fused to the uidA ORF at the NcoI site in pSL150, yielding pSL151.

Figure 11:
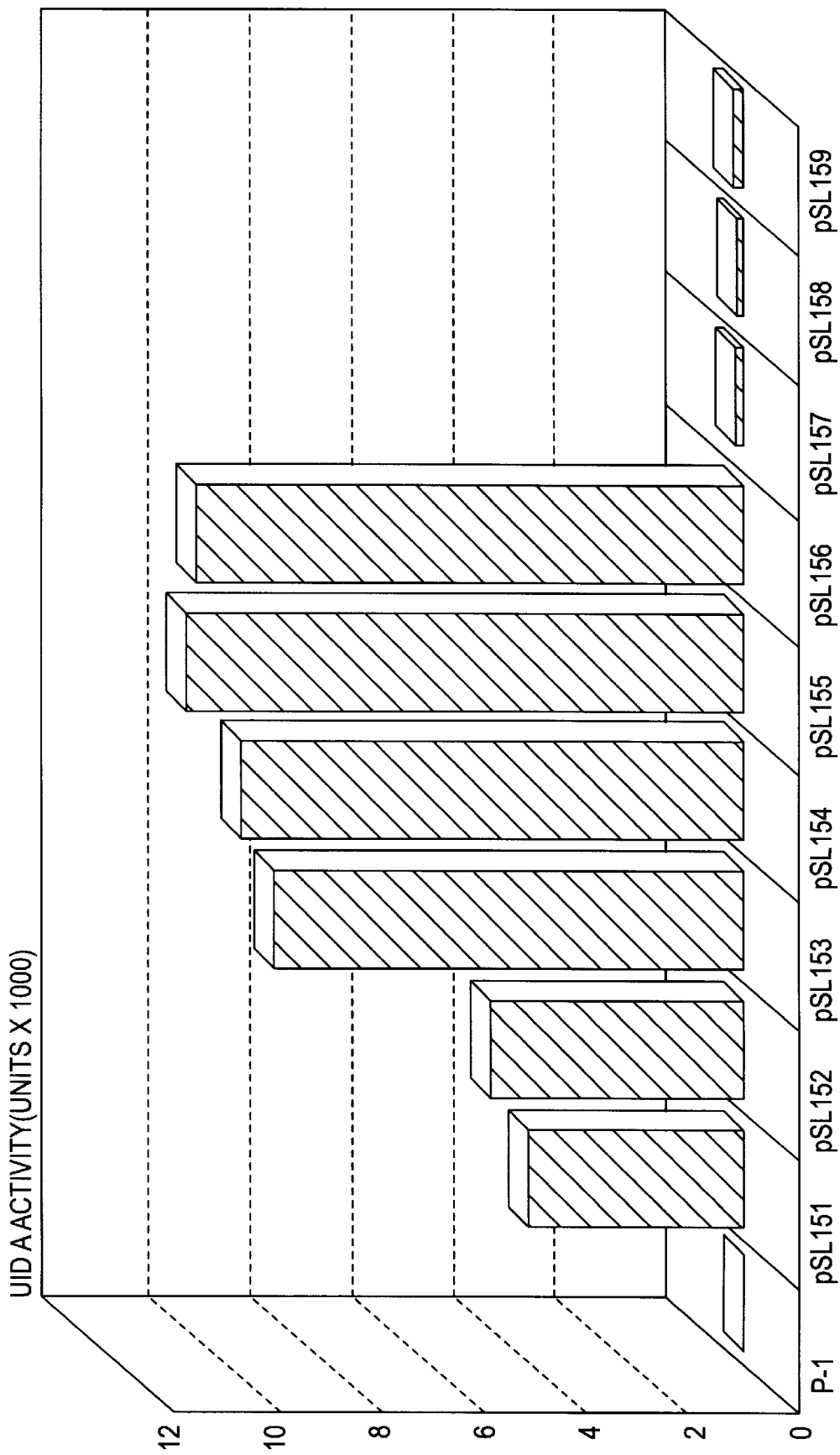

Through the combined action of ExoIII/S1 nuclease a set of progressive deletions towards the ATG start codon was generated and introduced into pSL150 as XbaI/NcoI fragments. The exact end point of each deletion was determined by sequence analysis (FIG. 11). This set of plasmids (pSL151 to pSL159) was introduced into *B. sphaericus* P-1 by electrotransformation as described in Example 1 and β-glucuronidase activity was monitored.

The results are shown in FIG. 11 and can be summarized as follows: deletions up to approximately position −150 are completely abolished in uidA expression. Indeed, according to the primer extension assay these mutants are devoid of any of the three identified promoters. Deletions removing sequences up to position −375 show a threefold increase in β-glucuronidase activity as compared to pSL151. These constructs only contain promoter P1. All smaller deletions show again wild-type levels of β-glucuronidase activity. In these mutants all three promoters are intact again.

Figure 12:
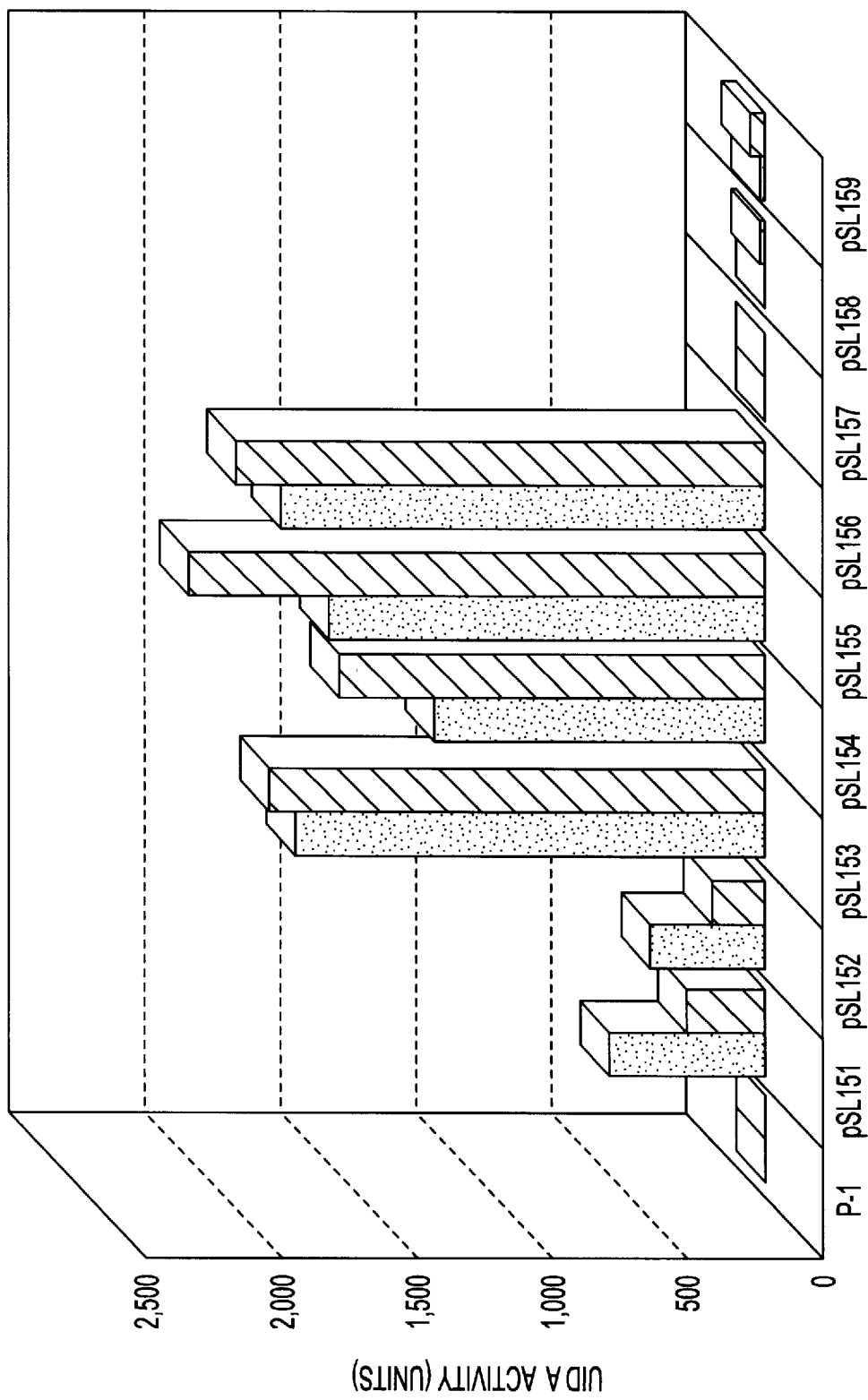
Figure 13:
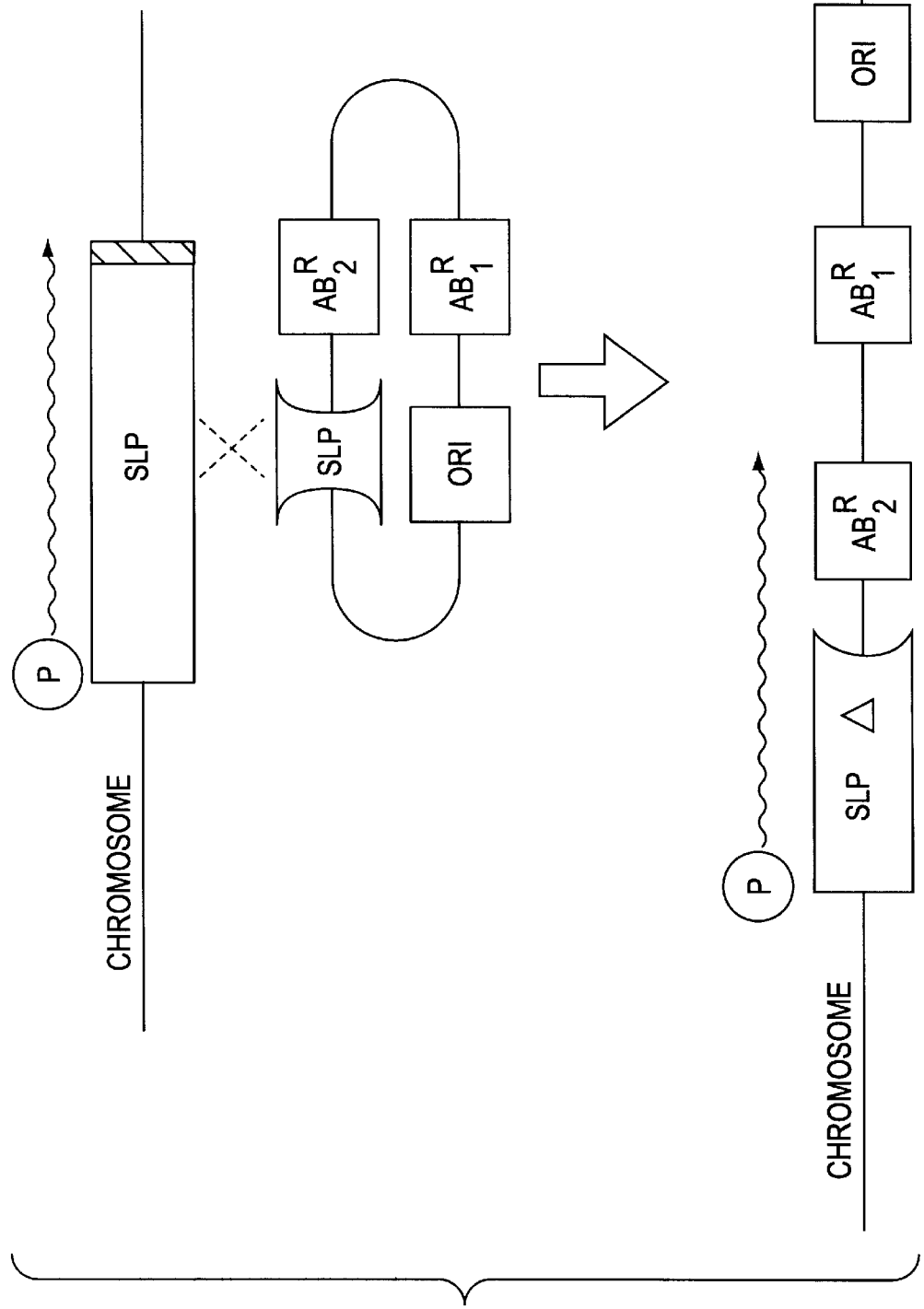

Effect of $Ca^{2+}$ on slp expression. In several cases it has been reported that $Ca^{2+}$ plays a key role in the assembly of the surface-layer on the bacteria (Feraldo et al, 1991 Yang et al, 1992). Moreover, Adachi and co- workers (1991) observed that $Ca^{2+}$ repressed the expression of the cell wall protein gene operon of *B. brevis* 47. In this context the previously constructed Pslp-uidA fusions proved to be excellent tools to monitor the possible effect of $Ca^{2+}$ on slp gene expression. Bacteria were grown in LB medium supplemented with an overdose $Ca^{2+}$ (7.5 mM) and compared to cells grown in the absence of $Ca^{2+}$. β-glucuronidase activity was measured 4 hours after dilution of the cultures ($\frac{1}{100}$) and simultaneous addition of $Ca^{2+}$ to the medium. As can be seen in FIG. 12, addition of $Ca^{2+}$ resulted in a two-fold reduction of β-glucuronidase activity in all mutants up to position −440, whereas mutants containing only promoter P1 were immune to this negative effect. These results suggest that the $Ca^{2+}$ repression is located at promoters P2 and/or P3. These observations were confirmed when assaying enzyme activity 24 hours after addition of $Ca^{2+}$ (data now shown).

Example 3

1. Materials and Methods

Figure 14A:
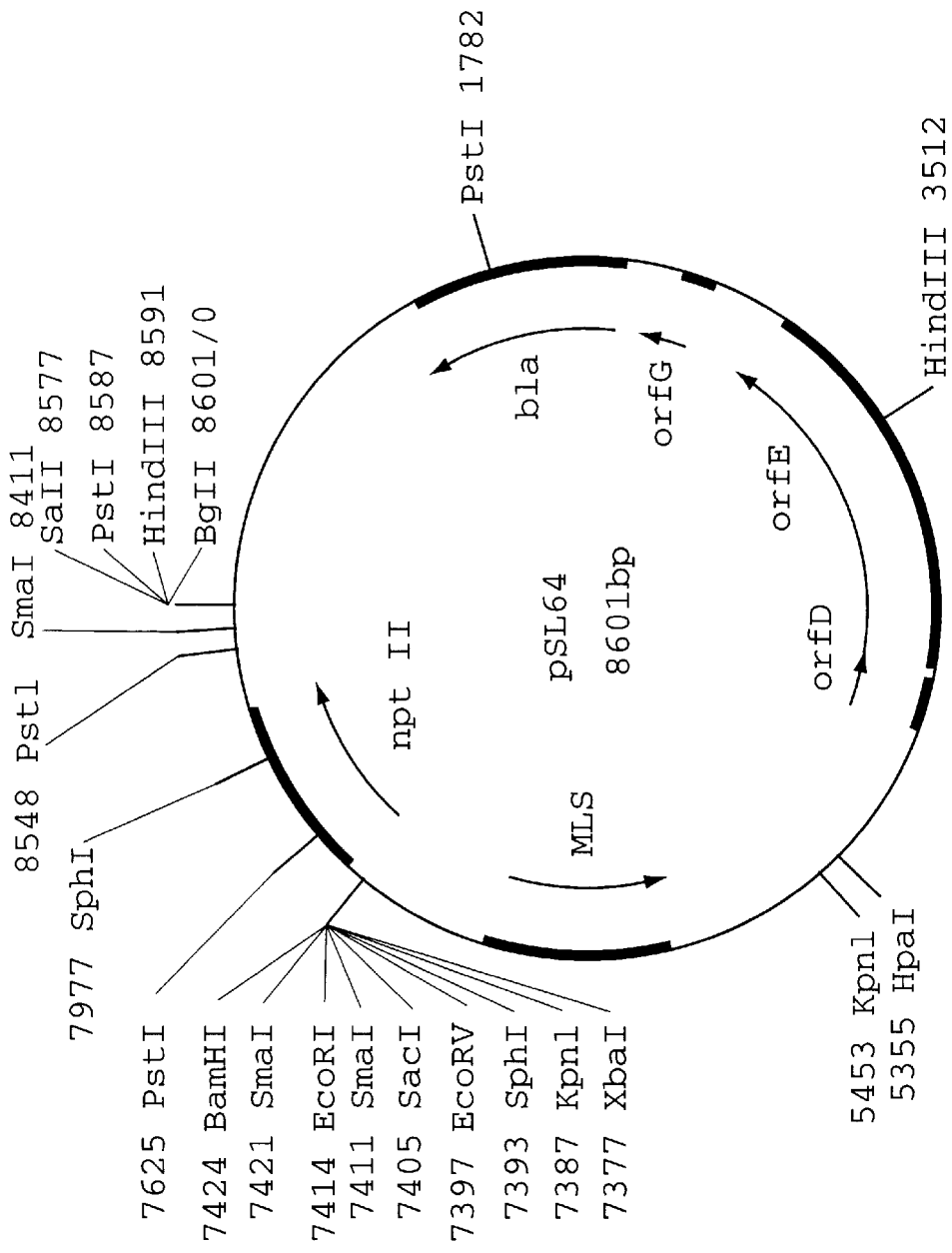
Figure 14B:
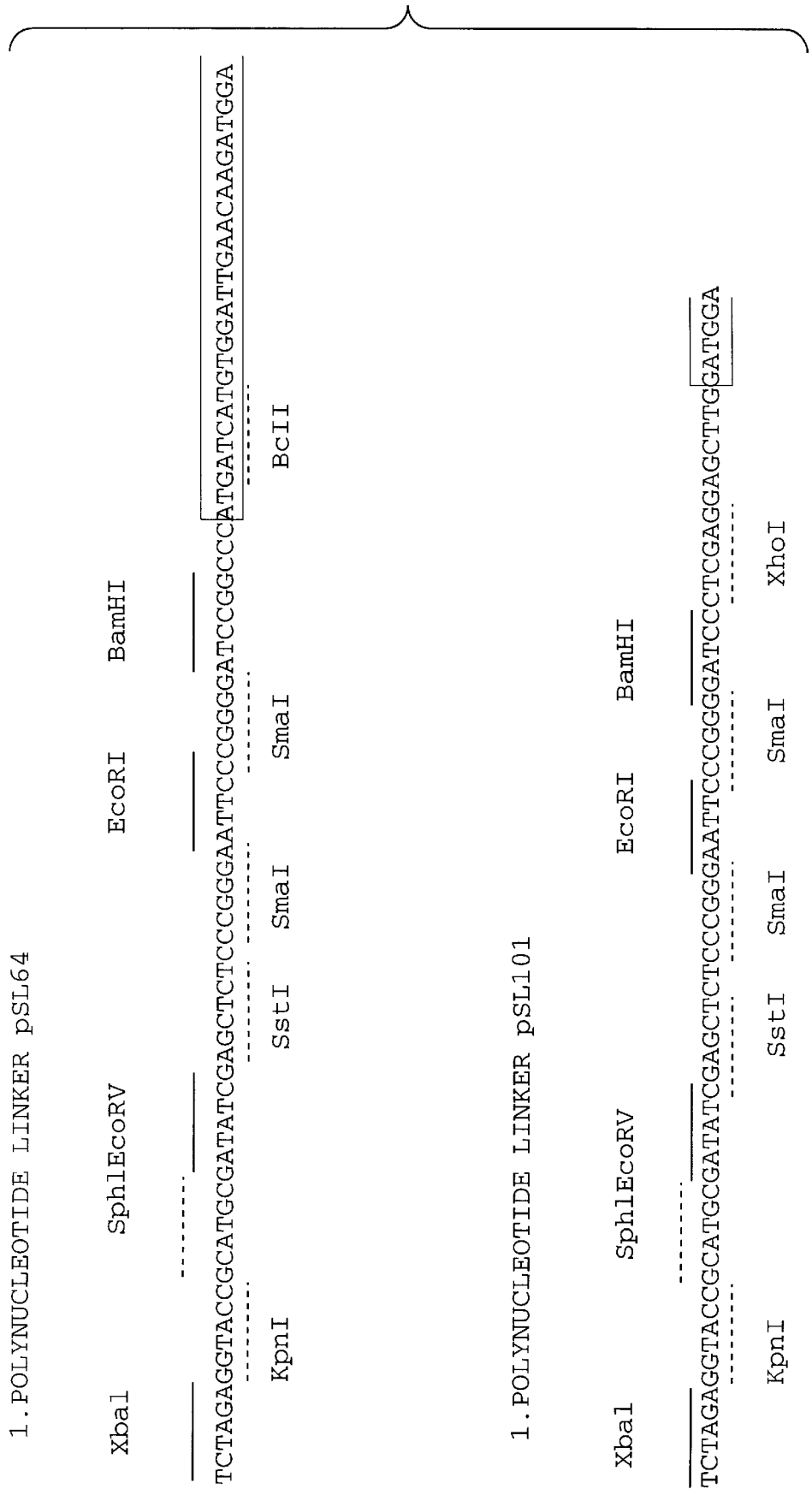

Bacterial strains and plasmids. Growth media and selective antibiotic concentrations for *B. sphaericus* P-1 have been described in Example 1. The plasmid pSL64, used as a basis for the construction of the different intermediate vectors, was isolated by insertion of a promoterless nptII gene as a 1.12-kb BamHI/SalI fragment from pKm109/2 (Reiss et al, 1984a) into the bifunctional, erythromycin resistance ($Em^R$) encoding vector pSL40 of Example 1 (FIG. 14A). The nucleotide sequence of the linker preceding the nptII gene in pSL64 is shown in FIG. 14B1.

Figure 15B:
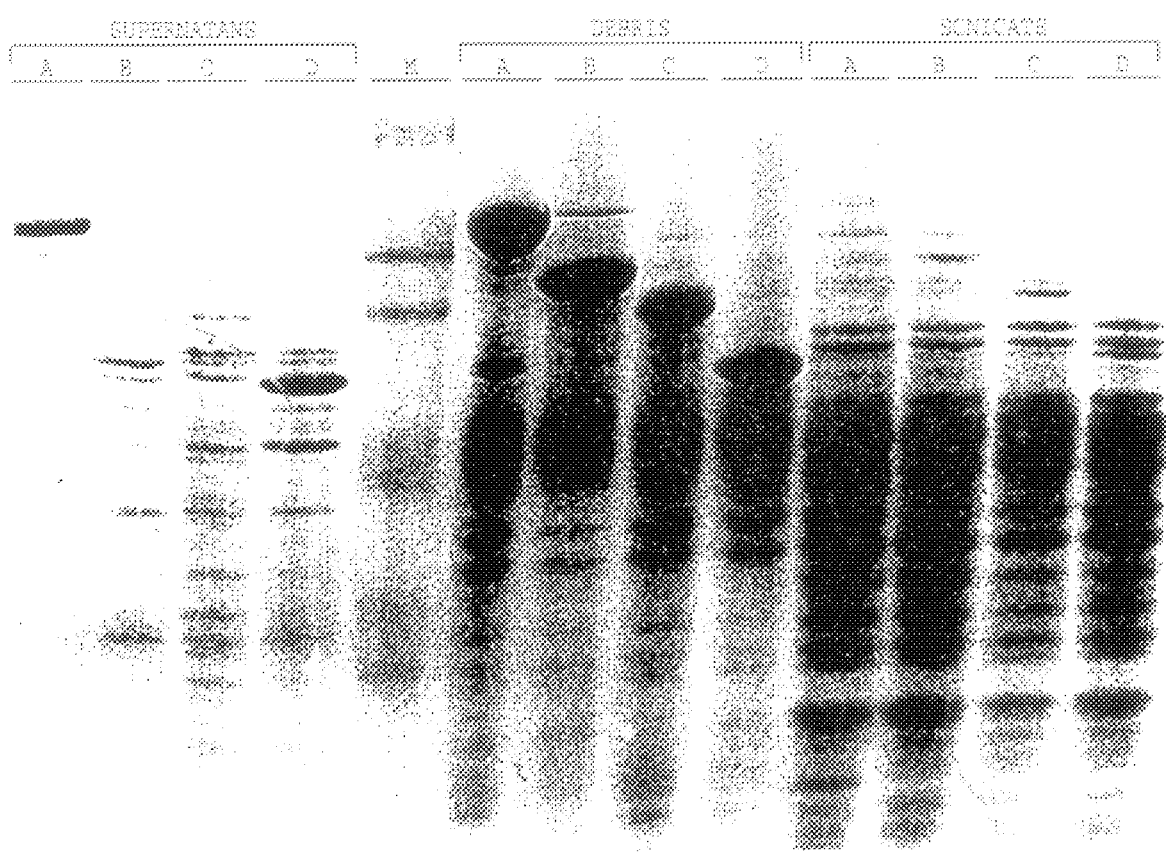

A similar plasmid (pSL101) was constructed by exchange of the BamHI/NcoI fragment of pSL64 for a similar sized fragment of pLKM92 to shift the reading frame of the nptII gene, compared to the multicloning site. pLKM92 is pKm109/90 (Reiss et al, 1984a) with a slightly modified polylinker. The nucleotide sequence of the linker preceding the nptII gene in pSL101 is shown in FIG. 14B2.

pSIA, pSL10, and pSL20 are subclones of the slp gene of Example 2 and are indicated on FIG. 15. Intermediate vectors, constructed in the course of this study are summarized in Table IV:

TABLE IV

Intermediate Vectors

| Plasmid Name | Cloned internal part of SLP[a] | Cloning Vector |
|---|---|---|
| pSL66 | 2048–2854 | pSL64 |
| pSL68 | 1470–2476 | pSL64 |
| pSL69 | 443–2053 | pSL64 |
| pSL70 | 443–1609 | pSL64 |
| pSL71 | 49–807 | pSL64 |
| pSL102 | 443–2053 | pSL101 |
| pSL111 | 443–2053 | pSL64[b] |
| pSL113 | 2084–2854 | pSL101 |

[a]bp 1 is the A base of the start codon;
[b]containing the 554-bp Sau3A fragment encoding the central part of S1.

Transformation. Competent *E. coli* MC1061 strains were prepared and transformed according to Kushner (1978), whereas transformation of *B. sphaericus* P-1 was achieved by electroportation as described in Example 1.

Sacculi preparation. Native sacculi were prepared by a protocol described by Sara and Sleytr (1987) and modified for *B. sphaericus* P-1 or derivative strains were grown overnight at 37° C. in TB medium (Tartof and Hobbs, 1987) on a gyratory shaker. Cells were harvested by centrifugation, resuspended in 50 mM Tris-HCl, pH 7.2 (50 ml per 100 g pellet), and sonicated for 1 min (40 Watt, using a Bransic Sonic Power Co. sonicator). Triton X-100 was added to a final concentration of 2%, and the mixture was incubated, with agitation, for 30 min at 50° C. Treated cells were collected by centrifugation (15,000 g, 10 min), and washed three times with cold, distilled $H_2O$. The pellet was resuspended in 5 mM $MgCl_2$, containing DNAse (5 μg/ml) and RNAse (20 μg/ml), and incubated for 15 min at 37° C. The resulting native sacculi were pelleted, washed three times with cold distilled $H_2O$, and resuspended in 20 ml buffer (20 mM Tris-HCl, pH 7.2, 2.5 mM $CaCl_2$, and 2 mM phenylmethylsulfonylfluoride).

Enzymatic assays. Enzymatic assays were performed either on trichloroacetic acid (TCA)-precipitated culture supernatants or on insoluble and soluble fractions of sonicated cells (4 times 10 sec, 40 W). NPTII activity was assayed by the in situ phosphorylation assay after separation of the proteins on non-denaturing polyacrylamide gels (Reiss et al, 1984b). Nicotinamide adenine dinucleotide (NAD) glycohydrolase activity was measured as the release of $^{14}C$-labelled nicotinamide from [carbonyl-$^{14}C$]NAD as described by Locht et al, (1987).

SDS-PAGE and immunoblotting. Sodium dodecyl sulfate polyacrylamide gel electrophoresis and Western blotting were performed by standard procedures (Laemmli, 1979). The filters were blocked with 2% Tween 20 and incubated with an 1:1000 dilution of the specific rabbit (anti- NPTII) or goat (anti-pertussis toxin [PT]) serum, followed by alkaline phosphatase conjugated goat anti-rabbit or mouse anti-goat IgG (Bio-Rad) as described by the manufacturers.

Immunogenicity of recombinant bacteria with composite S-layers in mice. Groups of five female Balb-C mice were injected (intraperitoneally) with different titers of recombinant P-1::pSL111 bacteria ($10^7$, $10^8$, and $10^9$ colony forming units (CFU)), corresponding to an estimated amount of 0.1, 1, and 10 μg of S1 subunit of pertussis toxin, either with or without Freund's adjuvant. Control experiments included purified S1 subunit of PT, and recombinant P-1::pSL102 bacteria. Injections were repeated after 3 and 9 weeks. At week 12, sera samples were collected. Mice sera were screened for the presence of antibodies directed against PT S1 subunit in a sandwich ELISA. PT was used as antigen and captured by a Guinea pig antiserum.

General recombinant DNA techniques. These were according to Sambrook et al, (1989). Restriction enzymes were purchased from New England Biolabs, Pharmacia or Bethesda Research Laboratories and were used according to the manufacturers' recommendations. Elution of DNA fragments separated by agarose gel electrophoresis was done using Gene Clean (Trade Mark) kit (Bio101 Inc, La Jolla, Calif., US). Southern transfer and hybridization were performed using Hybond $N^+$ membranes (Amersham) and Quickprime (Trade Mark) labelling kit (Pharmacia) to prepare $^{32}P$-labelled probes.

2. Results

Analysis of carboxy-terminal deletions of *B. sphaericus* P-1 SLP. Sequence analysis of the 4.5-kb slp gene of *B. sphaericus* P-1 revealed that the predicted first 200 amino acids of SLP were highly similar to the deduced sequence of the SLP of *B. sphaericus* 2362 (Bowditch et al, 1989), whereas the remaining parts of the proteins were highly divergent. Potential transmembrane helices were predicted to be located near the carboxy-terminal ends of both proteins (Bowditch et al, 1989). Therefore, these conserved motifs might be important in the build-up or anchoring of the S-layer. The fraction of the non-homologous COOH-terminal part of *B. sphaericus* P-1 SLP that could be removed without notable interference with S-layer assembly was determined by progressive deletions.

Therefore, several intermediate vectors were constructed (based on the bifunctional vector pSL64; Table IV) that contained different internal fragments of the slp gene, cloned upstream of a promoterless nptII gene (pSL66, pSL68, pSL69, pSL70, pSL71; Table IV and FIG. 15A). These constructs were introduced into *B. sphaericus* P-1 by electroporation and selection for $Em^R$ transformants. Neomycin-resistant (NmR) colonies, and thus putative single homologous recombinants, were obtained for the P-1 strains transformed by almost all intermediate vectors, except for pSL71 which contained the most amino-terminally located fragment of the slp gene.

Southern analysis revealed the patterns expected for single homologous recombination (see FIG. 16 for pSL69 integration). Culture supernatants, insoluble cell debris, and soluble cell contents after sonication of the strains carrying the different carboxy-terminal deletions were analyzed by SDS-PAGE electrophoresis (FIG. 15B). Abundant amounts of proteins with the expected molecular masses (see FIG. 15A) could be readily observed in the insoluble cell fraction. In contrast with the rather abundant presence of SLP in culture supernatants of wild-type P-1, no such proteins were observed in culture supernatant of strains expressing truncated SLPs, except for P-1::pSL69 (data not shown for P-1::pSL70). These data suggest that, whereas the carboxy-terminal part of the SLP and in particular residues numbered 536 to 1252 in FIG. 6 are dispensable, the amino-terminal part and especially residues numbered 31 to 269 in FIG. 6 are absolutely required for viability of P-1 cells. Residues numbered 31 to 269 in FIG. 6 constitute the N-terminal 239 or 19.56% residues of the mature SLP.

Translational fusion of reporter proteins to the carboxy-terminus of truncated SLPs. To determine whether the deletable part of SLP can be replaced by a protein of interest, we fused reporter proteins NPTII and the soluble fragment of the subunit S1 of toxin produced by Bordetella pertussis (PT) to the carboxy-terminus of truncated SLPs. To achieve this, a similar strategy as described above was used with the modification that the intermediate vectors now contained an internal slp part, translationally fused to either nptII (pSL102, pSL113; Table IV) or PT in fusion with NPTII (PSL111; Table IV). FIG. 17 summarises the expected fusion proteins generated by the different intermediate vectors. $Nm^R$ colonies, putative integrants, were selected after introduction of these intermediate vectors into P-1 by electroporation and selection of $Em^R$ transformants. Southern hybridizations of BglII-digested total DNA of these candidates with $^{32}P$-labelled pSL20 (containing a 4-kb BglII fragment of the slp gene; FIG. 15A), revealed the expected patterns after single homologous recombination through the cloned slp part (FIG. 16).

In SDS-PAGE analysis of total protein extracts of recombinant strains P-1::pSL69, P-1::pSL102 and P-1::pSL113 (FIG. 18A), major protein bands were observed at 74 kDa, 102 kDa and 130 kDa, respectively, the sizes expected for the truncated SLP or the two different fusion proteins. In total protein extracts of P-1::pSL111 (FIG. 18C), however, only a faint protein band of the expected size (120 kDa) could be observed. The fusion SLPs fractionated predominantly to the cell debris after sonication, as was also observed for the truncated SLPs.

Figure 18A:
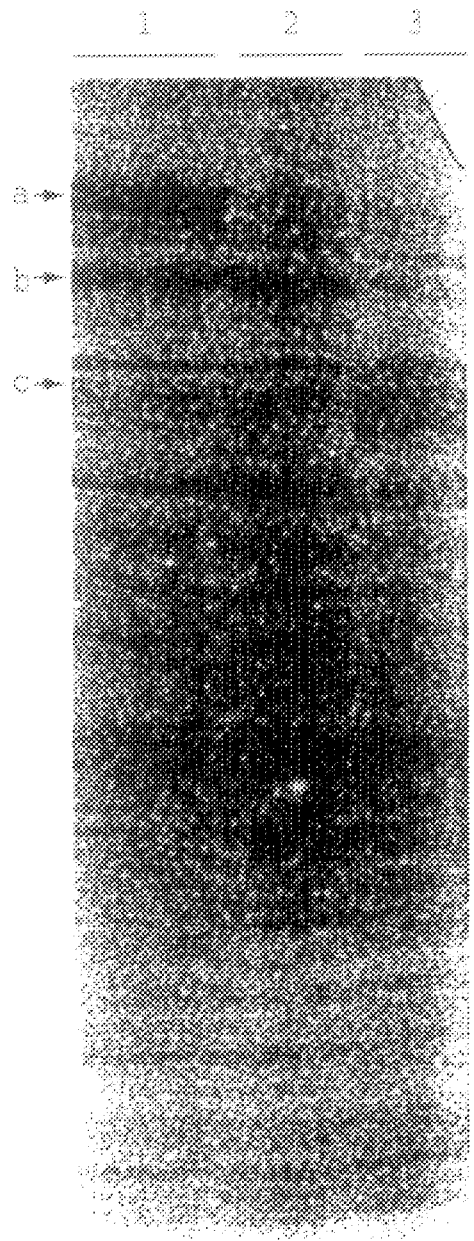
Figure 18B:
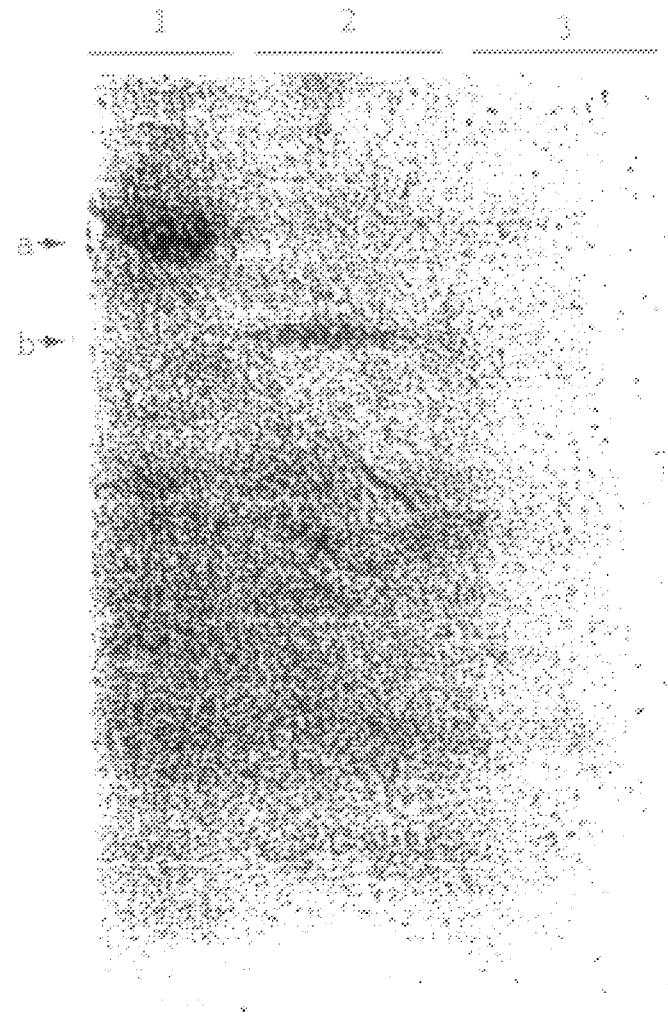
Figure 18C:
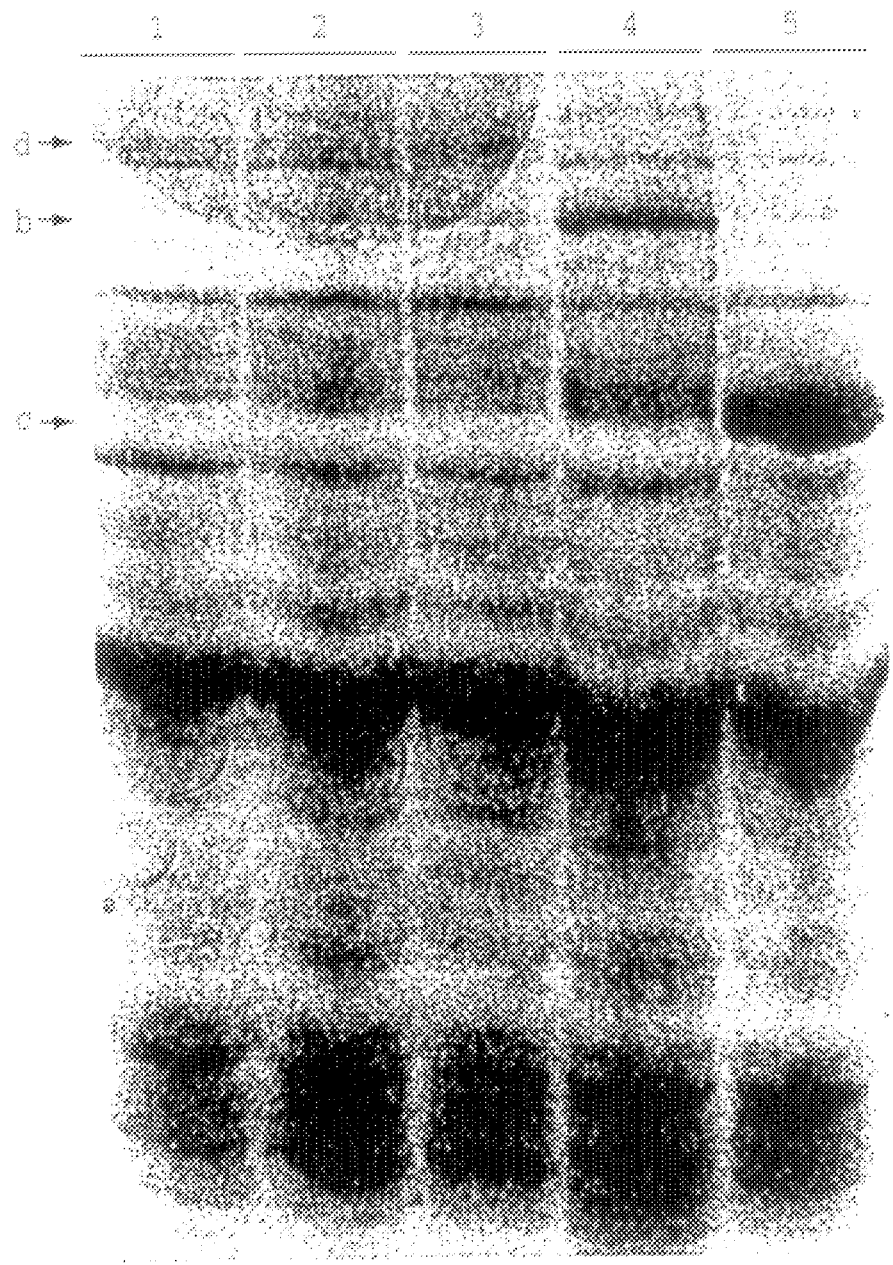
Figure 18D:
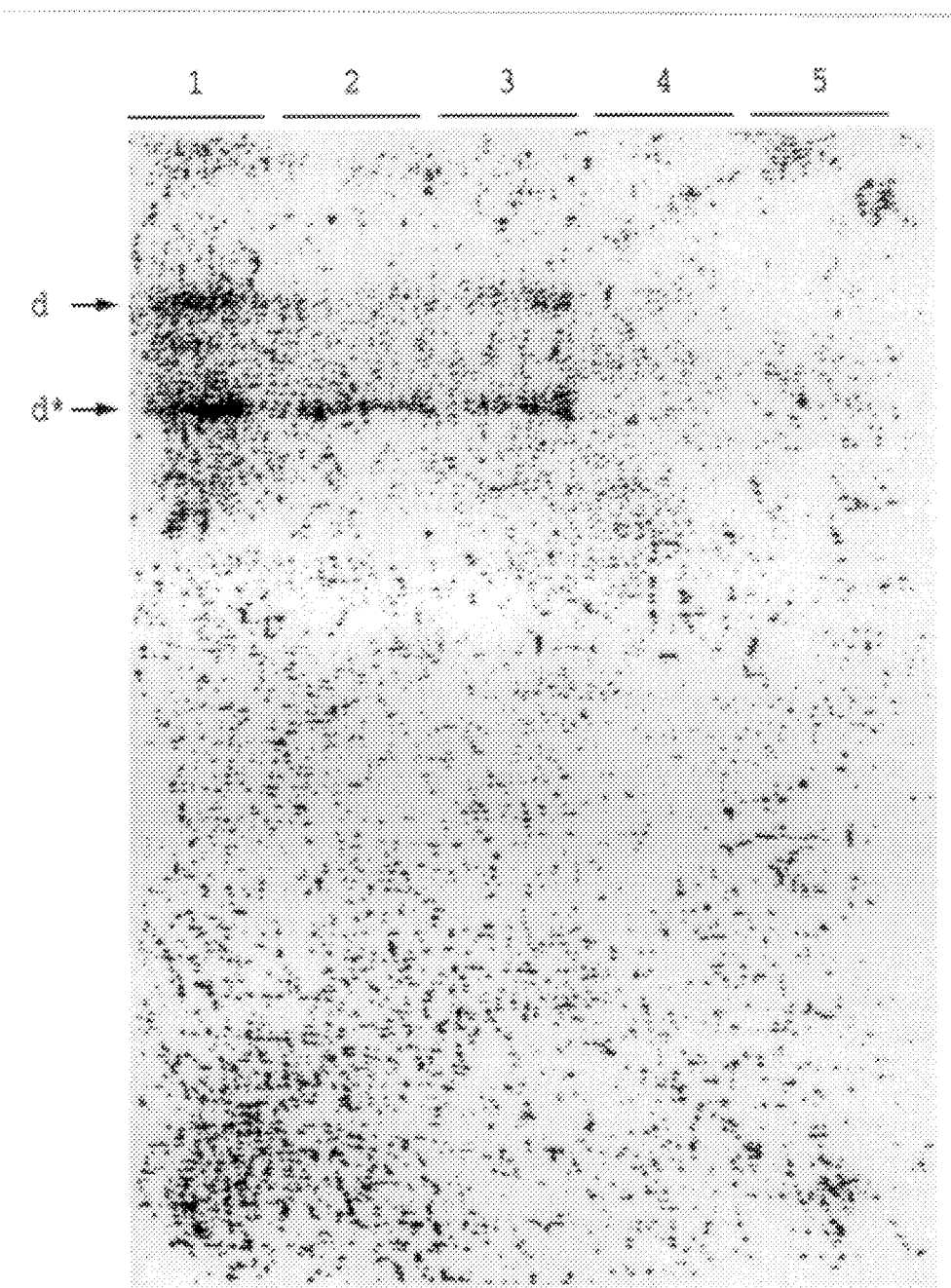

Western blottings of similar SDS-PAGE gels were challenged with anti-NPTII or anti-PT antibodies. Anti-NPTII reacted only with the 102-kDa and 130-kDa proteins in P-1::pSL102 and P-1::pSL113 protein extracts, respectively (FIG. 18C), whereas in P1::pSL111 extracts, the 120-kDa protein was revealed (data not shown). No cross-reaction was observed with proteins from P-1::pSL69. Anti-PT detected two specific proteins in P-1::pSL111 (120 kDa and 90 kDa), and four specific low-molecular mass proteins, that were also revealed in P-1::pSL69 extracts (FIG. 18D). Signals with both anti-PT and anti-NPTII were significantly enhanced when using proteins from native sacculi preparations (see below).

Reporter proteins fused to SLP retain their enzymatic activity. Because both proteins used as reporters in this study exhibit enzymatic activity that can be relatively quickly assayed, we determined whether the fusion proteins retained these catalytic abilities.

Kanamycin phosphorylation activity of fusion proteins was determined by the in gel assay, using either TCA-precipitated culture supernatants, or cell debris and soluble fraction after sonication. Significant phosphorylation activity was observed in all recombinant strains (but not in P-1 or in P-1::pSL69 extracts) and was confirmed almost exclusively to the insoluble cell debris fraction after sonication (FIG. 19).

NAD-glycohydrolase activity, specified by the S1 subunit of the *B. pertussis* toxin, was determined on TCA-precipitated culture supernatant, or cell debris and soluble fraction after sonication of the recombinant strain P-1::pSL111 (Table V), in comparison to a calibration curve using purified PT toxin. Again, significant enzymatic activities were only detected in cellular debris fraction of P-1::pSL111. The apparently high, a specific hydrolase activity detected in the supernatant of both P-1::pSL111 and P-1::pSL69 is due to acid hydrolysis caused by TCA residues from the precipitation (data now shown).

TABLE V

NAD-glycohydrolase activities of recombinant P-1 strains

| Protein Source | Released C14-nicotinamide (cmp) |
|---|---|
| PT toxin (µg/ml) | |
| 0 | 1860 |
| 1 | 5350 |
| 5 | 10520 |
| 10 | 14810 |
| 20 | 21850 |
| 40 | 26050 |
| P-1::pSL69 | |
| cell debris | 1340 |
| sonicate | 1480 |
| P-1::pSL111 | |
| cell debris | 5380 |
| sonicate | 1530 |

Carboxy-terminal fusions to SLP assemble in a functional S-layer. To address the question whether fusion proteins between truncated SLP and NPTII assemble into a S-layer, intact bacteria were immunogold-labelled using anti-NPTII antibodies. Significant accumulation of label on the bacteria was observed with P-1::pSL102 and to a lesser extent with P-1::pSL113 (FIGS. 20A and 20B). No background label could be found using either P-1 or P-1::pSL69 (which contains an intracellular NPTII protein).

Figure 21A:
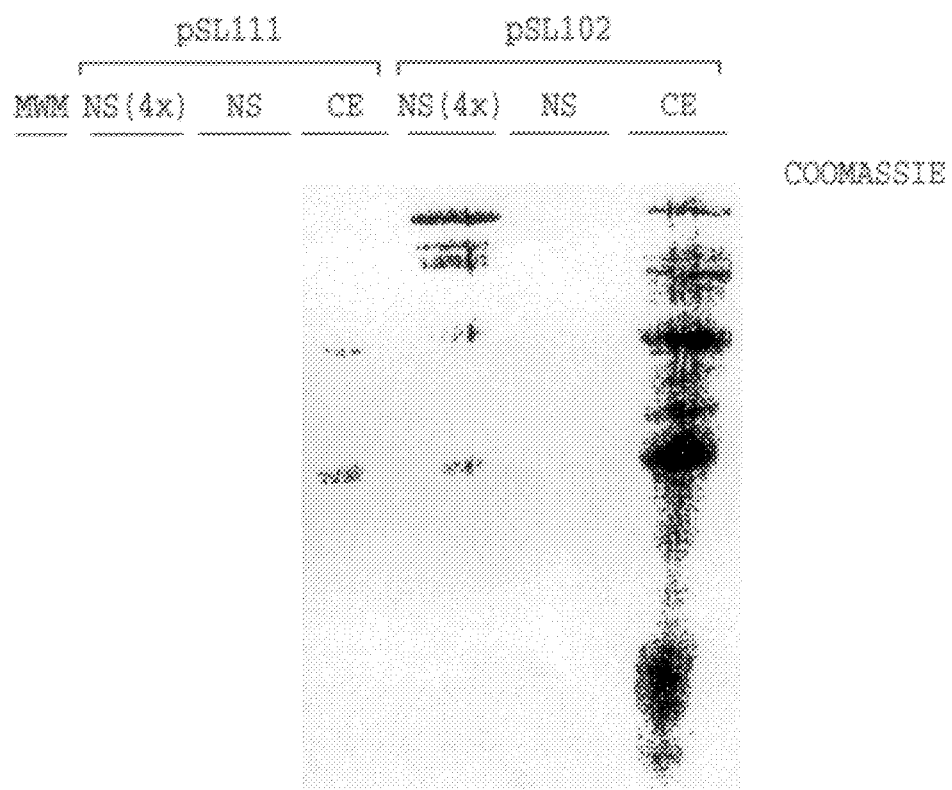
Figure 21B:
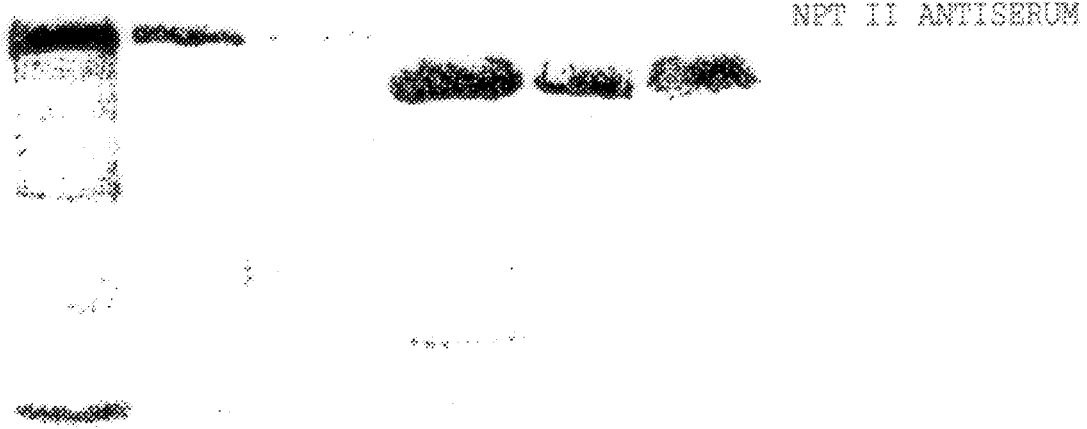
Figure 21C:
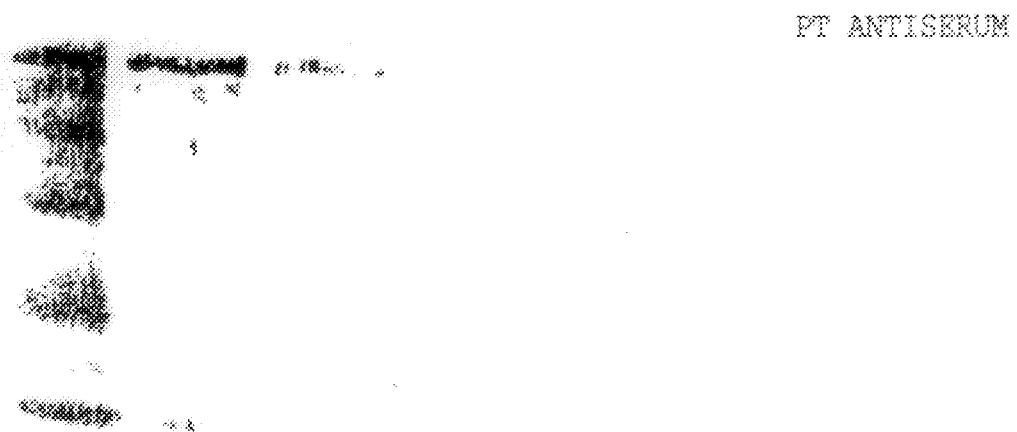

Circumstantial evidence for the assembly of the fusion proteins into an S-layer, comes from the preparation of ghost cells, or native sacculi as described by Sara and Sleytr (1987), in which cytoplasm and membrane are removed without affecting the structural integrity of the peptideglycan layer and the S-layer. Application of this protocol to recombinant P-1::pSL102, and P-1::pSL111 strains resulted in sacculi preparations, significantly enriched in fusion S-layer protein (FIG. 21A). Western blots, challenged with anti-NPTI or anti-PT detected readily the fusion proteins (FIGS. 21B and 21C).

The immunogenicity of the composite S-layers was determined by injection of the recombinant bacteria P-1::pSL111, expressing the S1 subunit of PT fused to SLP, along with purified S1 and recombinant P-1::pSL102 bacteria as controls. S1 antibody titers were determined after 12 weeks by ELISA (Table VI). A significant higher amount of S1-recognizing antibodies were detected in blood samples of the groups of mice injected by the highest concentration of the recombinant bacteria expressing the S1-subunit in a composite S-layer (P-1::pSL111).

TABLE VI

Immunogenicity of recombinant P-1::pSL111 in Balb/c mice

| | Antigen (µg) | Dilution 1:20 | Dilution 1:80 |
|---|---|---|---|
| S1 | 0.1 | 19.7 | 14.9 |
| | 1 | 426.1 | 402.1 |
| | 10 | 465.5 | 460.8 |
| S1 + AF | 0.1 | 132.5 | 56.0 |
| | 1 | 418.2 | 432.4 |
| | 10 | 457.8 | 453.7 |
| IB111 | 0.1 | 49.5 | 2.2 |
| | 1 | 39.8 | 1.9 |
| | 10 | 238.7 | 116.8 |
| IB111 + AF | 0.1 | 160.9 | 75.7 |
| | 1 | 158.8 | 70.3 |
| | 10 | 354.3 | 210.8 |
| IB102 | 0.1 | 34.5 | 3.8 |
| | 1 | 43.9 | 1.7 |
| | 10 | 67.6 | 6.5 |
| IB102 + AF | 0.1 | 117.0 | 16.8 |
| | 1 | 151.1 | 57.4 |
| | 10 | 160.1 | 65.2 |

Values are geometric means of ELISA titer readings of five independent injections. AF, Freund's adjuvant; IB111, intact bacterial P-1::pSL111; IB102, intact bacterial P-1::pSL102.

TABLE VII

Detailed information on the construction of intermediate vectors for the construction of truncated SLP's and composite SLP's.

Note on numbering: base 1 = A of ATG of the slp gene
(= mRNA numbering + 95)
Simple SLP clones

| | | |
|---|---|---|
| pSL4 | = | 1536 bp HindIII fragment in pUC18 HindIII. This fragment contains the complete slp promoter and slp gene portion 1 to 142. |
| pSL5 | = | slp gene portion 49–807 (PvuII-PvuII) in pUC18 SmaI. |
| pSL10 | = | slp gene portion 443–2053 (BglII-BglII) in pUC18 BamHI. |
| pSL20 | = | 3048 bp HindIII fragment in pUC18 HindIII. This fragment contains the slp gene portion 1049 to end of ORP (3759) and the transcription termination signal. |

TABLE VII-continued

Detailed information on the construction of intermediate vectors for the construction of truncated SLP's and composite SLP's.

Truncated SLP intermediate vectors

| Name | Cloned slp part | Restriction site and clone | Site in pSL64 |
|---|---|---|---|
| pSL66 | 2048–2854 | pSL20 BglII | BamHI |
| pSL68 | 1470–2476 | pSL20 PvuII | EcoRV |
| pSL69 | 443–2053 | pSL10 XbaI/EcoRI | XbaI/EcoRI |
| pSL70 | 443–1609 | pSL10 XbaI/HpaI | XbaI/EcoRV |
| pSL71 | 49–807 | pSL5 XbaI/EcoRI | XbaI/EcoRI |

Composite SLP intermediate vectors

Figure 4A:
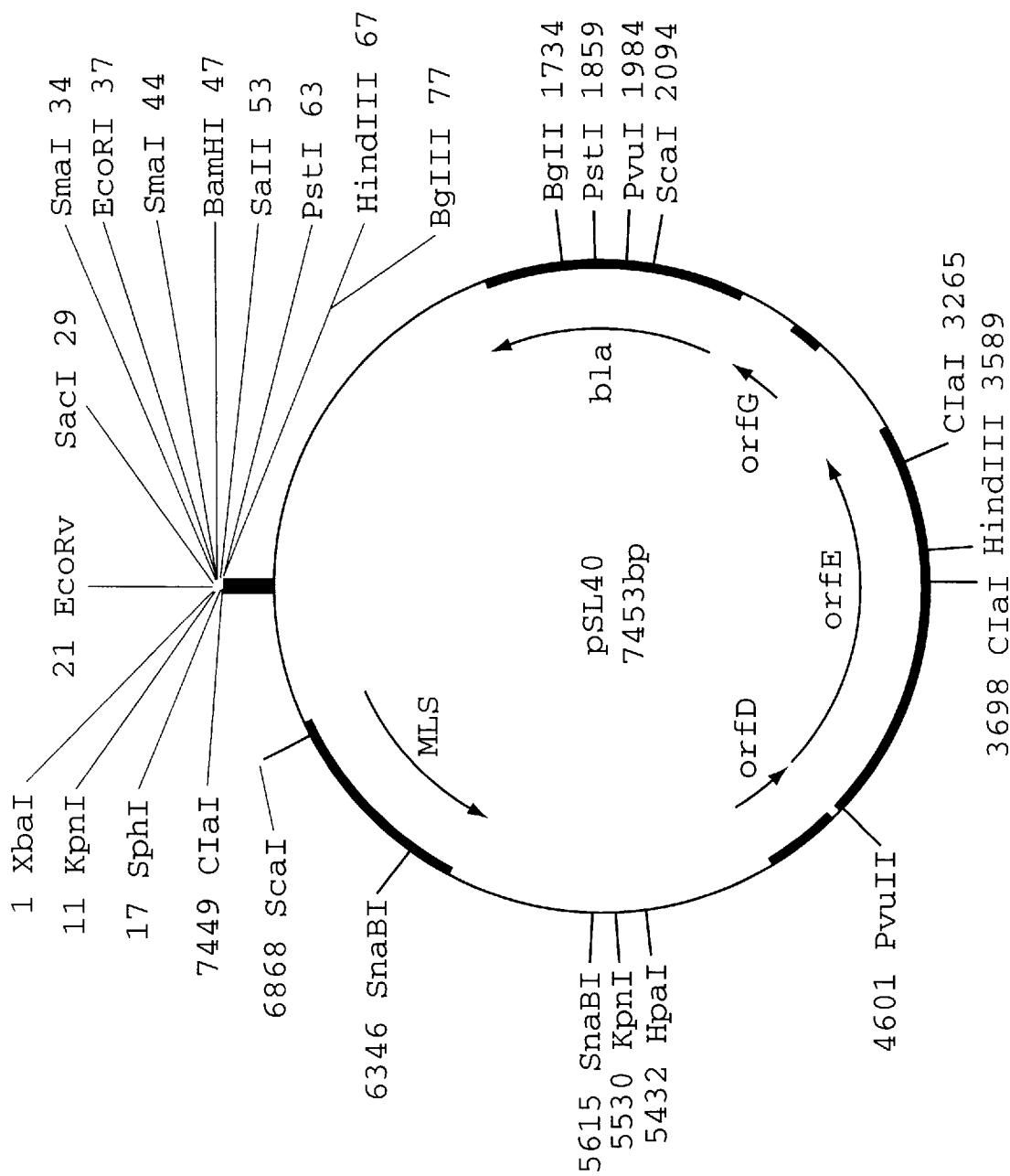
Figure 4B:
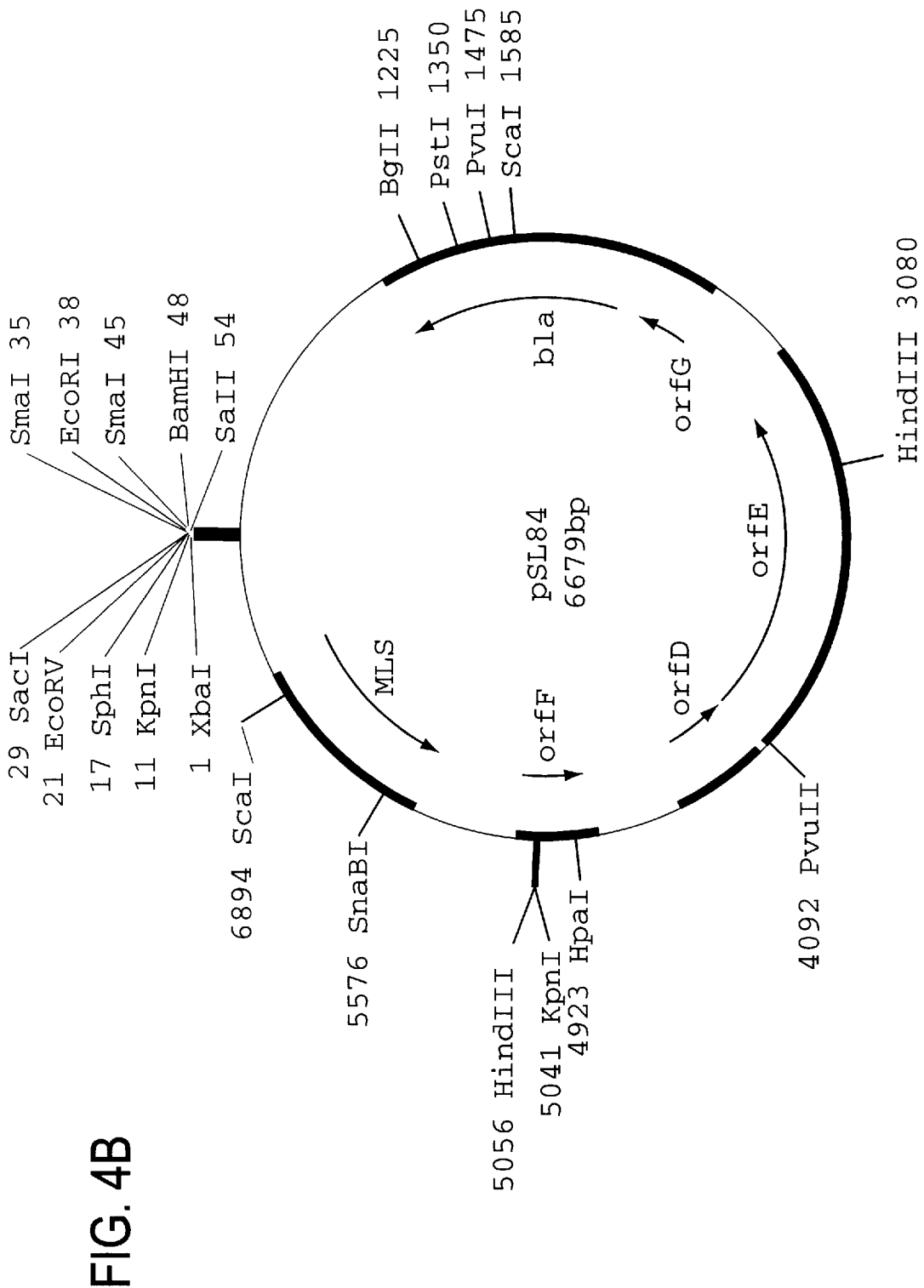
Figure 5:
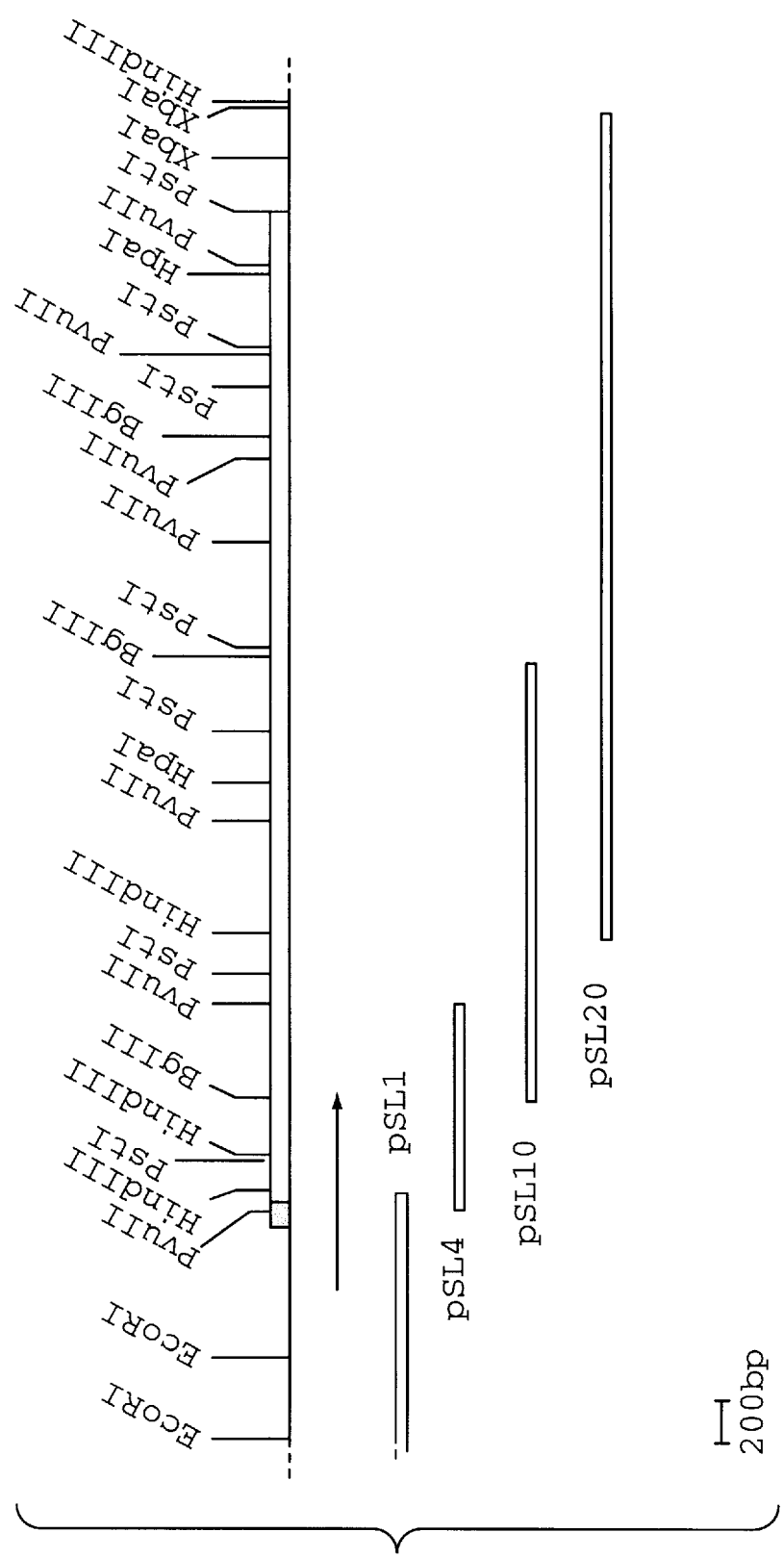
Figure 7:
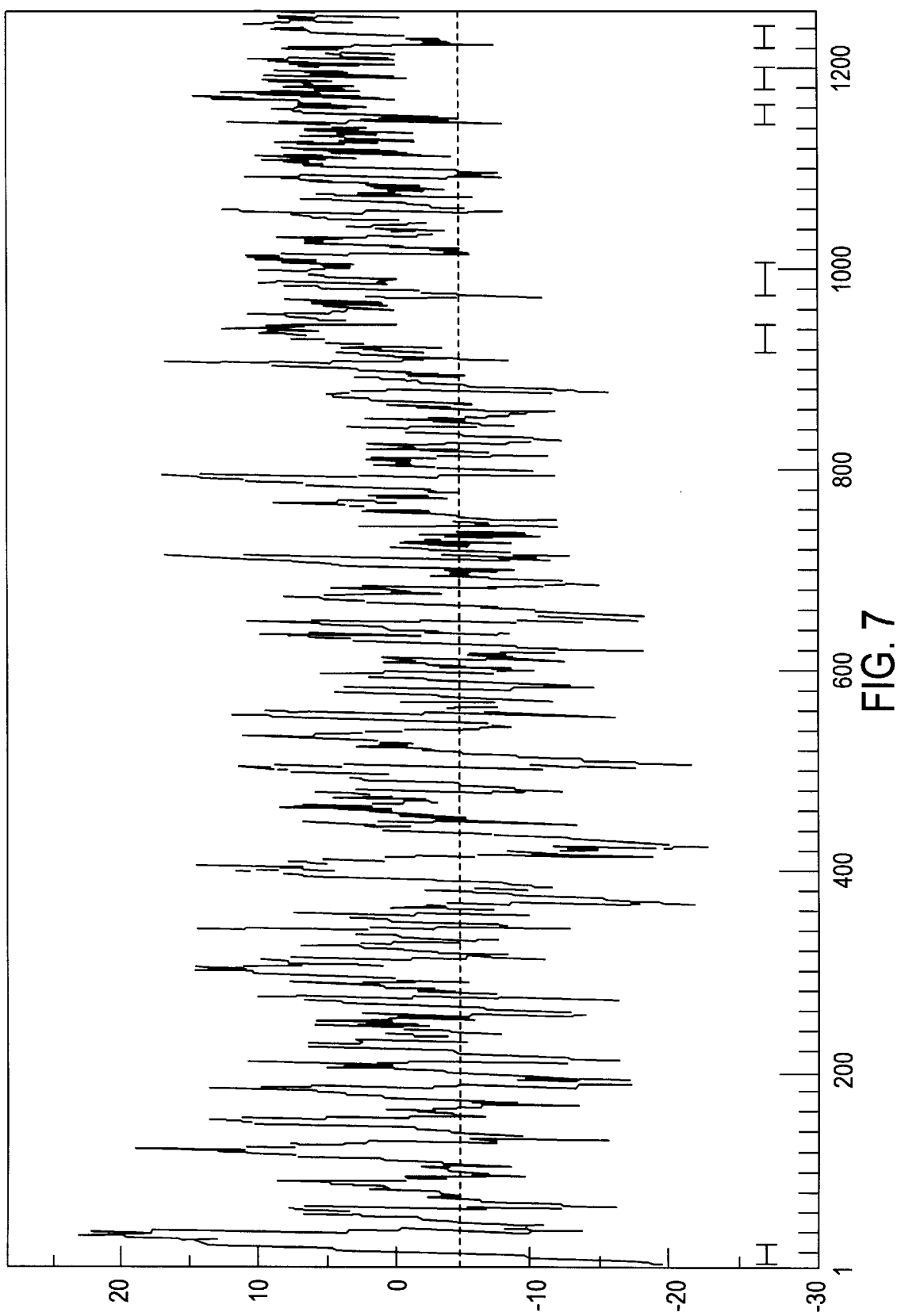

| | |
|---|---|
| pSL109 | 554 bp Sau3A fragment cloned in BamHI site of pSL64 and selection of the correct orientation. |
| pSL102 | EcoRI-BglIII fragment of pSL20 (1049–2053) in BamHI site of pSL101. |
| pSL113 | BglII fragment of pSL20 (2048–2854) in BamHI site of pSL101. |
| pSL111: | Same as pSL102 in BamHI site of pSL109. |
| pSL40 = | 7453 bp high copy number bifunctional vector, Example 1 and FIG. 4A. |
| pSL84 = | 6679 bp low-copy number bifuncfional vector, Example 1 and FIG. 4B. |
| pSL150 = | promoterless β-glucuronidase gene isolated as 2558 bp BamHI/SphI fragment and cloned in pSL40 BamHI/SphI, Example 2. |
| pSL151–159 = | XbaI/NcoI fragments carrying progressive deletions of the slp promoter into pSL150 XbaI/NcoI. Exact end points of the deletions are indicated in Example 2 and FIG. 10. NcoI site coincides with ATG start codon. |
| pSL64 = | 1.12 kb BamHI/SalI fragment, carrying promoterless nptII gene from pKm109/2 into pSL40 BamHI/SalI, Example 3 and FIG. 14A. |
| pSL101 = | essentially the same as pSL64, but having another DNA linker in front of the nptII gene, Example 3 and FIG. 14B. |

References

Adachi et al (1989) J. Bacteriol. 171, 1010–1016.
Adachi et al (1991) J. Bacteriol. 176, 4243–4245.
Aiba et al (1981) J. Biol. Chem. 256, 11905–11910.
Bauw et al (1987) Proc. Natl. Acad. Sci. USA 84, 4806–4810.
Bone and Ellar (1989) FEMS Microbiol. Lett. 58, 171–178.
Botterman and Zabeau (1987) DNA 6, 583–591.
Bowditch et al (1989) J. Bacteriol. 171, 4178–4188.
Brutlag et al (1990) Comp. Appl. Biol. Sci. 6, 237–245.
Casadaban and Cohen (1980) J. Mol. Biol. 138, 179–207.
Cashel and Rudd (1987) In *Escherichia coli* and *Salmonella typhimurium*, Cellular and Molecular Biology, F. C. Neidhardt, J. L. Ingraham, K. B. Low, B. Magasanik, M. Schaechter, and H. E. Umbarger (Eds.). Washington, American Society for Microbiology, pp. 1410–1438.
Chang and Cohen (1978) J. Bacteriol. 134, 1141–1156.
Charles and Dougan (1990) Trends Biotechnol. 8, 117–121.
Chassy et al (1988) Trends Biotechnol. 6, 303–309.
Clewell et al (1974) J. Bacteriol. 117, 283–289.
Desomer et al (1990) Appl. Environm. Microbiol. 56, 2818–2825.
Faraldo et al (1991) J. Bacteriol. 173, 5346–5351.
Gasson and Davies (1980) FEMS Microbiol. Lett. 7, 51–53.
Georgiou et al (1993) Tibtech 11, 6–10.
Gonzalez et al (1981) Plasmid 5, 351–365.
Gruss and Ehrlich (1989) Microbiol. Rev. 53, 231–241.
Hager and Rabinowitz (1985). In The Molecular Biology of *Bacillus subtilis*, Vol II. D. A. Dubnau (Ed.) Orlando, Academic Press, 1–32.
Hanahan (1983) J. Mol. Biol. 166, 557–580.
Howard and Tipper (1973) J. Bacteriol. 113 (3) 1491–1504.
Jefferson et al (1986) Proc. Natl. Acad. Sci. USA 83, 8447–8451.
Johnston and Richmond (1970) J. Gen. Microbiol. 60, 137–139.
König (1988) Can. J. Microbiol. 34, 395–406.
Kushner (1978). In Genetic engineering, Boyer and Nicosia (eds.), Amsterdam:Elsevier/North-Holland Biochemical Press, pp. 17–23.
Kyte and Doolittle (1982) J. Mol. Biol. 157, 105–132.
Laemmli (1970) Nature (London) 227, 680–685.
Lepault et al (1986) J. Bacteriol 168, 303–308.
Lewis et al (1987) J. Bacteriol. 169, 72–79.
Locht et al (1987) Infection and Immunity 55, 2546–2553.
Lupas et al (1994) J. Bacteriol. 176, 1224–1233
Mielenz (1983) Proc. Natl. Acad. Sci. USA 80, 5975–5979.
Miller (1972) Experiments in Molecular genetics. New York, Cold Spring Harbor Laboratory.
Matuschek et al (1994) J. Bacteriol. 176, 3295–3302
Mongkolsuk et al (1983) J. Bacteriol. 155, 1399–1406.
Moran et al (1982) Mol. Gen. Genet. 186, 339–346.
Orzech and Burke (1984) FEMS Microbiol. Lett. 25, 91–95.
Peleman et al (1989) Plant Cell 1, 81–93.
Platt (1986) Ann. Rev. Biochem. 55, 339–372.
Rao and Argos (1986) Biochem. Biophys. Acta 869, 197–214.
Reiss et al (1984a) EMBO J. 3, 3317–3322.
Reiss et al (1984b) Gene 30, 211–218.
Sambrook et al (1989), Molecular cloning, a laboratory manual. Cold Spring Harbor, Cold Spring Harbor Laboratory Press.
Sanger et al (1977) Proc. Natl. Acad. Sci. USA 74, 5463–5467.
Sára and Sleytr (1987) J. Bacteriol. 169, 4092–4098.
Simon and Chopin (1988) Biochimie 70, 559–566.
Sleytr and Messner (1988) J. Bacteriol. 170, 2891–2897.
Smith et al (1993) Vaccine 11, 919–924.
Sonstein and Baldwin (1972) J. Bacteriol. 109, 262–265.
Swinfield et al (1990) Gene 87, 79–90.
Tagaki et al (1989) Agric. Biol. Chem. 53, 3099–3100.
Takao et al (1989) Appl. Micro and Biotech., Spring 1989, 30, 75–80.
Tang et al (1989) J. Bacteriol. 171, 12, 6637–6648.
Tartof and Hobbs (1987) Focus 9, 12.
Taylor and Burke (1990) FEMS Microbiol. Lett. 66, 125–128.
Tsuboi et al (1988) J. Bacteriol. 170, 935–945.
Tsuboi et al (1989) J. Bacteriol 171, 12, 6747–6752.

Tsukagoshi et al (1985) J. Bacteriol. 164, 3, 1182–1187.

Tsukagoshi (1987/8) (Crystalline Bacterial Cell Surface Layers, (EMBO Workshop, Vienna, Austria, Aug. 31–Sep. 2, 1987) Springer-Verlag, Sleytr, U. B., et al., ed., 1988, 145–148).

Vieira and Messing (1982) Gene 19, 259–268.

von Heijne (1986) Nucl. Acids Res. 14, 4683–4690.

Watson et al (1987) Molecular Biology of the Gene, 4th edition, The Benjamin/Cummings Publishing Company Inc.

Yamagata et al (1987) J. Bacteriol. 169, 3, 1239–1245.

Yamagata et al (1989) Proc. Natl. Acad. Sci. USA 86, 3589–3593

Yang et al (1992) J. Bacteriol. 174, 1258–1267.

Yanisch-Perron et al (1985) Gene 33, 103–119.

---

We claim:

1. A process of transforming *B. sphaericus* P-1 cells with DNA, which process comprises harvesting *B. sphaericus* P-1 cells at the late stationary growth phase, mixing the harvested cells with the DNA and effecting electroporation to cause entry of the DNA into the said cells.

* * * * *